(12) United States Patent
Hasegawa et al.

(10) Patent No.: US 7,169,541 B2
(45) Date of Patent: Jan. 30, 2007

(54) COMPOUND, POLYMER, RESIST COMPOSITION, AND PATTERNING PROCESS

(75) Inventors: Koji Hasegawa, Naka Kubiki-gun (JP); Takeshi Kinsho, Naka Kubiki-gun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 154 days.

(21) Appl. No.: 10/885,714

(22) Filed: Jul. 8, 2004

(65) Prior Publication Data

US 2005/0014092 A1  Jan. 20, 2005

(30) Foreign Application Priority Data

Jul. 17, 2003  (JP) .............................. 2003-276319

(51) Int. Cl.
*G03F 7/00* (2006.01)
*G03F 7/26* (2006.01)
*G03F 7/40* (2006.01)

(52) U.S. Cl. .................. 430/331; 430/270.1; 430/311; 430/330; 430/464

(58) Field of Classification Search ............. 430/270.1, 430/331
See application file for complete search history.

(56) References Cited

U.S. PATENT DOCUMENTS

| | | | |
|---|---|---|---|
| 3,258,501 A * | 6/1966 | Cannell ........................ 585/361 |
| 3,478,043 A * | 11/1969 | Arnold et al. ........... 546/281.7 |
| 4,491,628 A | 1/1985 | Ito et al. |
| 4,828,603 A * | 5/1989 | Patel et al. .................. 504/297 |
| 5,714,625 A | 2/1998 | Hada et al. |
| 5,843,624 A | 12/1998 | Houlihan et al. |
| 6,004,724 A | 12/1999 | Yamato et al. |
| 6,022,666 A | 2/2000 | Hada et al. |
| 6,261,738 B1 | 7/2001 | Asakura et al. |
| 6,517,990 B1 * | 2/2003 | Choi et al. ............... 430/270.1 |
| 2003/0059710 A1 * | 3/2003 | Inoue ...................... 430/270.1 |

FOREIGN PATENT DOCUMENTS

| | | |
|---|---|---|
| JP | B2 2-27660 | 6/1990 |
| JP | A 9-73173 | 3/1997 |
| JP | A 9-95479 | 4/1997 |
| JP | A 9-208554 | 8/1997 |
| JP | A 9-230588 | 9/1997 |
| JP | A 10-10739 | 1/1998 |
| JP | A 2000-314956 | 11/2000 |
| WO | WO 2005005404 A1 * | 1/2005 |

OTHER PUBLICATIONS

Marshall et al, Synthesis of a 2,7-Dioxatricyclo[4.2.1.0 3, 8]none: A Model Study for Possible Application in a Synthesis of Dictyoxetane. Journal of Organic Chemistry, 61(26), 9135-9145, 1996.*
Sanders et al , Fluorinated Oxetane-Containing Monomers for 157 nm Resist Applications. http://willson.cm.utexas.edu/Research/Sub_Files/157/Files/157_poly_oxetane.htm, Jan. 30, 2001.*

* cited by examiner

*Primary Examiner*—Amanda Walke
(74) *Attorney, Agent, or Firm*—Oliff & Berridge, PLC

(57) ABSTRACT

There is disclosed a polymer containing at least a repeating unit represented by the following general formula (1), and the resist composition containing the polymer as a base resin, especially a chemically amplified resist composition. There can be provided a resist composition which has etching resistance in a practical use level, and is excellent in an adhesion property with a substrate and an affinity with a developer, and has a sensitivity and resolving power which is far excellent compared with a conventional one, wherein swelling is small at the time of development, especially for photolithography which uses a high-energy beam as a light source, and especially be provided a chemically amplified resist composition (1)

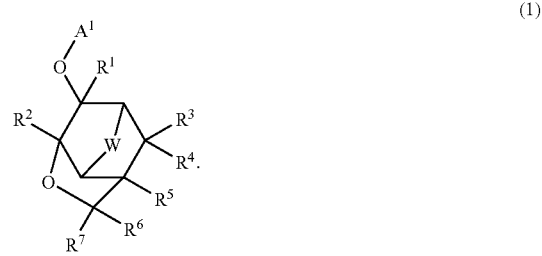

33 Claims, No Drawings

COMPOUND, POLYMER, RESIST COMPOSITION, AND PATTERNING PROCESS

BACKGROUND OF THE INVENTION

1. Field of the Invention

The present invention relates to a compound useful as a monomer for a polymer, for example, for a base resin of a chemically amplified resist composition suitable for an ultra-fine processing technology, a polymer which contains the compound as a monomer, and a resist composition which contains the polymer as a base resin, and a patterning process using the resist composition.

2. Description of the Related Art

It has been needed to make a pattern rule fine with a tendency of high integration and high-speed of LSI in recent years, and a far-ultraviolet-ray lithography is considered as excellent as an ultra-fine processing technology of the next generation. Among them, realization of photolithography using KrF excimer laser light, ArF excimer laser light, and $F_2$ excimer-laser light as a light source has been desired earnestly as technology indispensable to micro-processing of 0.3 μm or less.

For the resist composition for KrF excimer laser, a polyhydroxy styrene having both transparency and etching resistance which are in a usable level is a standard base resin on the fact (see, for example, Japanese Patent Publication No. 2-27660).

On the other hand, for the resist composition for ArF excimer lasers, there have been examined as a base resin a derivative of a polyacrylic acid or a polymethacrylic acid, a polymer which contains a cycloaliphatic compound in a backbone chain (see, for example, Japanese Patent Application Laid-open (KOKAI) No. 9-73173, and Japanese Patent Application Laid-open (KOKAI) No. 10-10739). However, there are both advantages and disadvantages in any of them, and a standard base resin has not yet been decided.

That is, there is an advantage such as a high reactivity of an acidolysis group and high adhesion property with substrate in the case of the resist composition using a derivative of a polyacrylic acid or a polymethacrylic acid, and a comparatively good result is obtained thereby as for sensitivity and a resolution power. However, etching resistance thereof is very low and is not practical, since a backbone chain of the resin is weak. On the other hand, in the case of the resist composition using a polymer which contains a cycloaliphatic compound in a backbone chain, although etching resistance is in a level of practical use, since the backbone chain of the resin is sufficiently strong, sensitivity and resolving power is low, since the reactivity of an acidolysis protective group is significantly inferior compared with those of (meth)acrylics. Furthermore, since the backbone chain of the resin is too strong, an adhesion property with a substrate is low, and it is not suitable either.

Moreover, there is collapse of a pattern due to swelling of a resist film as a common problem to both (meth) acrylic resins and the resin with a cycloaliphatic backbone chain. The resolving power of these kinds of the resist composition has been improved by making a difference in a resolution power before and after exposure large, and therefore, it is very hydrophobic. In the case of the resist composition with a highly hydrophobic property, a film is strongly kept in a non-exposed part and a film is dissolved immediately in an over-exposed part. However, in a quite large exposure area between them, it cannot be dissolved, but is swollen, even though a developer permeates therein. In a very detailed pattern size for which an ArF excimer laser is actually used, the resist composition in which the adjacent patterns are adhered by swelling and collapse cannot be used. With a need for a finer pattern rule, there has been needed a resist composition wherein sensitivity, resolving power, etching resistance, and an adhesion property with a substrate are excellent, and swelling is fully suppressed.

SUMMARY OF THE INVENTION

The present invention has been made in order to solve such problems. The object of the present invention is to provide a resist composition which has etching resistance in a practical use level, and is excellent in an adhesion property with a substrate and an affinity with a developer, and has a sensitivity and resolving power which is far excellent compared with a conventional one, wherein swelling is small at the time of development, especially for photolithography which uses a high-energy beam such as ArF excimer laser light, KrF excimer laser light or the like as a light source, and especially to provide a chemically amplified resist composition. Another object of the present invention is to provide a patterning process using such a resist composition.

To achieve the above mentioned object, the present invention provides a compound represented by the following general formula (1).

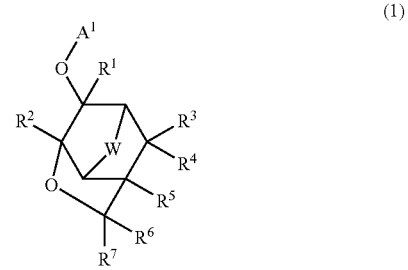

(1)

(In the formula, $A^1$ represents a polymerizable functional group which has a carbon-carbon double bond at least, $R^1$ and $R^2$ independently represent a hydrogen atom, or a linear, branched or cyclic monovalent hydrocarbon group having 1–10 carbon atoms, $R^3$–$R^7$ independently represent a hydrogen atom, or a linear, branched or cyclic monovalent hydrocarbon group having 1–10 carbon atoms which may contain a hetero atom, or two of $R^3$–$R^7$ may bond to each other and form an aliphatic-hydrocarbon ring, and W represents any one of $CH_2$, an oxygen atom and a sulfur atom.)

In this case, the compound represented by the above-mentioned general formula (1) may be, for example, a compound represented by the following general formula (2).

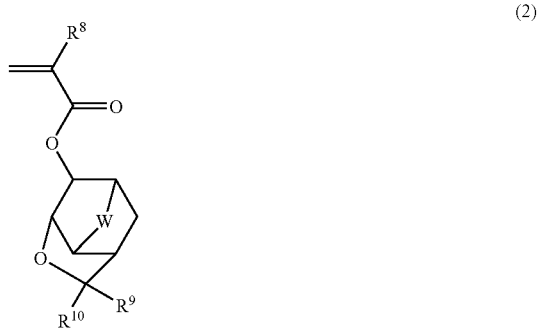

(2)

(In the formula, W is the same as that of the above-mentioned formula, $R^8$ represents a hydrogen atom, a methyl group, or a trifluoro methyl group, and $R^9$ and $R^{10}$ independently represent a hydrogen atom, a linear, branched, or cyclic monovalent hydrocarbon group having 1–10 carbon atoms, or $R^9$ and $R^{10}$ may bond to each other and form an aliphatic-hydrocarbon ring together with carbon atoms to which they bond.)

Moreover, the compound represented by the above-mentioned general formula (1) may be, for example, a compound represented by the following general formula (3).

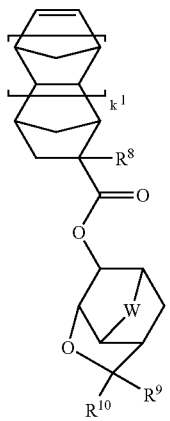

(3)

(In the formula, $R^8$–$R^{10}$ and W are the same as those of the above formulae, and $k^1$ is 0 or 1.)

The present invention provides a polymer comprising at least the above-mentioned compound of the present invention as a repeating unit.

Furthermore, the present invention provides a resist composition which contains at least the above-mentioned polymer of the present invention as a base resin.

The compound of the present invention can be obtained at high yield and easily, and the resist composition which contains as a base resin the polymer comprising the above-mentioned compound as a repeating unit is excellent in etching resistance, an adhesion property with a substrate, and affinity with a developer, and has high sensitivity and high resolving power. Furthermore, swelling at the time of development is small. Accordingly, it is highly practical, and is very effective as the resist composition in the photolithography using a high-energy beam such as ArF excimer laser light, KrF excimer laser light and the like as a light source.

In this case, it is desirable that the resist composition of the present invention is a chemically amplified resist composition which further contains an organic solvent and an acid generating agent.

As described above, if the polymer comprising as the repeating unit the above-mentioned compound is used as a base resin, and further an organic solvent and an acid generating agent is blended therewith, it can be the chemically amplified resist composition with a very high sensitivity, which is very useful as a highly sensitive resist composition demanded in recent years.

In this case, the resist composition of the present invention can further contain a dissolution controlling agent.

As described above, if a dissolution controlling agent is blended in the resist composition, the difference of the resolution power of the exposed part and the non-exposed part can be further improved.

Moreover, the resist composition of the present invention may further contain one or more of a basic compound and an acetylene alcohol derivative and a surfactant.

A diffusion rate of the acid in the resist film can be suppressed and a resolution can be further improved by adding a basic compound, and a preservation stability of the resist composition can be further improved by adding an acetylene alcohol derivative, and an application property of the resist composition can be further improved or controlled by adding a surfactant.

Such a resist composition of the present invention can be used in a patterning process on a semiconductor substrate, a mask substrate, or the like, comprising, at least, a step of applying the resist composition on the substrate, a step of exposing the applied resist composition with a high-energy beam after heat-treatment, and a step of developing the exposed resist composition using a developer.

Of course, it may be developed after heat treatment after exposure, and various other steps such as an etching step, a resist removing step, a washing step or the like, may be performed.

The resist composition which uses the polymer comprising as the repeating unit the compound of the present invention as the base resin is useful for a fine processing, since it is sensitive to high-energy beams, such as an electron ray and far ultraviolet rays, is excellent in sensitivity, a resolving power, and etching resistance, and since swelling at the time of development is small. Especially, since absorption thereof at an exposure wavelength of an ArF excimer laser and a KrF excimer laser is small, a pattern which is fine and perpendicular to a substrate can be easily formed.

DESCRIPTION OF THE INVENTION AND EMBODIMENT

Hereafter, the present invention will be explained, but the present invention is not limited thereto.

The inventors of the present invention have studied further to obtain a resist composition especially for photolithography using a high energy beam such as ArF or KrF eximer laser light as a light source which is excellent in etching resistance, an adhesion property with a substrate, and an affinity with a developer, and has a high sensitivity and a high resolving power, and has a small swelling of the resist composition at the time of development, and found that a compound represented by the following general formula (1) (hereafter referred to as the tetrahydrofuran compound) can be easily obtained at high yield, and a polymer comprising as a repeating unit the tetrahydrofuran compound (1) has a high transparency at an exposure wavelength of an excimer laser, and a resist composition using it as a base resin has a high sensitivity and a high resolving power, and is excellent in adhesion property with a substrate and etching resistance, that swelling at the time of development is small, and that the resist composition is quite effective for an ultra fine processing, and thereby the present invention has been completed.

Namely, the compound according to the present invention is a compound represented by the following general formula (1).

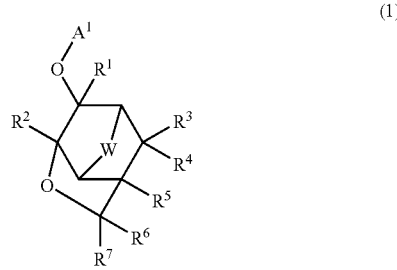

(1)

(In the formula, $A^1$ represents a polymerizable functional group which has a carbon-carbon double bond at least, $R^1$ and $R^2$ independently represent a hydrogen atom, or a linear, branched or cyclic monovalent hydrocarbon group having 1–10 carbon atoms, $R^3$–$R^7$ independently represent a hydrogen atom, or a linear, branched or cyclic monovalent hydrocarbon group having 1–10 carbon atoms which may contain a hetero atom, or two of $R^3$–$R^7$ may bond to each other and form an aliphatic hydrocarbon ring, and W represents any one of $CH_2$, an oxygen atom and a sulfur atom.)

Specific examples of $A^1$ may include: a vinyl group, an allyl group, a 1-propenyl group, an isopropenyl group, an acryloyl group, a methacryloyl group, a 2-(trifluoro methyl) acryloyl group, a norbornene carbonyl group, and a tetra cyclo[$4.4.0.1^{2,5}.1^{7,10}$]dodecene carbonyl group, and the like. Specific examples of $R^1$ and $R^2$ may include: methyl, ethyl, n-propyl, isopropyl, n-butyl, sec-butyl, tert-butyl, tert-amyl, n-pentyl, n-hexyl, cyclopentyl, cyclohexyl, bicyclo[2.2.1]heptyl, bicyclo[2.2.2]octyl, bicyclo[3.3.1]nonyl, bicyclo[4.4.0]decanyl, adamantyl and the like. Specific examples of $R^3$–$R^7$ may include: the same groups as explained in the above $R^1$ and $R^2$, and hydroxy methyl, hydroxy ethyl, methoxy methyl, methoxy ethyl, methoxy ethoxy methyl, methoxycarbonyl, formyloxy, acetoxy, pivaloyl, cyclohexyloxy, formyloxy methyl, acetoxy methyl, pivaloyloxy methyl, cyclohexyloxy methyl, and the like. Two of $R^3$–$R^7$ may bond to each other, to form an aliphatic hydrocarbon ring having preferably 3–20 carbon atoms, especially 4–15 carbon atoms. Specific examples as the ring formed as a result that two of $R^3$–$R^7$ bond to each other may include: cyclopropane, cyclobutane, cyclopentane, cyclohexane, bicyclo[2.2.1]heptane, bicyclo[2.2.2]octane, bicyclo[3.3.1]nonane, bicyclo[4.4.0]decane, adamantane, and the like.

It is desirable that the compound represented by the above-mentioned general formula (1) is the compound represented by the following general formula (2).

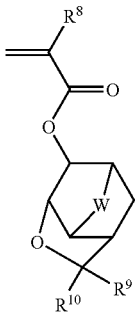

(2)

(In the formula, W is the same as that explained above. $R^8$ represents a hydrogen atom, a methyl group, or a trifluoro methyl group. $R^9$ and $R^{10}$ independently represent a hydrogen atom or a linear, branched, or cyclic monovalent hydrocarbon group having 1–10 carbon atoms. Alternatively, $R^9$ and $R^{10}$ may bond to each other to form an aliphatic-hydrocarbon ring together with the carbon atom to which they bond.)

Specific example of $R^9$ and $R^{10}$ may include: the similar groups to those explained in the above-mentioned $R^1$ and $R^2$. $R^9$ and $R^{10}$ may bond to each other to form an aliphatic-hydrocarbon ring having preferably 3–20 carbon atoms, especially 4–15 carbon atoms together with the carbon atom to which they bond. Specific examples of the ring formed as a result that $R^9$ and $R^{10}$ bond to each other may include: cyclopropane, cyclobutane, cyclopentane, cyclohexane, bicyclo[2.2.1]heptane, bicyclo[2.2.2]octane, bicyclo[3.3.1]nonane, bicyclo[4.4.0]decane, adamantane, and the like.

Moreover, it is desirable that the compound represented by the above-mentioned general formula (1) is the compound represented by the following general formula (3).

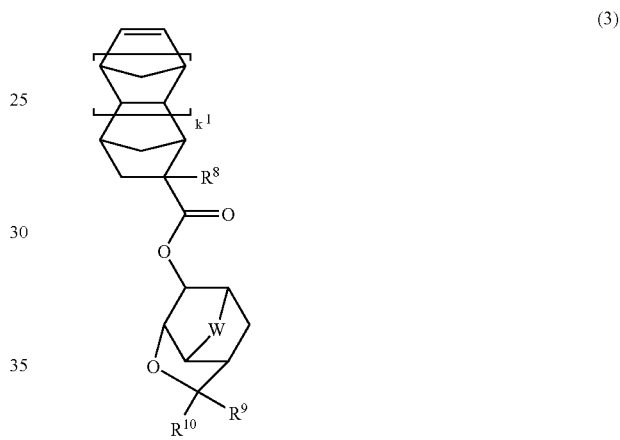

(3)

wherein $R^8$–$R^{10}$ and W are the same as explained above, $k^1$ is 0 or 1.

Specific examples of the compounds represented by the above-mentioned general formulae (1)–(3) will be listed below. In the following formulae, Me represents a methyl group, and Ac represents an acetyl group.

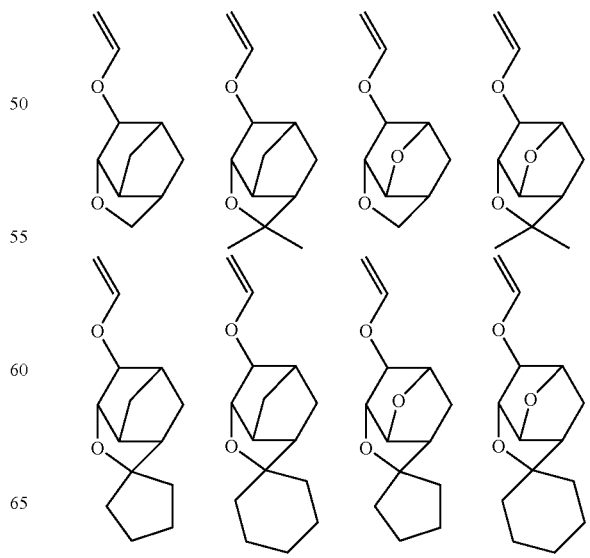

-continued
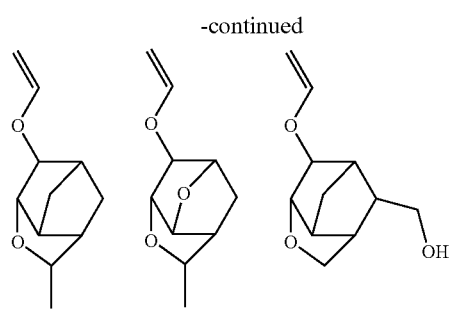
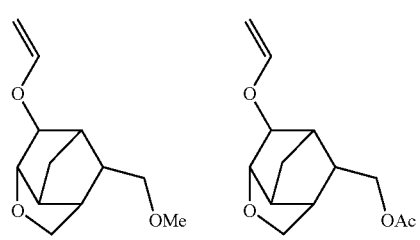
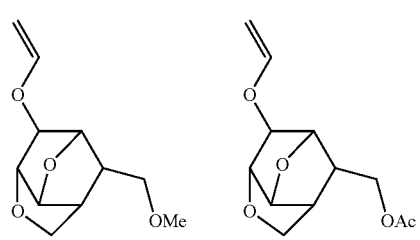
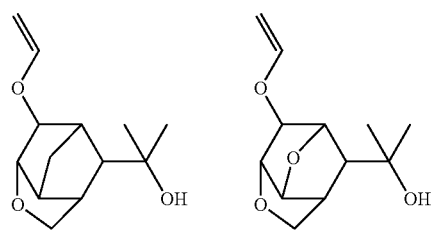
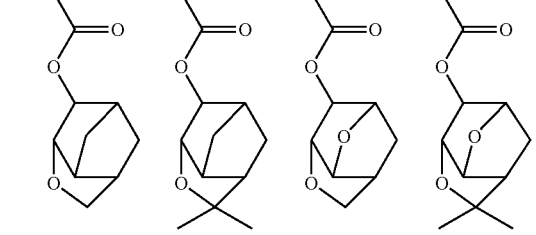
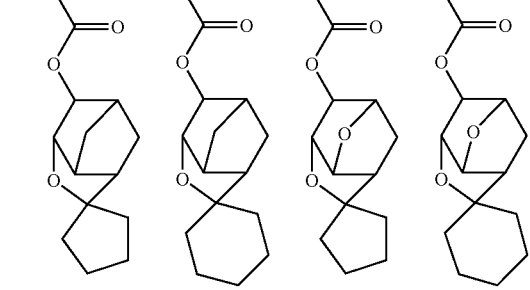
-continued
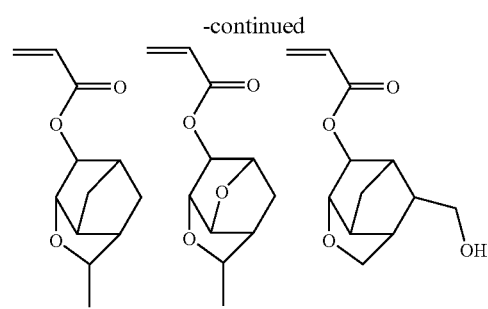
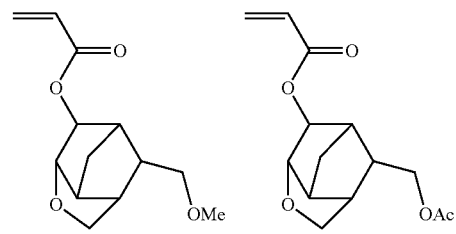
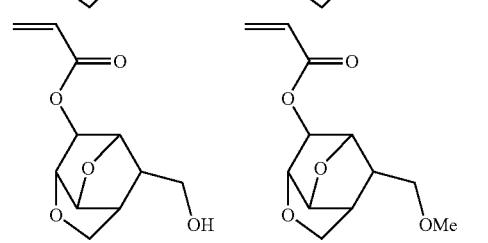
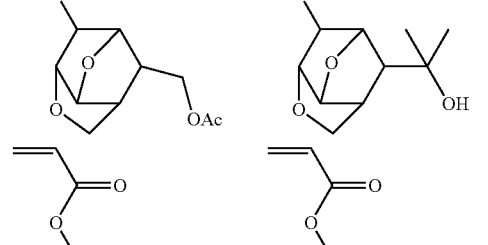
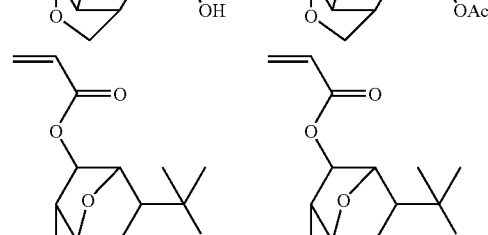
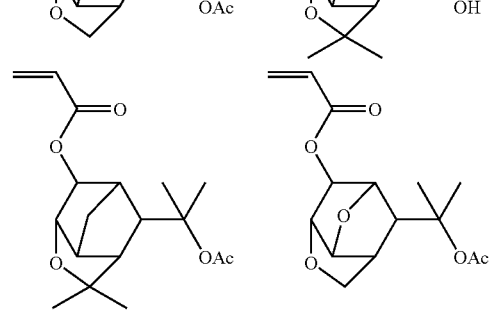

-continued
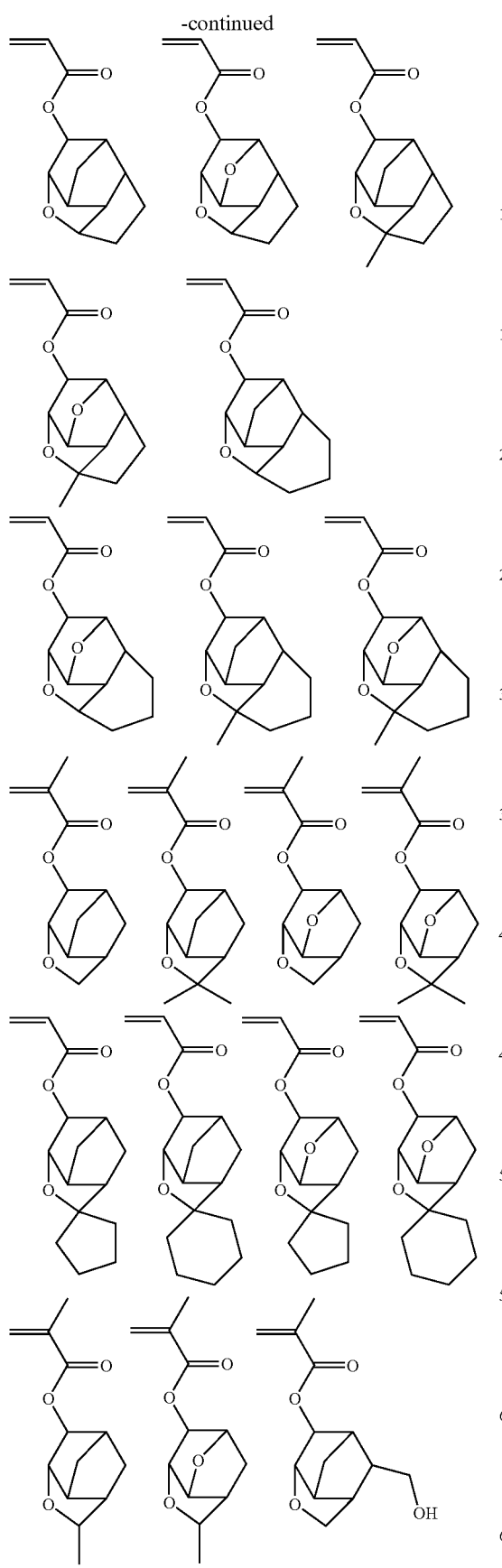
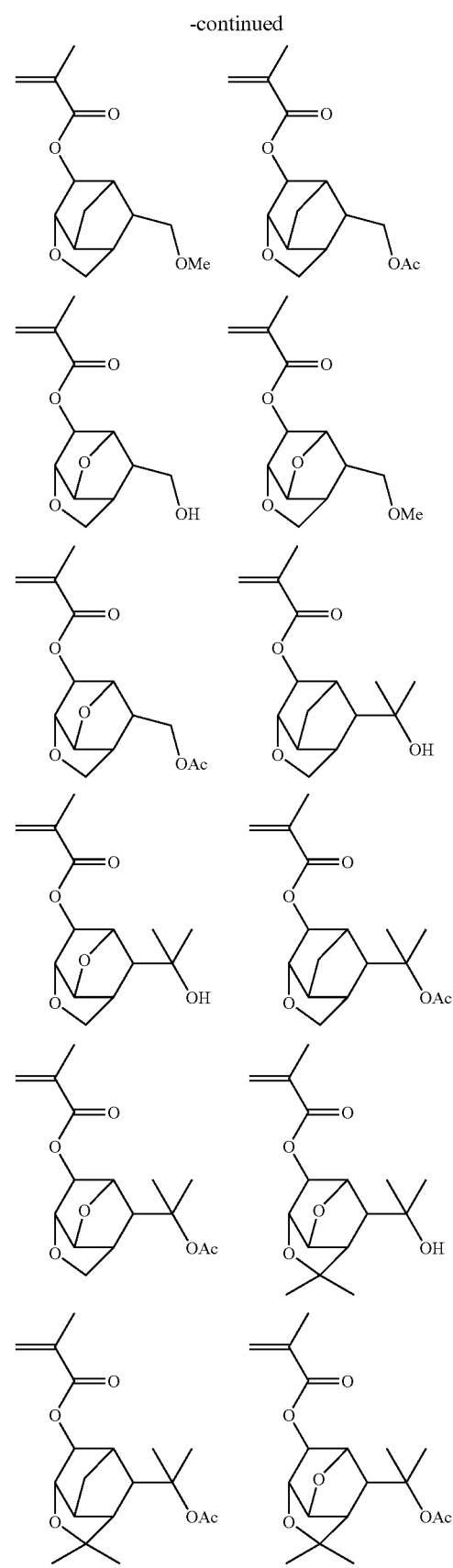

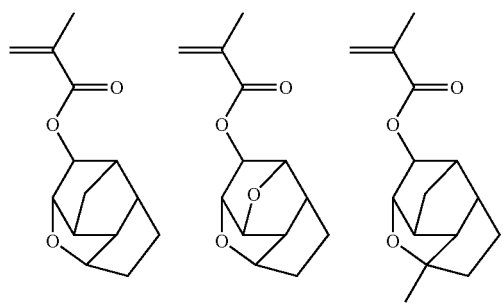
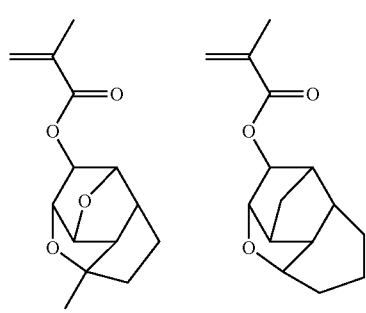
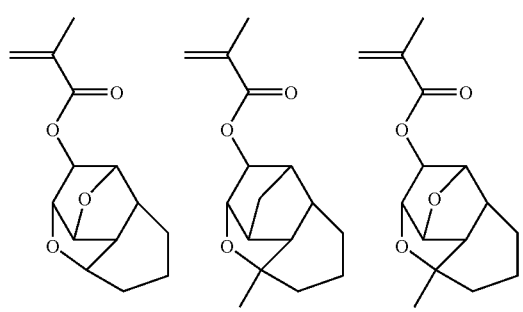
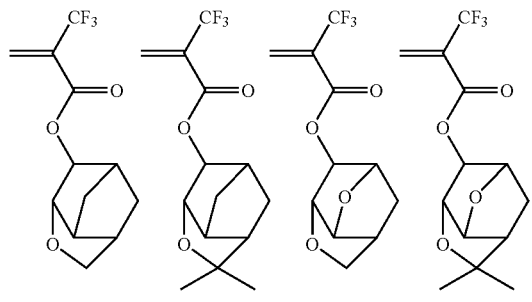
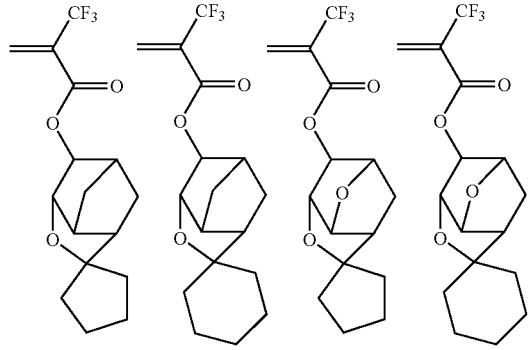
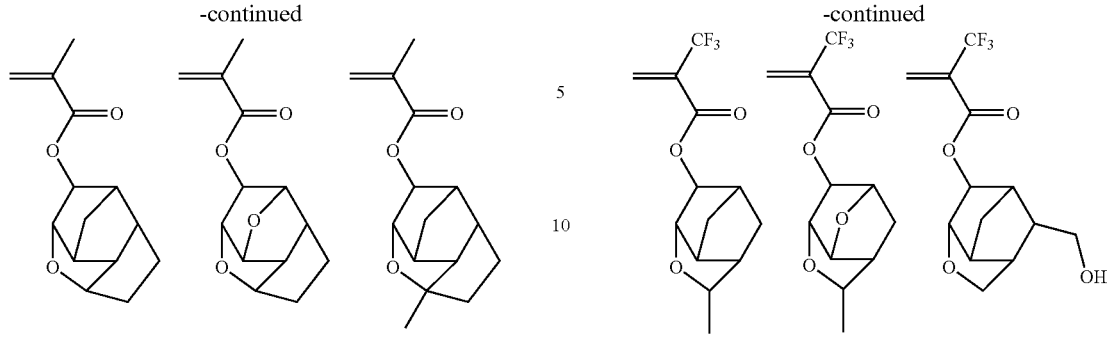
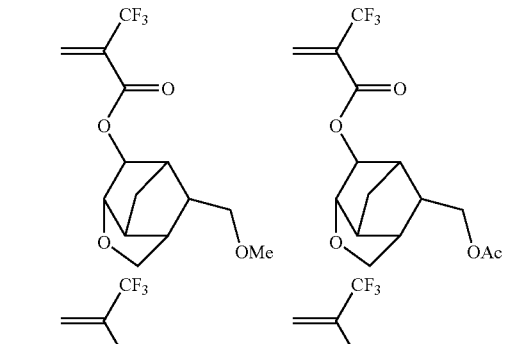
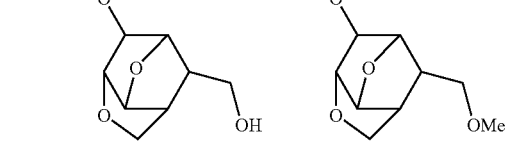
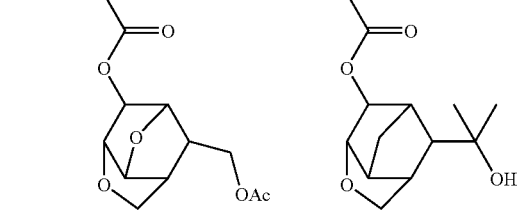
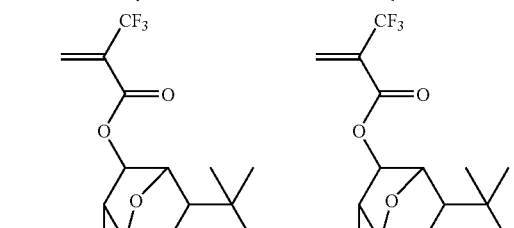

-continued
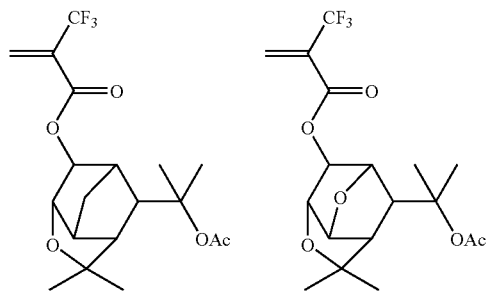
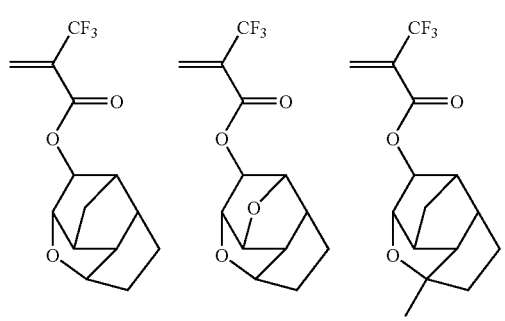
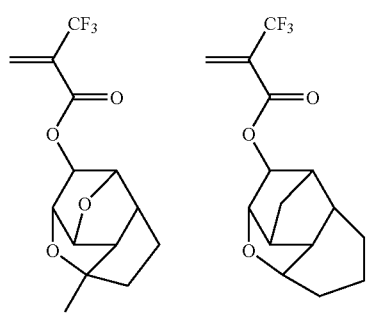
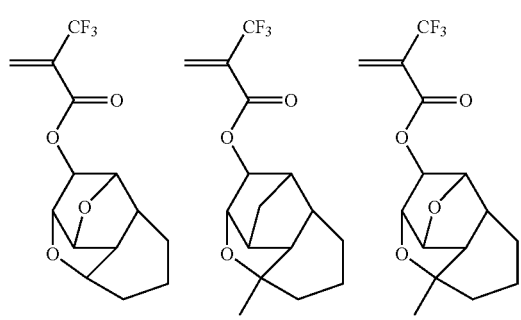
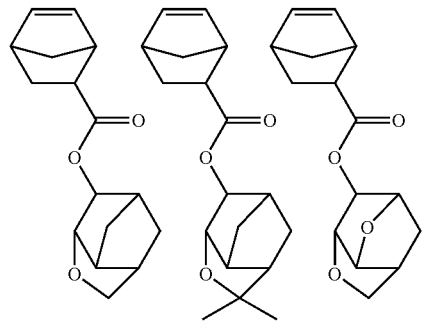
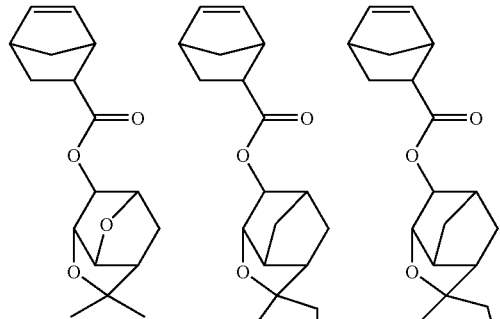
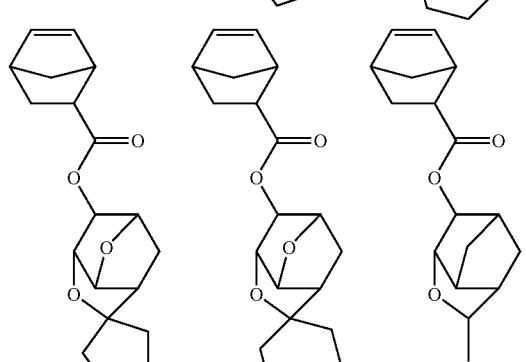
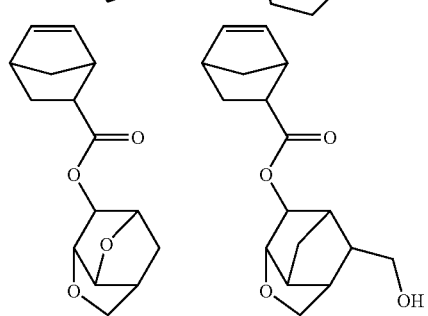
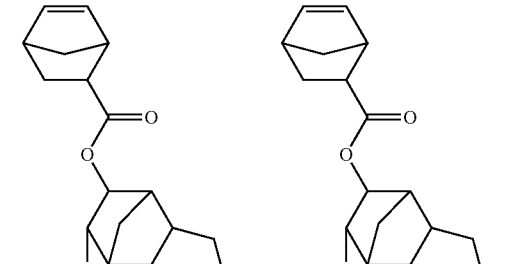
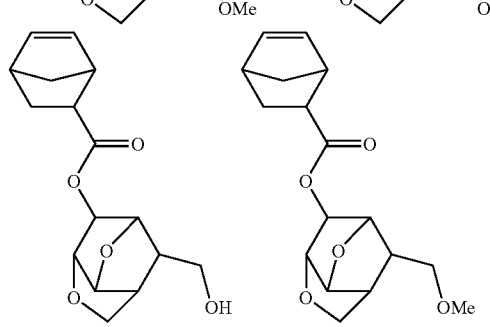

-continued

-continued

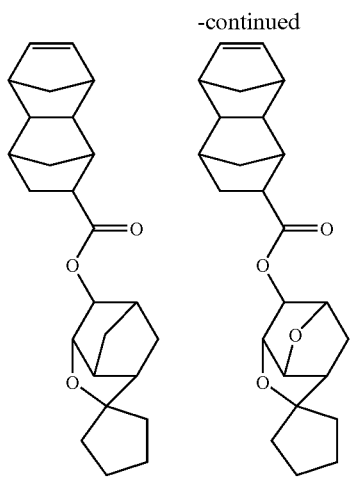

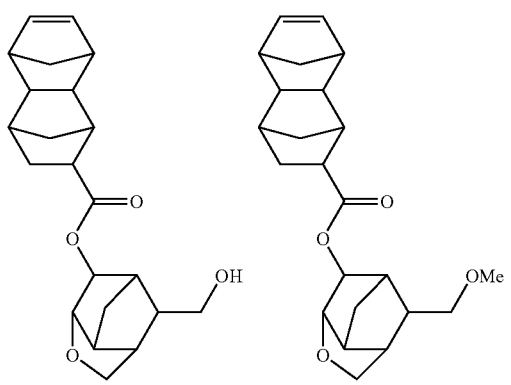

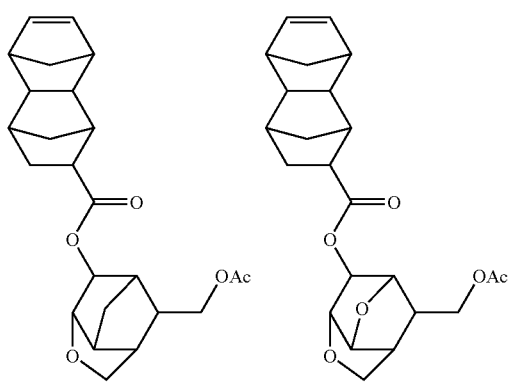

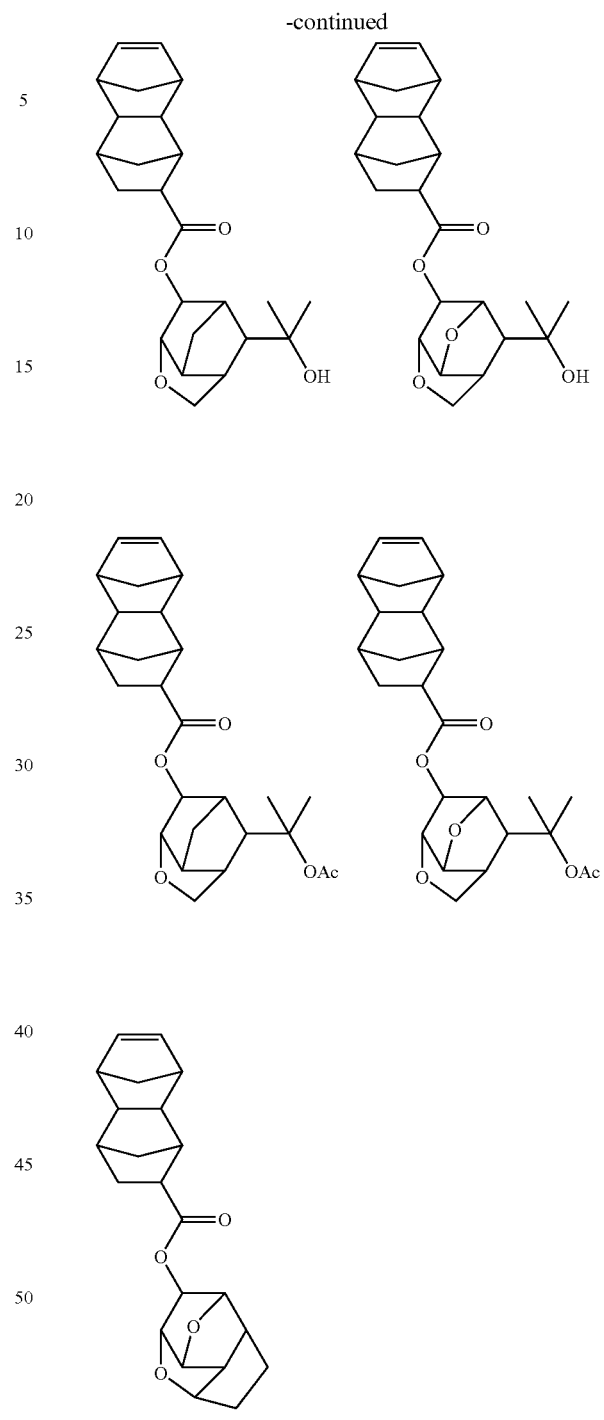

The compound represented by the above-mentioned general formula (1) of the present invention can be obtained by, for example, producing an intermediate alcohol compound of the following general formula (10) by the methods i)–iv) explained below as the first step, and etherifying or esterifying a hydroxyl group of the intermediate alcohol compound of the following general formula (10) by the method v) explained below as the second step, as shown in the following reaction formula. But the method is not limited thereto.

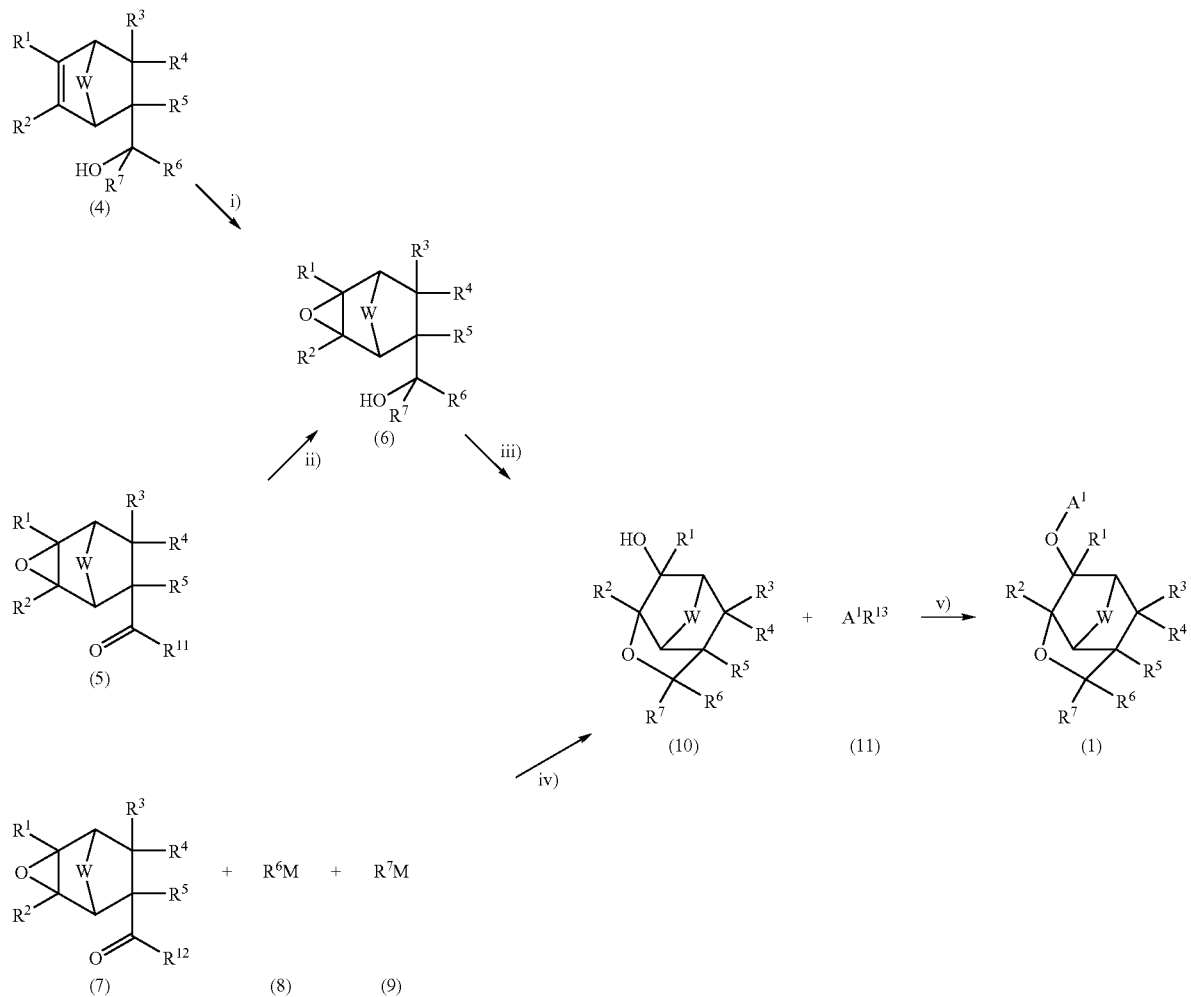

(In the formulae, wherein $A^1$, W, and $R^1$–$R^7$ are the same as explained above. $R^{11}$ represents a hydrogen atom, a hydroxyl group, or the alkyl group of $R^6$ or $R^7$. $R^{12}$ represents a halogen atom or —$OR^{14}$. $R^{13}$ represents a halogen atom, a hydroxyl group, an alkylsulfonyloxy group, or an arylsulfonyloxy group. $R^{14}$ represents a methyl group or an ethyl group. M represents Li, Na, K, MgP, or ZnP, and P represents a halogen atom.)

First, a method of preparing the compound represented by the above-mentioned general formula (10) (hereinafter referred to as an intermediate alcohol compound) as the first step will be explained in detail below.

1) In the first step, the compound represented by the above-mentioned general formula (6) (hereinafter referred to as an epoxy alcohol compound) is obtained from the compound represented by the above-mentioned general formula (4) or the above-mentioned general formula (5) according to the methods i) or ii), and then an intermediate alcohol compound (10) can be obtained according to etherification accompanied by cleavage of an epoxy group according to the method of iii).

The methods i) –iii) will be explained below.

i) An epoxy alcohol compound (6) can be obtained by oxidizing a carbon-carbon double bond of the compound of the above-mentioned general formula (4) (hereinafter referred to as an alcohol compound).

Specific examples of the oxidizing agent to be used may include: m-chloro perbenzoic acid, performic acid, peracetic acid, hydrogen peroxide, oxygen, and the like. The amount of the oxidizing agent to be used is preferably 0.5–4.0 mols, especially 1.0–2.5 mols to one mol of the alcohol compound (4). Preferable examples of a solvent may include: water, methylene chloride or ethers such as tetrahydrofuran, diethyl ether, di-n-butyl ether, 1,4-dioxane and the like, hydrocarbons such as n-hexane, n-heptane, benzene, toluene, xylene, cumene and the like, and these solvents can be used alone or as a mixture thereof. A reaction temperature and a reaction time are varied depending on conditions. However, for example, when using a performic acid as an oxidizing agent, it is performed at a reaction temperature of 10–80° C., preferably at 30–50° C. Although it is desirable in respect of yield to define a reaction time by monitoring a reaction by gas chromatography (GC) or silica gel thin-layer chromatography (TLC) to complete the reaction, it is usually about 0.5–15 hours. The epoxy alcohol compound (6) can be obtained from the reaction mixture by an usual aqueous work-up, and if necessary, it can be purified according to a conventional method such as distillation, chromatography or the like.

ii) The epoxy alcohol compound (6) can be produced by a reduction reaction of the compound represented by the above-mentioned general formula (5) (hereafter referred to as the epoxy compound having a carbonyl group).

Specific example of the reducing agent to be used may include: complex hydride such as sodium borohydride, lithium borohydride, potassium borohydride, calcium borohydride, aluminum sodium hydride, lithium aluminum hydride, lithium triethyl borohydride, lithium tri-s-butyl borohydride, potassium tri-s-butyl borohydride and the like, and alkoxy or alkyl derivatives thereof. The amount of the reducing agent to be used is desirably 0.3–4.0 mols, and especially 0.5–2.0 mols to one mol of the epoxy-compound (5) which has a carbonyl group. Preferable examples of a solvent may include: water or ethers such as tetrahydrofuran, diethyl ether, di-n-butylether, 1,4-dioxane and the like, hydrocarbons such as n-hexane, n-heptane, benzene, toluene, xylene, cumene and the like, alcohols such as methanol, ethanol, isopropyl alcohol, tert-butyl alcohol and the like, aprotic polar solvents, such as dimethyl sulfoxide (DMSO), N,N-dimethylformamide (DMF), acetonitrile and the like. These solvents can be used alone or as a mixture. A reaction temperature and reaction time are varied depending on conditions. However, for example, when using sodium boron hydride as a reducing agent, it is performed at a reaction temperature of −20 to 80° C., preferably at −10 to 40° C. Although it is desirable in respect of yield to define a reaction time by monitoring a reaction by gas chromatography (GC) or silica gel thin-layer chromatography (TLC) to complete the reaction, it is usually about 0.5–5 hours. The epoxy alcohol compound (6) can be obtained from the reaction mixture by a usual aqueous work-up, and if necessary, it can be purified according to a conventional method such as distillation, chromatography or the like.

iii) The intermediate alcohol compound (10) can be prepared by etherification accompanied by cleavage of an epoxy group of the epoxy alcohol compound (6) obtained by the above-mentioned method i) or ii). A good result will be obtained when this reaction is performed using an acid or salts thereof.

Examples of the acid to be used may include: inorganic acids such as hydrochloric acid, hydrobromic acid, sulfuric acid, nitric acid, perchloric acid, and phosphoric acid or salts thereof, organic acids such as formic acid, acetic acid, oxalic acid, benzoic acid, p-toluenesulfonic acid, benzenesulfonic acid or salts thereof, Lewis acids such as a cation exchange resin, lithium chloride, aluminum chloride, zinc chloride, zinc iodide, titanium tetrachloride, boron trifluoride, and the like. In this case, an amount the acid to be used is preferably 0.01–10 mols, especially 0.01 to 0.5 mols to one mole of the epoxy alcohol compound (6). Preferable examples of the solvent may include: ethers such as tetrahydrofuran, diethyl ether, di-n-butyl ether, 1,4-dioxane and the like, hydrocarbons such as n-hexane, n-heptane, benzene, toluene, xylene, cumene and the like. These solvents can be used alone or as a mixture. Although the reaction temperature and the reaction time are varied depending on conditions, for example, when using a sulfuric acid as an acid, the reaction temperature is 0–100° C., preferably 20–60° C. Although it is desirable in respect of yield to define a reaction time by monitoring the reaction with gas chromatography (GC) or silica gel thin-layer chromatography (TLC) to complete a reaction, it is usually about 0.5–10 hours. The intermediate alcohol compound (10) can be obtained from the reaction mixture by a usual aqueous work-up, and if necessary, it can be purified according to a conventional method, such as distillation, chromatography or the like.

2) As the second method, an intermediate alcohol compound (10) can be prepared by the following method iv).

iv) The intermediate alcohol compound (10) can be prepared by a nucleophilic-addition-reaction of the above-mentioned organometallic reagents (8) and (9) to a carbonyl group of the compound of the above-mentioned general formula (7) (hereinafter referred to as an epoxy ester compound) followed by an intramolecular cyclization by a nucleophilic attack to an epoxy group of the produced alkoxide.

An amount of the organometallic reagent of the above-mentioned general formula (8) and (9) to be used is desirably 2.0–5.0 mols, especially 2.0–3.0 mols to one mol of the epoxy ester compound (7). Examples of the solvent may include, ethers such as tetrahydrofuran, diethyl ether, di-n-butyl ether, 1,4-dioxane and the like, hydrocarbons such as the n-hexane, n-heptane, benzene, toluene, xylene, cumene and the like. These solvents can be used alone or as a mixture. Although the reaction temperature and the reaction time are varied depending on conditions, for example, when the Grignard reagent (M is MgP in the above-mentioned general formulae (8) and (9)) is used as the organometallic reagent, the reaction temperature is −20 to 100° C., preferably 0 to 50° C. Although it is desirable in respect of yield to define the reaction time by monitoring the reaction by gas chromatography (GC) or silica gel thin-layer chromatography (TLC) to complete the reaction, it is usually about 0.5–5 hours. The intermediate alcohol compound (10) can be obtained from the reaction mixture by a usual aqueous work-up, and if necessary, it can be purified according to a conventional method, such as distillation, chromatography or the like.

Next, a method for preparing the compound represented by the above-mentioned general formula (1) as the second step will be explained in detail below.

v) The second step is etherification or esterification of the intermediate alcohol compound (10) produced in the previous stage. The reaction progresses easily by a well-known method. However, for example, when the polymerizable functional group $A^1$ in the above-mentioned general formula (1) bonds via a ester bond, an esterification agent represented by the above-mentioned general formula (11) is preferably for example, an acid chloride (when $R^{13}$ is a chlorine atom in the above-mentioned general formula (11)), or a carboxylic acid (when $R^{13}$ is a hydroxyl group in the above-mentioned general formula (11)). When using an acid chloride, it is preferable to add an intermediate alcohol compound, a corresponding acid chloride such as methacrylic-acid chloride, norbornene carboxylic-acid chloride and the like, bases such as triethylamine, pyridine, 4-dimethyl amino pyridine and the like, sequentially or simultaneously, without a solvent or in a solvent such as methylene chloride, toluene, hexane and the like, with cooling or heating it, if needed. Moreover, when using a carboxylic acid, it is preferable to add an intermediate alcohol compound, a corresponding carboxylic acid such as a methacrylic acid, and a norbornene carboxylic acid or the like, an inorganic acid such as hydrochloric acid, sulfuric acid, nitric acid, perchloric acid or the like, an organic acid such as p-toluenesulfonic acid, benzenesulfonic acid or the like, in a solvent such as toluene and hexane, followed by heating, and removing the produced water, if necessary.

The present invention provides a polymer comprising at least the above-mentioned compound according to the present invention as the repeating unit.

The compound represented by the above-mentioned general formulae (1)–(3) as the repeating unit may be specifically the repeating unit represented by the general formulae (1a)–(1d).

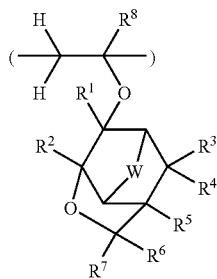

(1a)

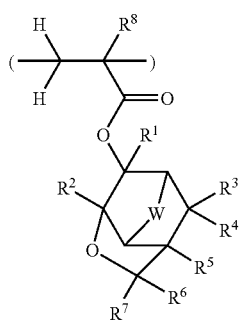

(1b)

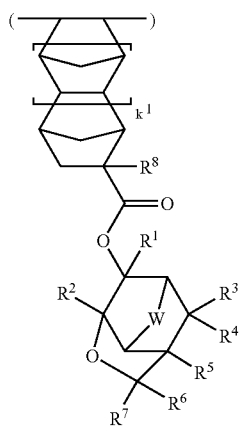

(1c)

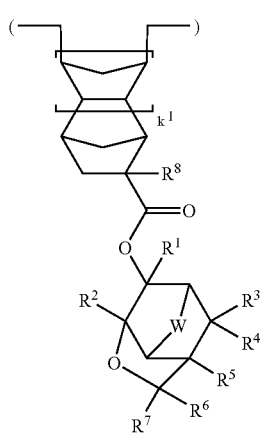

(1d)

(In the formulae, W, $R^1$–$R^8$ and $k^1$ are the same as explained above.)

Moreover, the polymer of the present invention comprises, in addition to the repeating unit of the compound represented in by the general formulae (1)–(3) such as the repeating unit represented by above-mentioned general formulae (1a)–(1d), repeating units obtained from other monomers containing a polymerizable double bond.

Specific examples of the repeating unit obtained from the monomer containing a polymerizable double bond may include those represented by the following general formulae (M1)–(M13).

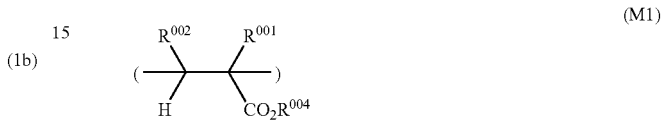
(M1)

(M2)

(M3)

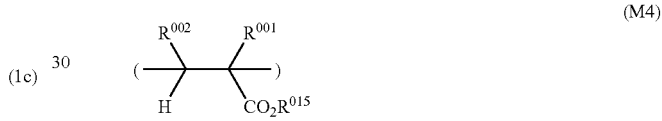
(M4)

(M5)

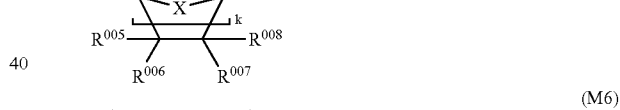
(M6)

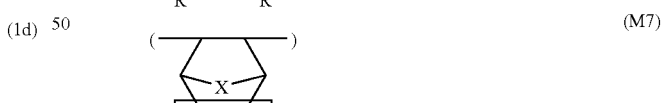
(M7)

(M8)

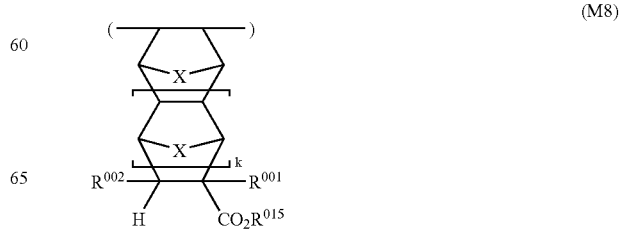

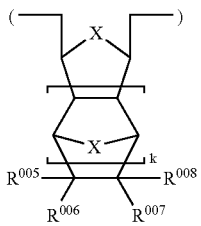
(M9)

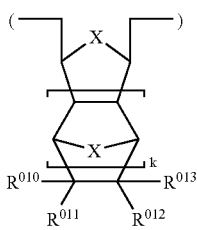
(M10)

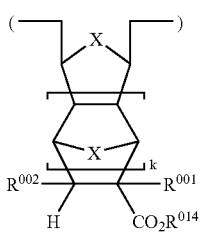
(M11)

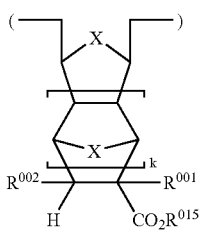
(M12)

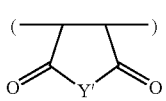
(M13)

(In the formulae, $R^{001}$ represents a hydrogen atom, a methyl group, or $CH_2CO_2R^{003}$. $R^{002}$ represents a hydrogen atom, a methyl group, or $CO_2R^{003}$. $R^{003}$ represents a linear, branched, or cyclic alkyl group having 1–15 carbon atoms. $R^{004}$ represents a hydrogen atom or a monovalent hydrocarbon group having 1–15 carbon numbers which contains a carboxyl group or a hydroxyl group. At least one of $R^{005}$–$R^{008}$ represents a monovalent hydrocarbon group having 1–15 carbon atoms which contains a carboxyl group or a hydroxyl group, and the remainder independently represents a hydrogen atom or a linear, branched, or cyclic alkyl group having 1–15 carbon atoms. $R^{005}$–$R^{008}$ may bond to each other and form a ring. In that case, at least one of $R^{005}$–$R^{008}$ represents a divalent hydrocarbon group having carbon atoms 1–15 which contains a carboxyl group or a hydroxyl group, and the remainder independently represents a single bond or a linear, branched, or cyclic alkylene group having 1–15 carbon atoms. $R^{009}$ represents a monovalent hydrocarbon group having 2–15 carbon atoms which contains at least one partial structure selected from an ether, an aldehyde, a ketone, an ester, a carbonate, an acid anhydride, an amide, and an imide. At least one of $R^{010}$–$R^{013}$ represents a monovalent hydrocarbon group having 2–15 carbon atoms which contains at least one partial structure selected from an ether, an aldehyde, a ketone, an ester, a carbonate, an acid anhydride, an amide, and an imide, and the remainder independently represents a hydrogen atom or a linear, branched, cyclic alkyl group having 1–15 carbon atoms. $R^{010}$–$R^{013}$ may bond to each other and form a ring. In that case, at least one of $R^{010}$–$R^{013}$ represents a divalent hydrocarbon group having 1–15 carbon atoms which contains at least one partial structure selected from an ether, an aldehyde, a ketone, an ester, a carbonate, an acid anhydride, an amide and an imide, and the remainder independently represents a single bond or a linear, branched, cyclic alkylene group having 1–15 carbon atoms. $R^{014}$ represents a polycyclic hydrocarbon group or an alkyl group which contains a polycyclic-hydrocarbon group having 7–15 carbon atoms. $R^{015}$ represents an acid unstable group. X represents $CH_2$, an oxygen atom, or a sulfur atom. Y' represents —O— or —(NR$^f$)—, and R$^f$ represents a hydrogen atom or a linear, branched or cyclic alkyl group having 1–15 carbon atoms, k is 0 or 1.)

$R^{001}$ represents a hydrogen atom, a methyl group, or $CH_2CO_2R^{003}$. Specific examples of $R^{003}$ will be explained later. $R^{002}$ represents a hydrogen atom, a methyl group, or $CO_2R^{003}$. $R^{003}$ represents a linear, branched or cyclic alkyl group having 1–15 carbon atoms. Specific examples thereof may include: a methyl group, an ethyl group, a propyl group, an isopropyl group, n-butyl, sec-butyl, tert-butyl, tert-amyl group, n-pentyl group, n-hexyl group, a cyclopentyl group, a cyclohexyl group, an ethyl cyclopentyl group, a butyl cyclopentyl group, an ethyl cyclohexyl group, a butyl cyclohexyl group, an adamantyl group, an ethyl adamantyl group, a butyl adamantyl group, and the like.

$R^{004}$ represents a hydrogen atom or a monovalent hydrocarbon group having 1–15 carbon atoms which contains a carboxyl group or a hydroxyl group. Specific examples thereof may include: a hydrogen atom, carboxyl ethyl, carboxyl butyl, carboxyl cyclopentyl, carboxyl cyclohexyl, carboxyl norbornyl, carboxyl adamantyl, hydroxy ethyl, hydroxy butyl, hydroxy cyclopentyl, hydroxy cyclohexyl, hydroxy norbornyl, hydroxy adamantyl, and the like.

At least one of $R^{005}$–$R^{008}$ represents a monovalent hydrocarbon group having 1–15 carbon atoms which contains a carboxyl group or a hydroxyl group, and the remainder independently represents a hydrogen atom or a linear, branched or cyclic alkyl group having 1–15 carbon atoms. Specific examples of the monovalent hydrocarbon group having 1–15 carbon atoms which contains a carboxyl group or a hydroxyl group may include: carboxyl, carboxyl methyl, carboxyl ethyl, carboxyl butyl, hydroxy methyl, hydroxy ethyl, hydroxy butyl, 2-carboxy ethoxy carbonyl, 4-carboxy butoxy carbonyl, 2-hydroxy ethoxy carbonyl, 4-hydroxy butoxy carbonyl, carboxyl cyclopentyloxy carbonyl, carboxyl cyclohexyloxy carbonyl, carboxyl norbornyloxy carbonyl, carboxyl adamantyloxy carbonyl, hydroxy cyclopentyloxy carbonyl, hydroxy cyclohexyloxy carbonyl, hydroxy norbornyloxy carbonyl, hydroxy adamantyloxy carbonyl, and the like. Specific examples of the linear, branched or cyclic alkyl group having 1–15 carbon atoms, may include: a methyl group, an ethyl group, a propyl group, an isopropyl group, n-butyl, sec-butyl, tert-butyl, tert-amyl group, n-pentyl group, n-hexyl group, a cyclopentyl group, a cyclohexyl group, an ethyl cyclopentyl group, a butyl cyclopentyl group, an ethyl cyclohexyl group, a butyl-cyclohexyl group, an adamantyl group, an ethyl adamantyl group, a butyl adamantyl group, and the like. $R^{005}$–$R^{008}$ may bond to each other and form a ring. In that case, at least one of $R^{005}$–$R^{008}$ represents a divalent hydrocarbon group having 1–15 carbon atoms which contains a carboxyl group or a hydroxyl group, and the remainder independently represents a single bond or a linear, branched or cyclic alkylene group having 1–15 carbon atoms. Specific examples of the divalent hydrocarbon group having 1–15 carbon atoms which contains a carboxyl group or a hydroxyl group may be those wherein one hydrogen atom is removed from those exemplified for the above-mentioned monovalent hydrocarbon group which contains a carboxyl group or a hydroxyl group and the like. Specific examples of a linear, branched or cyclic alkylene group having 1–15 carbon atoms may be those wherein one hydrogen atom is removed from those illustrated for the above-mentioned linear, branched or cyclic alkyl group having 1–15 carbon atoms.

$R^{009}$ represents a monovalent hydrocarbon group having 2–15 carbon atoms which contains at least one partial structure selected from an ether, an aldehyde, a ketone, an ester, a carbonate, an acid anhydride, an amide, an imide. Specific examples thereof may include: methoxy methyl, methoxy ethoxy methyl, 2-oxooxolane-3-yl, 2-oxooxolane-4-yl, 4,4-dimethyl-2-oxooxolane-3-yl, 4-methyl-2-oxooxane-4-yl, 2-oxo-1,3-dioxolane-4-yl methyl, 5-methyl-2-oxooxolane-5-yl, the following groups and the like.

which contains at least one partial structure selected from an ether, a ketone, an ester, a carbonate, an acid anhydride, an amide, and an imide may include: methoxy methyl, methoxy methoxy methyl, formyl, methyl carbonyl, formyloxy, acetoxy, pivaloyloxy, formyloxy methyl, acetoxy methyl, pivaloyloxy methyl, methoxycarbonyl, 2-oxo-oxolane-3-yloxy carbonyl, 4,4-dimethyl-2-oxo-oxolane-3-yloxy carbonyl, 4-methyl-2-oxo-oxane-4-yloxy carbonyl, 2-oxo-1,3-dioxolane-4-yl methyloxy carbonyl, 5-methyl-2-oxo-oxolane-5-yloxy carbonyl, the following groups, and the like.

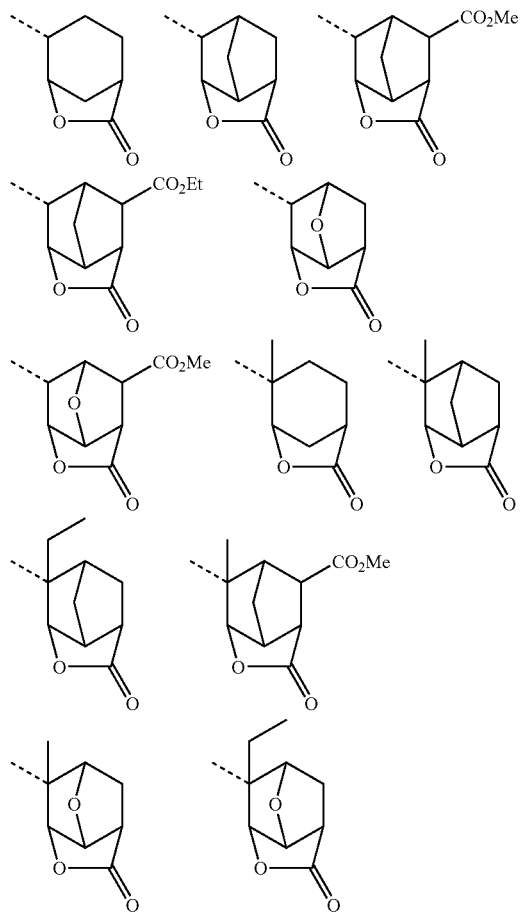

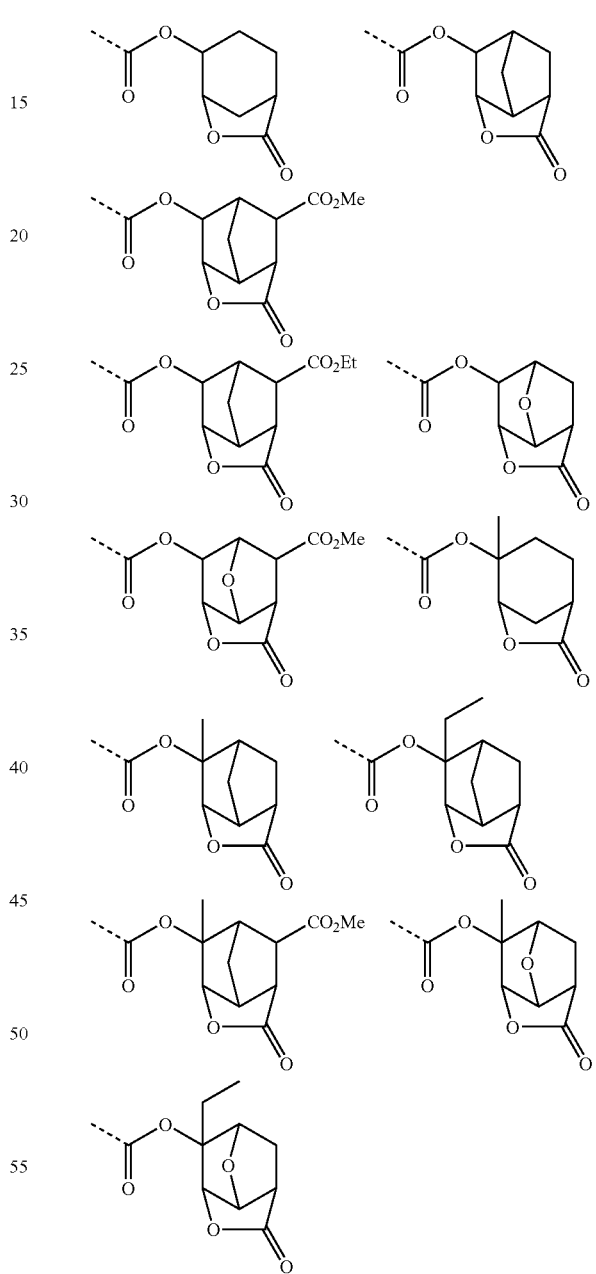

(In the formulae the chain line represents a bond (hereinafter it represents the same meaning). Me represents a methyl group, and Et represents an ethyl group.)

At least one of $R^{010}$–$R^{013}$ represents a monovalent hydrocarbon group having 2–15 carbon atoms which contains at least one partial structure selected from an ether, an aldehyde, a ketone, an ester, a carbonate, an acid anhydride, an amide and an imide, and the remainder independently represents a hydrogen atom or a linear, branched or cyclic alkyl group having 1–15 carbon atoms. Specific examples of a monovalent hydrocarbon group having 2–15 carbon atoms Specific examples of a linear, branched or cyclic alkyl group having 1–15 carbon atoms may be those explained for $R^{003}$. $R^{010}$–$R^{013}$ may bond to each other and form a ring. In that case, at least one of $R^{010}$–$R^{013}$ represents a divalent hydrocarbon group having 1–15 carbon atoms which contains at least one partial structure selected from an ether, an aldehyde, a ketone, an ester, a carbonate, an acid anhydride, an amide, and an imide, and the remainder independently represents a single bond or a linear, branched or cyclic alkylene group having 1–15 carbon atoms.

Specific examples of the divalent hydrocarbon group having 1–15 carbon atoms which contains at least one partial structure selected from an ether, an aldehyde, a ketone, an ester, a carbonate, an acid anhydride, an amide and an imide may include: 2-oxapropane-1,3-diyl, 1,1-dimethyl-2-oxapropane-1,3-diyl, 1-oxo-2-oxapropane-1,3-diyl, 1,3-dioxo-2-oxapropane-1,3-diyl, 1-oxo-2-oxabutane-1,4-diyl, 1,3-dioxo-2-oxabutane-1,4-diyl, and the like, and those wherein one hydrogen atom is removed from those exemplified for the above-mentioned monovalent hydrocarbon group having 1–15 carbon atoms which contains at least one partial structure selected from an ether, an aldehyde, a ketone, an ester, a carbonate, an acid anhydride, an amide, and an imide, and the like. Specific examples of the linear, branched or cyclic alkylene group having 1–15 carbon atoms may be those wherein one hydrogen atom is removed from those exemplified for $R^{003}$ and the like.

$R^{014}$ represents a polycyclic-hydrocarbon group or an alkyl group which contains a polycyclic-hydrocarbon group having 7–15 carbon atoms. Specific examples thereof may include: norbornyl, bicyclo[3.3.1]nonyl, tricyclo[5.2.1.0$^{2,6}$] decyl, adamantyl, ethyl adamantyl, butyl adamantyl, norbornyl methyl, adamantyl methyl and the like.

$R^{015}$ represents an acid unstable group, specifically represents a group represented by the following general formulae (L1)–(L4), and tertiary alkyl group having 4–20, preferably 4–15 carbon atoms, a trialkylsilyl group wherein each of the alkyl groups has 1–6 carbon atoms, an oxoalkyl group having 4–20 carbon atoms, and the like.

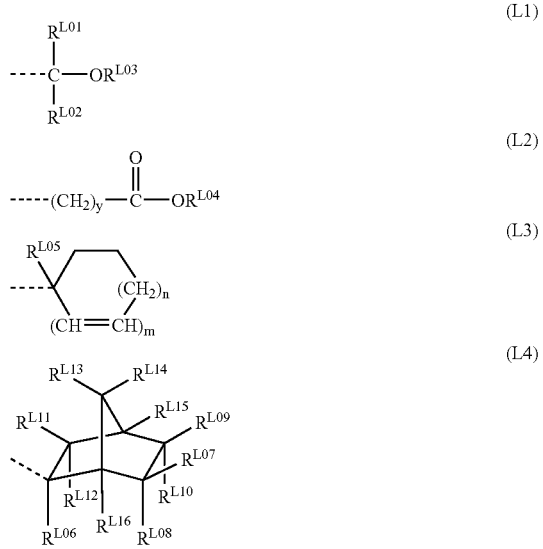

In the formulae, $R^{L01}$ and $R^{L02}$ represent a hydrogen atom or a linear, branched or cyclic alkyl group having 1–18, preferably 1–10 carbon atoms. Specific examples thereof may include: a methyl group, an ethyl group, a propyl group, an isopropyl group, n-butyl group, sec-butyl group, tert-butyl group, a cyclopentyl group, a cyclohexyl group, 2-ethylhexyl group, n-octyl group, and the like. $R^{L03}$ represents a monovalent hydrocarbon group having 1–18, preferably 1–10 carbon atoms which may contain a hetero atom such as an oxygen atom and the like. Examples thereof may include: a linear, branched or cyclic alkyl group, and those wherein a part of hydrogen atoms is substituted with a hydroxyl group, an alkoxy group, an oxo group, an amino group, an alkyl amino group, and the like. Specific examples thereof may be the following substituted alkyl groups and the like.

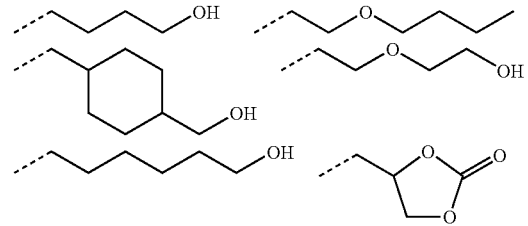

$R^{L01}$ and $R^{L02}$, $R^{L01}$ and $R^{L03}$, and $R^{L02}$ and $R^{L03}$ may bond to each other and form a ring. In the case that the ring is formed, each of $R^{L01}$, $R^{L02}$ and $R^{L03}$ represents a linear, branched or cyclic alkylene group having 1–18, preferably 1–10 carbon atoms.

$R^{L04}$ represents tertiary alkyl group having 4–20, preferably 4–15 carbon atoms, a trialkyl silyl group wherein each of the alkyl groups has 1–6 carbon atoms, an oxoalkyl group having 4–20 carbon atoms, or the group represented by the above-mentioned general formula (L1). Specific examples of the tertiary alkyl group may include: tert-butyl group, tert-amyl group, 1,1-diethyl propyl group, 2-cyclopentyl propane-2-yl group, 2-cyclohexyl propane-2-yl group, 2-(bicyclo[2.2.1]heptane-2-yl) propane-2-yl group, 2-(adamantane-1-yl) propane-2-yl group, 1-ethyl cyclopentyl group, 1-butylcyclopentyl group, 1-ethyl cyclohexyl group, 1-butylcyclohexyl group, 1-ethyl-2-cyclopentenyl group, 1-ethyl-2-cyclohexenyl group, 2-methyl-2-adamantyl group, 2-ethyl-2-adamantyl group, and the like. Specific examples of the trialkyl silyl group may include: a trimethylsilyl group, a triethylsilyl group, a dimethyl-tert-butylsilyl group, and the like. Specific examples of the oxo-alkyl group may include: 3-oxo-cyclohexyl group, 4-methyl-2-oxooxane-4-yl group, 5-methyl 2-oxooxolane-5-yl group, and the like. y is an integer of 0–6.

$R^{L05}$ represents a monovalent hydrocarbon group having 1–8 carbon atoms which may contain a hetero atom, or an aryl group having 6–20 carbon atoms which may be substituted. Specific examples of the monovalent hydrocarbon group which may contain a hetero atom may include: a linear, branched or cyclic alkyl group such as a methyl group, an ethyl group, a propyl group, an isopropyl group, n-butyl group, sec-butyl group, tert-butyl, tert-amyl group, n-pentyl group, n-hexyl group, a cyclopentyl group, a cyclohexyl group and the like, those wherein a part of hydrogen atoms in the above groups is substituted with a hydroxyl group, an alkoxy group, a carboxyl group, an alkoxy carbonyl group, an oxo group, an amino group, an alkyl amino group, a cyano group, a sulfhydryl group, an alkylthio group, a sulfo group, or the like, or those wherein —CH$_2$— which constitutes the above groups is substituted with an oxygen atom. Examples of the aryl group which may be substituted may include: a phenyl group, a methyl phenyl group, a naphthyl group, an anthryl group, a phenanthryl group, a pyrenyl group, and the like. m is 0 or 1, and n is 0, 1, 2, or 3, and m and n satisfy the formula: 2m+n=2 or 3.

$R^{L06}$ represents a monovalent hydrocarbon group having 1–8 carbon atoms which may contain a hetero atom, or an aryl group having 6–20 carbon atoms which may be substituted, and specifically represents the same groups as $R^{L05}$ or the like.

$R^{L07}$ to $R^{L16}$ independently represent a hydrogen atom or a monovalent hydrocarbon group having 1–15 carbon atoms which may contain a hetero atom. Specific examples thereof may include: a linear, branched or cyclic alkyl group such as a methyl group, an ethyl group, a propyl group, an isopropyl group, n-butyl group, sec-butyl group, tert-butyl group, tert-amyl group, n-pentyl group, n-hexyl group, n-octyl group, n-nonyl group, n-decyl group, a cyclopentyl group, a cyclohexyl group, a cyclopentyl methyl group, a cyclopentyl ethyl group, cyclopentyl butyl group, a cyclohexyl methyl group, a cyclohexyl ethyl group, a cyclohexyl butyl group and the like, those wherein a part of hydrogen atoms in the above groups is substituted with a hydroxyl group, an alkoxy group, a carboxyl group, an alkoxy carbonyl group, an oxo group, an amino group, an alkyl amino group, a cyano group, a mercapto group, an alkylthio group, a sulfo group, and the like. $R^{L07}$ to $R^{L16}$ may bond to each other, and form a ring (for example, $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$ and the like). In this case, they represent a divalent hydrocarbon group having 1–15 carbon atoms which may contain a hetero atom, and specifically those wherein one hydrogen atom is removed from those exemplified as for the above-mentioned monovalent hydrocarbon group can be exemplified. Moreover, the groups among $R^{L07}$ to $R^{L16}$ each binding to adjacent carbon atoms may bond to each other without any groups between them, and form a double bond (for example, $R^{L07}$ and $R^{L09}$, $R^{L09}$ and $R^{L15}$, $R^{L13}$ and $R^{L15}$ and the like).

Specific examples of a linear or branched group among the acid unstable groups represented by the above-mentioned formula (L1) may include the following groups.

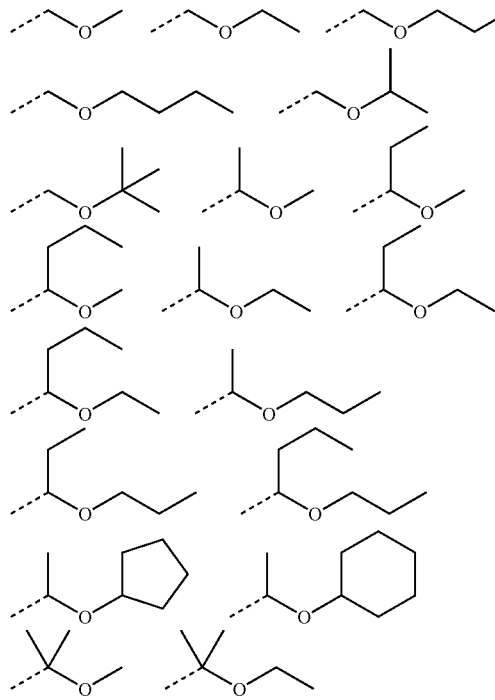

Specific examples of a cyclic group among the acid unstable groups represented by the above-mentioned formula (L1) may include: a tetrahydrofuran-2-yl group, 2-methyl tetrahydrofuran-2-yl group, tetrahydropyran-2-yl group, 2-methyl tetrahydropyran-2-yl group, and the like.

Specific examples of the acid unstable group represented by the above-mentioned formula (L2) may include: tert-butoxy carbonyl group, tert-butoxy carbonyl methyl group, tert-amyloxy carbonyl group, tert-amyloxy carbonyl methyl group, 1,1-diethyl propyl oxy-carbonyl group, 1,1-diethyl propyloxy carbonyl methyl group, 1-ethylcyclopentyl oxy-carbonyl group, 1-ethylcyclopentyloxy-carbonyl methyl group, 1-ethyl-2-cyclopentenyloxy-carbonyl group, 1-ethyl-2-cyclopentenyloxy-carbonyl methyl group, 1-ethoxy ethoxy carbonyl methyl group, 2-tetrahydro pyranyl oxy-carbonyl methyl group, 2-tetrahydrofuranyl oxy-carbonyl methyl group, and the like.

Specific examples of the acid unstable group represented by the above-mentioned formula (L3) may include: 1-methyl cyclopentyl, 1-ethyl cyclopentyl, 1-n-propyl cyclopentyl, 1-isopropyl cyclopentyl, 1-n-butylcyclopentyl, 1-sec-butylcyclopentyl, 1-cyclohexyl cyclopentyl, 1-(4-methoxy-n-butyl) cyclopentyl, 1-methyl cyclohexyl, 1-ethyl cyclohexyl, 3-methyl-1-cyclopentene-3-yl, 3-ethyl-1-cyclopentene-3-yl, 3-methyl-1-cyclohexene-3-yl, 3-ethyl-1-cyclohexene-3-yl, 1-(tetra hydrofuranyl)cyclopentyl, 1-(2-tetra hydrofuranyl)cyclohexyl, 1-(7-oxa-norbornane-2-yl) cyclopentyl, 1-(7-oxa-norbornane-2-yl) cyclohexyl, and the like.

Specific examples of the acid unstable group of the above-mentioned formula (L4) may be the following groups.

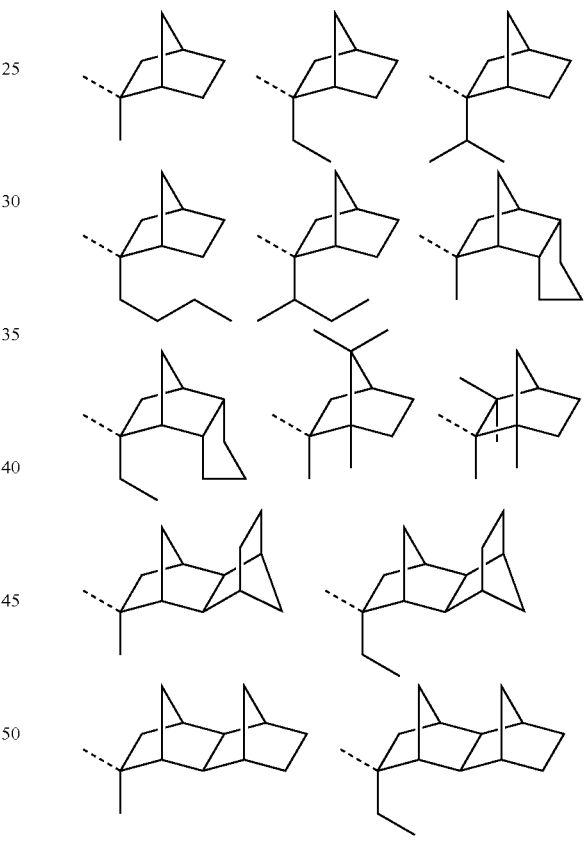

Specific examples of the tertiary alkyl group having 4–20 carbon atoms, the trialkylsilyl group wherein each of the alkyl groups has 1–6 carbon atoms and the oxoalkyl group having 4–20 carbon atoms may be the same as exemplified for $R^{L04}$.

X represents $CH_2$, an oxygen atom, or a sulfur atom. k is 0 or 1.

Other than those mentioned above, the polymer of the present invention may comprise the repeating units which are obtained from a monomer containing a carbon-carbon double bond, for example, substituted acrylic esters such as methyl methacrylate, methyl crotonate, dimethyl maleate, dimethyl itaconate and the like, unsaturated carboxylic acids such as maleic acid, fumaric acid, itaconic acid and the like, substituted norbornenes such as norbornene, and norbornene-5-carboxylic acid methyl, and the like, unsaturated acid anhydrides such as itaconic anhydride and the like, and other monomers.

A weight average molecular weight of the polymer of the present invention is 1,000–500,000, preferably 3,000–100,000, as measured using gel permeation chromatography (GPC) with polystyrene conversion. If it is out of this range, etching resistance may be lowered, or it becomes impossible to achieve a difference in a resolution power before and after exposure which may lead to lowering of a resolving power.

A content ratio of each repeating unit obtained from each of the monomers in the polymer of the present invention can be in the range (mol %) shown below. However, it is not limited thereto.

(I) one or more kinds of the constituting unit represented by the above-mentioned general formulae (1a)–(1d) are contained at a ratio of more than zero and 100 mol % or less, preferably 10 to 80 mol %, more preferably 20 to 60 mol % based on the monomer of the above-mentioned general formula (1), (II) one or more kinds of the constituting unit represented by the above-mentioned general formulae (M1)–(M13) are contained at a ratio of 0 mol % or more and less than 100 mol %, preferably 1 to 95 mol %, more preferably 40 to 80-mol %, and (III) one or more kinds of the constituting unit based on other monomers are contained at a ratio of 0 to 80 mol %, preferably 0 to 70 mol %, more preferably 0 to 50 mol %, if necessary.

The polymer of the present invention can be produced by a copolymerization reaction using the compound represented by the above-mentioned general formula (1) as the 1st monomer and a compound which contains a polymerizable double bond as the 2nd monomer.

Although various copolymerization reactions for producing the polymer of the present invention can be illustrated, radical polymerization, anionic polymerization, or coordination polymerization are preferable.

The reaction conditions of the radical polymerization reaction is as follows: (a) a hydrocarbon such as benzene or the like, an ether such as tetrahydrofuran or the like, an alcohol such as ethanol or the like, and a ketone such as methyl isobutyl ketone or the like, is used as a solvent; (b) an azo compound such as 2,2'-azobis isobutyronitril or the like, or peroxides such as benzoyl peroxide, lauroyl peroxide or the like is used as a polymerization initiator; (c) a reaction temperature is kept at about from 0° C. to 100° C.; (d) a reaction time is set to about from 0.5 hours to 48 hours. However, the case where it is out of this range is not eliminated.

The reaction conditions of the anionic polymerization reaction is as follows: (a) a hydrocarbon such as benzene, an ether such as tetrahydrofuran, or liquid ammonia is used as a solvent; (b) a metal such as sodium, potassium and the like, an alkyl metal such as n-butyl lithium, sec-butyl lithium and the like, ketyl or a Grignard-reaction agent is used as a polymerization initiator, (c) a reaction temperature is kept at about from −78° C. to 0° C., (d) a reaction time is set to about from 0.5 hours to 48 hours, e) a proton donor compound such as methanol or the like, halogenides such as methyl iodide, or other electrophilic substance is used as a terminator. However, the case where it is out of this range is not eliminated.

The reaction conditions of a coordination polymerization is as follows: (a) a hydrocarbon such as n-heptane, toluene or the like is used as a solvent; (b) Ziegler Natta catalyst which consists of a transition metal such as titanium or the like and an alkyl aluminum, Phillips catalyst wherein chromium and a nickel compound are carried on a metal oxide, an olefin-metathesis mixed catalyst represented by a mixed catalyst of tungsten and rhenium, or the like is used as a catalyst; (c) a reaction temperature is kept at about from 0° C. to 100° C.; (d) a reaction time is set to about from 0.5 hours to 48 hours. However, the case where it is out of this range is not eliminated.

Such a polymer of the present invention is effective as a base resin of a resist composition, and the present invention provides a resist composition characterized by containing this polymer as a base resin, especially a chemically amplified positive-resist composition.

Namely, the above-mentioned compound of the present invention can be easily obtained at high yield, and the resist composition which contains the polymer which comprises the repeating unit of the above-mentioned compound as a base resin is highly practical, since it is excellent in etching resistance, an adhesion property with a substrate, and a affinity with a developer, and has a high sensitivity and a high resolving power, and swelling at the time of development is small. The material is very effective especially as a resist composition in photolithography which uses high-energy beams such as ArF excimer laser light, KrF excimer laser light or the like as a light source.

There can be contained in the resist composition of the present invention, a compound generating an acid with a high-energy beam (hereinafter referred to as an acid generating agent), an organic solvent, and if necessary a dissolution controlling agent, a basic compound, and a compound which has a group represented by ≡C—COOH in a molecule, an acetylene alcohol derivative, a surfactant, and other components.

Examples of the acid generating agent used in the resist composition of the present invention are as follow:

i) an onium salt represented by the following general formula (Pla-1), (Pla-2), or (P1b), ii) a diazomethane derivative represented by the following general formula (P2), iii) a glyoxime derivative represented by the following general formula (P3), iv) a bissulfone derivative represented by the following general formula (P4), v) a sulfonate of a N-hydroxy imide compound represented by the following general formula (P5), vi) a β-keto sulfonic-acid derivative, vii) a disulfone derivative, viii) a nitro benzyl sulfonate derivative, ix) a sulfonate derivative, x) an oxime sulfonate, or the like.

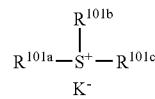

Pla-1

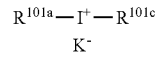

Pla-2

(In the formulae, $R^{101a}$, $R^{101b}$, and $R^{101c}$ independently represent a linear, branched or cyclic alkyl group, alkenyl group, oxoalkyl group or oxoalkenyl group each having 1–12 carbon atoms, an aryl group having 6–20 carbon atoms, an aralkyl group or an aryl oxoalkyl group having 7–12 carbon atoms. Some or all of hydrogen atoms of these groups may be substituted with an alkoxy group or the like.

$R^{101b}$ and $R^{101c}$ may constitute a ring. In the case that they constitute a ring, $R^{101b}$ and $R^{101c}$ represent an alkylene group having 1–6 carbon atoms respectively. $K^-$ represents an unnucleophilic counter ion.)

The above-mentioned $R^{101a}$, $R^{101b}$ and $R^{101c}$ may be the same or different. Specific examples thereof as an alkyl group may include: a methyl group, an ethyl group, a propyl group, an isopropyl group, n-butyl group, sec-butyl group, tert-butyl group, a pentyl group, a hexyl group, a heptyl group, an octyl group, a cyclopentyl group, a cyclohexyl group, a cycloheptyl group, a cyclopropyl methyl group, 4-methyl cyclohexyl group, a cyclohexyl methyl group, a norbornyl group, an adamantyl group, or the like. Specific examples of an alkenyl group may include: a vinyl group, an allyl group, a propenyl group, a butenyl group, a hexenyl group and a cyclohexenyl group, or the like. Examples of an oxoalkyl group may include: 2-oxocyclopentyl group, 2-oxocyclohexyl group, 2-oxopropyl group, 2-cyclopentyl-2-oxoethyl group, 2-cyclohexyl-2-oxoethyl group, 2-(4-methylcyclohexyl)-2-oxoethyl group, and the like. Examples of the oxoalkenyl group may include: 2-oxo-4-cyclohexenyl group, 2-oxo-4-propenyl group and the like. Examples of an aryl group may include: a phenyl group, a naphthyl group and the like, and an alkoxy phenyl group such as p-methoxyphenyl group, m-methoxyphenyl group, o-methoxyphenyl group, an ethoxyphenyl group, p-tert-butoxyphenyl group and m-tert-butoxyphenyl group, an alkyl phenyl group such as 2-methylphenyl group, 3-methylphenyl group, 4-methylphenyl group, an ethylphenyl group, 4-tert-butylphenyl group, 4-butylphenyl group, a dimethyl phenyl group and the like, an alkyl naphthyl group such as a methylnaphthyl group, an ethyl naphthyl group and the like, an alkoxy naphthyl group such as a methoxy naphthyl, an ethoxy naphthyl group and the like, a dialkyl naphthyl group such as a dimethyl naphthyl group and a diethyl naphthyl group and the like, a dialkoxy naphthyl group such as a dimethoxy naphthyl group and a diethoxy naphthyl group, and the like. Examples of the aralkyl group may include a benzyl group, a phenylethyl group, a phenethyl group and the like. Examples of an aryl oxoalkyl group may include: 2-aryl-2-oxoethyl group such as 2-phenyl-2-oxoethyl group, 2-(1-naphthyl)-2-oxoethyl group, and 2-(2-naphthyl)-2-oxoethyl group, or the like. Examples of an unnucleophilic counter ion as $K^-$ may include: a halide ion such as a chloride ion, a bromide ion or the like, a fluoro alkyl sulfonate such as triflate, 1,1,1-trifluoro ethanesulfonate, nonafluoro butane sulfonate or the like, an aryl sulfonate such as tosylate, benzene sulfonate, 4-fluorobenzene sulfonate, 1,2,3,4,5-pentafluoro benzene sulfonate or the like, an alkyl sulfonate such as mesylate, butane sulfonate or the like.

P1b

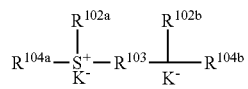

(In the formula, $R^{102a}$ and $R^{102b}$ each represent a linear, branched or cyclic alkyl group having 1–8 carbon atoms. $R^{103}$ represents a linear, branched or cyclic alkylene group having 1–10 carbon atoms. $R^{104a}$ and $R^{104b}$ each represent a 2-oxoalkyl group having 3–7 carbon atoms. $K^-$ represents an unnucleophilic counter ion.)

Specific examples of the above-mentioned $R^{102a}$ and $R^{102b}$ may include: a methyl group, an ethyl group, a propyl group, an isopropyl group, n-butyl group, sec-butyl group, tert-butyl group, a pentyl group, a hexyl group, a heptyl group, an octyl group, a cyclopentyl group, a cyclohexyl group, a cyclopropylmethyl group, 4-methylcyclohexyl group, a cyclohexyl methyl group and the like. Examples of $R^{103}$ may include: a methylene group, an ethylene group, a propylene group, a butylene group, a pentylene group, a hexylene group, a heptylene group, an octylene group, a nonylene group, 1,4-cyclohexylene group, 1,2-cyclohexylene group, 1,3-cyclopentylene group, 1,4-cyclooctylene group, 1,4-cyclohexane dimethylene group and the like. Examples of $R^{104a}$ and $R^{104b}$ may include: 2-oxopropyl group, 2-oxocyclopentyl group, 2-oxocyclohexyl group, 2-oxocycloheptyl group and the like. As $K^-$, the same as mentioned in the formulae (P1a-1) and (P1a-2) can be exemplified.

P2

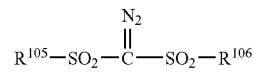

(In the formula, $R^{105}$ and $R^{106}$ represent a linear, branched or cyclic alkyl group or alkyl-halide group having 1–12 carbon atoms, an aryl group or aryl-halide group having 6–20 carbon atoms, or an aralkyl group having 7–12 carbon atoms.)

Examples of an alkyl group as $R^{105}$ and $R^{106}$ may include: a methyl group, an ethyl group, a propyl group, an isopropyl group, n-butyl group, sec-butyl group, tert-butyl group, a pentyl group, a hexyl group, a heptyl group, an octyl group, an amyl group, a cyclopentyl group, a cyclohexyl group, a cycloheptyl group, a norbornyl group, an adamantyl group and the like. Examples of a halogenated alkyl group may include: trifluoromethyl group, 1,1,1-trifluoroethyl group, 1,1,1-trichloroethyl group, a nonafluoro butyl group and the like. Examples of the aryl group may include: a phenyl group, an alkoxyphenyl group such as p-methoxyphenyl group, m-methoxyphenyl group, o-methoxyphenyl group, an ethoxyphenyl group, p-tert-butoxyphenyl group, m-tert-butoxyphenyl group or the like, an alkylphenyl groups such as 2-methylphenyl group, 3-methylphenyl group, 4-methylphenyl group, an ethylphenyl group, 4-tert-butylphenyl group, 4-butylphenyl group, a dimethylphenyl group or the like. Examples of the halogenated aryl group may include: a fluorophenyl group, a chlorophenyl group, 1,2,3,4,5-pentafluoro phenyl group and the like. Examples of the aralkyl group may include: a benzyl group, a phenethyl group, and the like.

P3

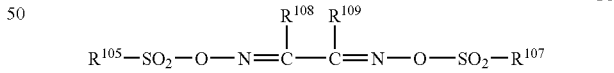

(In the formula, $R^{107}$, $R^{108}$ and $R^{109}$ represent a linear, branched, cyclic alkyl group or halogenated alkyl group having 1–12 carbon atoms, an aryl group or a halogenated aryl group having 6–20 carbon atoms, or an aralkyl group having 7–12 carbon atoms. $R^{108}$ and $R^{109}$ may be bonded each other and form a cyclic structure. When they form a cyclic structure, $R^{108}$ and $R^{109}$ each represent a linear or branched alkylene group having 1–6 carbon atoms. $R^{105}$ represents the same meaning as that in the formula P2.)

Examples of the alkyl group, the halogenated alkyl group, the aryl group, the halogenated aryl group, and the aralkyl group as $R^{107}$ $R^{108}$ and $R^{109}$ may be the same as exemplified for $R^{105}$ and $R^{106}$. In addition, as an alkylene group for $R^{108}$ and $R^{109}$, a methylene group, an ethylene group, a propylene group, a butylene group, a hexylene group and the like may be exemplified.

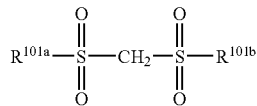

P4

(In the formula, $R^{101a}$ and $R^{101b}$ are the same as explained above.)

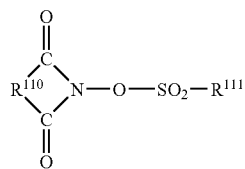

P5

(In the formula, $R^{110}$ represents an arylene group having 6–10 carbon atoms, an alkylene group having 1–6 carbon atoms or an alkenylene group having 2–6 carbon atoms. Some or all of hydrogen atoms of these groups may be further substituted with a linear, branched alkyl group or an alkoxy group having 1–4 carbon atoms, a nitro group, an acetyl group, or a phenyl group. $R^{111}$ represents a linear, branched or substituted alkyl group, alkenyl group or alkoxy alkyl group having 1–8 carbon atoms, a phenyl group or a naphthyl group. Some or all of hydrogen atoms of these groups may be substituted with an alkyl group or an alkoxy group having 1–4 carbon atoms; a phenyl group which may be substituted with an alkyl group or an alkoxy group having 1–4 carbon atoms, a nitro group or an acetyl group; a hetero aromatic group having 3–5 carbon atoms; or a chlorine atom or a fluorine atom.)

Examples of the arylene group as $R^{111}$ may include: 1,2-phenylene group, 1,8-naphtylene group and the like. Examples of the alkylene group may include: a methylene group, an ethylene group, a trimethylene group, a tetramethylene group, a phenylethylene group, a norbornane-2,3-di-yl group, and the like. Examples of the alkenylene group may include: 1,2-vinylene group, 1-phenyl-1,2-vinylene group, 5-norbornene-2,3-di-yl group and the like. Examples of the alkyl group as $R^{111}$ may be the same as exemplified for $R^{101a}$–$R^{101c}$. Examples of the alkenyl group as $R^{111}$ may include: a vinyl group, 1-propenyl group, an allyl group, 1-butenyl group, 3-butenyl group, an isoprenyl group, 1-pentenyl group, 3-pentenyl group, 4-pentenyl group, a dimethyl allyl group, 1-hexenyl group, 3-hexenyl group, 5-hexenyl group, 1-heptenyl group, 3-heptenyl group, 6-heptenyl group, 7-octenyl group and the like. Examples of the alkoxy alkyl group may include: a methoxy methyl group, an ethoxy methyl group, a propoxy methyl group, a butoxy methyl group, a pentyloxy methyl group, a hexyloxy methyl group, a heptyloxy methyl group, a methoxy ethyl group, an ethoxy ethyl group, a propoxy ethyl group, a butoxy ethyl group, pentyloxy ethyl group, a hexyloxy ethyl group, a methoxy propyl group, ethoxy propyl group, a propoxy propyl group, a butoxy propyl group, a methoxy butyl group, an ethoxy butyl group, a propoxy butyl group, a methoxy pentyl group, an ethoxy pentyl group, a methoxy hexyl group, a methoxy heptyl group and the like.

In addition, examples of the alkyl group having 1–4 carbon atoms which may be further substituted may include: a methyl group, an ethyl group, a propyl group, an isopropyl group, n-butyl group, an isobutyl group, tert-butyl group and the like. Examples of the alkoxy group having 1–4 carbon atoms may include: a methoxy group, an ethoxy group, a propoxy group, an isopropoxy group, n-butoxy group, an isobutoxy group, tert-butoxy group and the like. Examples of the phenyl group which may be substituted with an alkyl group and an alkoxy group having 1–4 carbon atoms, a nitro group or an acetyl group may include: a phenyl group, a tolyl group, p-tert-butoxy phenyl group, p-acetyl phenyl group, p-nitrophenyl group and the like. Examples of a hetero aromatic group having 3–5 carbon atoms may include: a pyridinyl group, a furil group and the like.

Specific examples of an acid generating agent may include: an onium salt such as trifluoromethane sulfonic acid diphenyl iodinium, trifluoromethane sulfonic acid(p-tert-butoxy phenyl)phenyl iodinium, p-toluenesulfonic acid diphenyl iodinium, p-toluenesulfonic acid(p-tert-butoxy phenyl)phenyl iodinium, trifluoromethane sulfonic acid triphenyl sulfonium, trifluoromethane sulfonic acid(p-tert-butoxy phenyl)diphenyl sulfonium, trifluoromethane sulfonic acid bis(p-tert-butoxy phenyl)phenyl sulfonium, trifluoromethane sulfonic-acid tris(p-tert-butoxy phenyl) sulfonium, p-toluenesulfonic acid triphenyl sulfonium, p-toluenesulfonic acid(p-tert-butoxy phenyl)diphenyl sulfonium, p-toluenesulfonic acid bis(p-tert-butoxy phenyl)phenyl sulfonium, p-toluenesulfonic-acid tris(p-tert-butoxy phenyl)sulfonium, nonafluoro butane sulfonic acid triphenyl sulfonium, butane sulfonic-acid triphenyl sulfonium, trifluoromethane sulfonic-acid trimethyl sulfonium, p-toluenesulfonic-acid trimethyl sulfonium, trifluoromethane sulfonic-acid cyclohexyl methyl(2-oxocyclohexyl) sulfonium, p-toluenesulfonic acid cyclohexyl methyl(2-oxo cyclohexyl)sulfonium, trifluoromethane sulfonic acid dimethyl phenyl sulfonium, p-toluenesulfonic acid dimethyl phenyl sulfonium, trifluoromethane sulfonic acid dicyclohexyl phenyl sulfonium, p-toluenesulfonic acid dicyclohexyl phenyl sulfonium, trifluoromethane sulfonic acid trinaphthylsulfonium, trifluoromethane sulfonic acid (2-norbonyl)methyl(2-oxocyclohexyl)sulfonium, ethylene bis [methyl(2-oxocyclopentyl)sulfonium trifluoromethane sulfonate], 1,2'-naphthyl carbonyl methyl-tetrahydro thiophenium triflate and the like.

Examples of a diazomethane derivative may include: bis(benzene sulfonyl)diazomethane, bis(p-toluene sulfonyl) diazomethane, bis(xylene sulfonyl)diazomethane, bis(cyclohexyl sulfonyl)diazomethane, bis(cyclopentyl sulfonyl)diazomethane, bis(n-butylsulfonyl)diazomethane, bis(isobutyl sulfonyl)diazomethane, bis(sec-butylsulfonyl)diazomethane, bis(n-propylsulfonyl)diazomethane, bis(isopropyl sulfonyl)diazomethane, bis(tert-butyl-sulfonyl)diazomethane, bis(n-amylsulfonyl)diazomethane, bis(isoamylsulfonyl)diazomethane, bis(sec-amylsulfonyl) diazomethane, bis(tert-amylsulfonyl)diazomethane, 1-cyclohexylsulfonyl-1-(tert-butyl-sulfonyl)diazomethane, 1-cyclohexyl sulfonyl-1-(tert-amyl sulfonyl)diazomethane, 1-tert-amyl sulfonyl-1-(tert-butyl-sulfonyl)diazomethane and the like.

Examples of a glyoxime derivative may include: bis-O-(p-toluene sulfonyl)-α-dimethylglyoxime, bis-O-(p-toluene sulfonyl)-α-diphenyl glyoxime, bis-O-(p-toluene sulfonyl)-α-dicyclohexyl glyoxime, bis-O-(p-toluene sulfonyl)-2,3-pentanedione glyoxime, bis-O-(p-toluene sulfonyl)-2-methyl-3,4-pentanedione glyoxime, bis-O-(n-butane sulfonyl)-α-dimethylglyoxime, bis-O-(n-butane sulfonyl)-α-diphenyl glyoxime, bis-O-(n-butane sulfonyl)-α-dicyclohexyl glyoxime, bis-O-(n-butane sulfonyl)-2,3-pentanedione glyoxime, bis-O-(n-butane sulfonyl)-2-methyl-3,4-pentanedione glyoxime, bis-O-(methane sulfonyl)-α-dimethylglyoxime, bis-O-(trifluoromethane sulfonyl)-α-dimethylglyoxime, bis-O-(1,1,1-trifluoro ethane sulfonyl)-α-dimethylglyoxime, bis-O-(tert-butane sulfonyl)-α-dimethylglyoxime, bis-O-(perfluoro octane sulfonyl)-α-dimethylglyoxime, bis-O-(cyclohexane sulfonyl)-α-dimethylglyoxime, bis-O-(benzene sulfonyl)-α-dimethylglyoxime, bis-O-(p-fluorobenzene sulfonyl)-α-dimethylglyoxime, bis-O-(p-tert-butylbenzene sulfonyl)-α-dimethylglyoxime, bis-O-(xylene sulfonyl)-α-dimethylglyoxime, bis-O-(camphor sulfonyl)-α-dimethylglyoxime and the like.

Examples of a bissulfone derivative may include: bis naphthyl sulfonyl methane, bis-trifluoro methyl sulfonyl methane, bis methyl sulfonyl methane, bis ethyl sulfonyl methane, bis propyl sulfonyl methane, bis isopropyl sulfonyl methane, bis-p-toluene sulfonyl methane, bis benzene sulfonyl methane and the like.

Examples of the β-ketosulfone derivative may include: 2-cyclohexyl carbonyl-2-(p-toluene sulfonyl)propane, 2-isopropyl carbonyl-2-(p-toluene sulfonyl)propane and the like.

Examples of the disulfone derivative may include: diphenyl disulfone derivative, a dicyclohexyl disulfone derivative and the like.

Examples of the nitro benzyl sulfonate derivative may include: p-toluenesulfonic acid 2,6-dinitro benzyl, p-toluenesulfonic acid 2,4-dinitro benzyl, and the like.

Examples of the sulfonate derivative may include: 1,2,3-tris(methane sulfonyloxy)benzene, 1,2,3-tris(trifluoromethane sulfonyloxy)benzene, 1,2,3-tris(p-toluene sulfonyloxy)benzene, and the like.

Examples of the sulfonate derivative of N-hydroxy imide compound may include: N-hydroxy succinimide methane sulfonate, N-hydroxy succinimide trifluoromethane sulfonate, N-hydroxy succinimide ethane sulfonate, N-hydroxy succinimide 1-propane sulfonate, N-hydroxy succinimide 2-propane sulfonate, N-hydroxy succinimide 1-pentane sulfonate, N-hydroxy succinimide 1-octane sulfonate, N-hydroxy succinimide p-toluenesulfonic-acid ester, N-hydroxy succinimide p-methoxybenzene sulfonate, N-hydroxy succinimide 2-chloroethane sulfonate, N-hydroxy succinimide benzenesulfonic-acid ester, N-hydroxy succinimide-2,4,6-trimethyl benzene sulfonate, N-hydroxy succinimide 1-naphthalene sulfonate, N-hydroxy succinimide 2-naphthalene sulfonate, N-hydroxy-2-phenyl succinimide methane sulfonate, N-hydroxy maleimide methane sulfonate, N-hydroxy maleimide ethane sulfonate, N-hydroxy-2-phenyl maleimide methane sulfonate, N-hydroxy glutarimide methane sulfonate, N-hydroxy glutarimide benzenesulfonic-acid ester, N-hydroxy phthalimide methane sulfonate, N-hydroxy phthalimide benzenesulfonic-acid ester, N-hydroxy phthalimide trifluoromethane sulfonate, N-hydroxy phthalimide p-toluenesulfonic-acid ester, N-hydroxy naphthalimide methane sulfonate, N-hydroxy naphthalimide benzenesulfonic-acid ester, N-hydroxy-5-norbornene-2,3-dicarboxyimido methane sulfonate, N-hydroxy-5-norbornene-2,3-dicarboxyimido trifluoromethane sulfonate, N-hydroxy-5-norbornene-2,3-dicarboxyimido p-toluenesulfonate and the like.

Preferable examples thereof may include: an onium salt such as trifluoromethane sulfonic-acid triphenyl sulfonium, trifluoromethane sulfonic-acid(p-tert-butoxy phenyl)diphenyl sulfonium, trifluoromethane sulfonic-acid tris(p-tert-butoxy phenyl)sulfonium, p-toluenesulfonic-acid triphenyl sulfonium, p-toluenesulfonic-acid(p-tert-butoxy phenyl) diphenyl sulfonium, p-toluenesulfonic-acid tris(p-tert-butoxy phenyl)sulfonium, trifluoromethane sulfonic-acid trinaphthylsulfonium, trifluoromethane sulfonic-acid cyclohexyl methyl(2-oxocyclohexyl)sulfonium, trifluoromethane sulfonic-acid(2-norbonyl)methyl(2-oxocyclohexyl)sulfonium, 1,2'-naphthyl carbonylmethyl tetrahydrothiophenium triflate, and the like;

a diazomethane derivative such as bis(benzene sulfonyl) diazomethane, bis(p-toluene sulfonyl) diazomethane, bis(cyclohexyl sulfonyl)diazomethane, bis(n-butylsulfonyl)diazomethane, bis(isobutyl sulfonyl)diazomethane, bis(sec-butylsulfonyl)diazomethane, bis(n-propyl sulfonyl)diazomethane, bis(isopropyl sulfonyl)diazomethane, bis(tert-butylsulfonyl)diazomethane and the like;

a glyoxime derivative, such as bis-O-(p-toluene sulfonyl)-α-dimethylglyoxime, bis-O-(n-butane sulfonyl)-α-dimethylglyoxime and the like;

a bissulfone derivative, such as bisnaphthyl sulfonyl methane;

a sulfonate derivative of N-hydroxyimide compounds, such as N-hydroxy succinimide methane sulfonate, N-hydroxy succinimide trifluoromethane sulfonate, N-hydroxy succinimide 1-propane sulfonate, N-hydroxy succinimide 2-propane sulfonate, N-hydroxy succinimide 1-pentane sulfonate, N-hydroxy succinimide p-toluene sulfonate, N-hydroxy naphthalimide methane sulfonate and N-hydroxy naphthalimide benzene sulfonate.

Examples of the oxime sulfonate may include: oxime sulfonates described in the specification of U.S. Pat. No. 6,004,724, especially (5-(4-toluene sulfonyl)oxyimino-5H-thiophene-2-ylidene)phenylacetonitrile, (5-(10-camphor sulfonyl)oxyimino-5H-thiophene-2-ylidene) phenylacetonitrile, (5-n-octane sulfonyloxy imino-5H-thiophene-2-ylidene)phenylacetonitrile, (5-(4-toluene sulfonyl)oxyimino-5H-thiophene-2-ylidene) (2-methyl phenyl) acetonitrile, (5-(10-camphor sulfonyl)oxy-imino-5H-thiophene-2-ylidene) (2-methyl phenyl)acetonitrile, (5-n-octane sulfonyl oxyimino-5H-thiophene-2-ylidene) (2-methyl phenyl)acetonitrile and the like.

There may also be exemplified oxime sulfonates described in specification of U.S. Pat. No.6,261,738 and Japanese Patent Application Laid-open (KOKAI) No.2000–314956, especially 2,2,2-trifluoro-1-phenylethanone oxime-O-methyl sulfonate; 2,2,2-trifluoro-1-phenylethanone oxime-O-(10-campholyl sulfonate); 2,2,2-trifluoro-1-phenylethanone oxime-O-(4-methoxy phenyl sulfonate); 2,2,2-trifluoro-1-phenylethanone oxime-O-(1-naphthyl sulfonate); 2,2,2-trifluoro-1-phenyl ethanone oxime-O-(2-naphthyl sulfonate); 2,2,2-trifluoro-1-phenyl ethanone oxime-O-(2,4,6-trimethyl phenyl sulfonate); 2,2,2-trifluoro-1-(4-methyl phenyl)-ethanone oxime-O-(10-campholyl sulfonate); 2,2,2-trifluoro-1-(4-methyl phenyl)-ethanone oxime-O-(methyl sulfonate); 2,2,2-trifluoro-1-(2-methyl phenyl)-ethanone oxime-O-(10-campholyl sulfonate); 2,2,2-trifluoro-1-(2,4-dimethyl phenyl)-ethanone oxime-O-(10-campholyl sulfonate); 2,2,2-trifluoro-1-(2,4-dimethyl phenyl)-ethanone oxime-O-(1-naphthyl sulfonate); 2,2,2-trifluoro-1-(2,4-dimethyl phenyl)-ethanone oxime-O-(2-naphthyl sulfonate); 2,2,2-trifluoro-1-(2,4,6-trimethyl phenyl)-ethanone oxime-O-(10-campholyl sulfonate); 2,2,2-trifluoro-1-(2,4,6-trimethyl phenyl)-ethanone oxime-O-(1-naphthyl sulfonate); 2,2,2-trifluoro-1-(2,4,6-trimethyl phenyl)-ethanone oxime-O-(2-naphthyl sulfonate); 2,2,2-trifluoro-1-(4-methoxy phenyl)-ethanone oxime-O-methyl sulfonate; 2,2,2-trifluoro-1-(4-methyl thiophenyl)-ethanone oxime-O-methyl sulfonate; 2,2,2-trifluoro-1-(3,4-dimethoxy phenyl)-ethanone oxime-O-methyl sulfonate; 2,2,3,3,4,4,4-heptafluoro-1-phenyl butanone oxime-O-(10-campholyl sulfonate); 2,2,2-trifluoro-1-(phenyl)-ethanone oxime-O-methyl sulfonate; 2,2,2-trifluoro-1-(phenyl)-ethanone oxime-O-10-campholyl sulfonate; 2,2,2-trifluoro-1-(phenyl)-ethanone oxime-O-(4-methoxy phenyl)sulfonate; 2,2,2-trifluoro-1-(phenyl)-ethanone oxime-O-(1-naphthyl) sulfonate; 2,2,2-trifluoro-1-(phenyl)-ethanone oxime-O-(2- naphthyl)sulfonate; 2,2,2-trifluoro-1-(phenyl)-ethanone oxime-O-(2,4,6-trimethyl phenyl) sulfonate; 2,2,2-trifluoro-1-(4-methyl phenyl)-ethanone oxime-O-(10-campholyl)sulfonate; 2,2,2-trifluoro-1-(4-methyl phenyl)-ethanone oxime-O-methyl sulfonate; 2,2,2-trifluoro-1-(2-methyl phenyl)-ethanone oxime-O-(10-campholyl)sulfonate; 2,2,2-trifluoro-1-(2,4-dimethyl phenyl)-ethanone oxime-O-(1-naphthyl)sulfonate; 2,2,2-trifluoro-1-(2, 4-dimethyl phenyl)-ethanone oxime-O-(2-naphthyl)sulfonate; 2,2,2-trifluoro-1-(2,4,6-trimethyl phenyl)-ethanone oxime-O-(10-campholyl)sulfonate; 2,2,2-trifluoro-1-(2,4,6-trimethyl phenyl)-ethanone oxime-O-(1-naphthyl)sulfonate; 2,2,2-trifluoro-1-(2,4,6-trimethyl phenyl)-ethanone oxime-O-(2-naphthyl)sulfonate; 2,2,2-trifluoro-1-(4-methoxy phenyl)-ethanone oxime-O-methyl sulfonate; 2,2,2-trifluoro-1-(4-thio methyl phenyl)-ethanone oxime-O-methyl sulfonate; 2,2,2-trifluoro-1-(3,4-dimethoxy phenyl)-ethanone oxime-O-methyl sulfonate; 2,2,2-trifluoro-1-(4-methoxy phenyl)-ethanone oxime-O-(4-methyl phenyl)sulfonate; 2,2,2-trifluoro-1-(4-methoxy phenyl)-ethanone oxime-O-(4-methoxy phenyl)sulfonate; 2,2,2-trifluoro-1-(4-methoxy phenyl)-ethanone oxime-O-(4-dodecyl phenyl)sulfonate; 2,2,2-trifluoro-1-(4-methoxy phenyl)-ethanone oxime-O-octyl sulfonate; 2,2,2-trifluoro-1-(4-thio methyl phenyl)-ethanone oxime-O-(4-methoxy phenyl sulfonate; 2,2,2-trifluoro-1-(4-thiomethyl phenyl)-ethanone oxime-O-(4-dodecyl phenyl) sulfonate; 2,2,2-trifluoro-1-(4-thio methyl phenyl)-ethanone oxime-O-octyl sulfonate; 2,2,2-trifluoro-1-(4-thio methyl phenyl)-ethanone oxime-O-(2-naphthyl)sulfonate; 2,2,2-trifluoro-1-(2-methyl phenyl)-ethanone oxime-O-methyl sulfonate; 2,2,2-trifluoro-1-(4-methyl phenyl)-ethanone oxime-O-phenyl sulfonate; 2,2,2-trifluoro-1-(4-chloro phenyl)-ethanone oxime-O-phenyl sulfonate; 2,2,3,3,4,4,4-heptafluoro-1-(Phenyl)-butanone oxime-O-(10-campholyl) sulfonate; 2,2,2-trifluoro-1-naphthyl ethanone oxime-O-methyl sulfonate; 2,2,2-trifluoro-2-naphthyl ethanone oxime-O-methyl sulfonate; 2,2,2-trifluoro-1-[4-benzyl phenyl]-ethanone oxime-O-methyl sulfonate; 2,2,2-trifluoro-1-[4-(phenyl-1,4-dioxabut-1-yl phenyl]-ethanone oxime-O-methyl sulfonate; 2,2,2-trifluoro-1-naphthyl ethanone oxime-O-propyl sulfonate; 2,2,2-trifluoro-2-naphthyl ethanone oxime-O-propyl sulfonate; 2,2,2-trifluoro-1-[4-benzyl phenyl]-ethanone oxime-O-propyl sulfonate; 2,2,2-trifluoro-1-[4-methyl sulfonyl phenyl]-ethanone oxime-O-propyl sulfonate; 1,3-bis[1-(4-phenoxyphenyl)-2,2,2-trifluoro ethanone oxime-O-sulfonyl]phenyl; 2,2,2-trifluoro-1-[4-methyl sulfonyloxy phenyl]-ethanone oxime-O-propyl sulfonate; 2,2,2-trifluoro-1-[4-methyl carbonyl oxy phenyl]-ethanone oxime-O-propyl sulfonate; 2,2,2-trifluoro-1-[6H, 7H-5,8-dioxonapht-2-yl]-ethanone oxime-O-propyl sulfonate; 2,2,2-trifluoro-1-[4-methoxycarbonyl methoxy phenyl]-ethanone oxime-O-propyl sulfonate; 2,2,2-trifluoro-1-[4-(methoxycarbonyl)-(4-amino-1-oxapenta-1-yl)-phenyl]-ethanone oxime-O-propyl sulfonate; 2,2,2-trifluoro-1-[3,5-dimethyl-4-ethoxy phenyl]-ethanone oxime-O-propyl sulfonate; 2,2,2-trifluoro-1-[4-benzyl oxy-phenyl]-ethanone oxime-O-propyl sulfonate; 2,2,2-trifluoro-1-[2-thio phenyl]-ethanone oxime-O-propyl sulfonate; 2,2,2-trifluoro-1-[1-dioxa-thiophene-2-yl]-ethanone oxime-O-propyl sulfonate and the like.

Furthermore, there may be exemplified oxime sulfonate α-(p-toluene sulfonyloxy imino)-phenylacetonitrile, α-(p-chlorobenzene sulfonyloxy imino)-phenylacetonitrile, α-(4-nitrobenzene sulfonyloxy imino)-phenylacetonitrile, α-(4-nitro-2-trifluoromethyl-benzene sulfonyloxy imino)-phenyl acetonitrile, α-(benzene sulfonyloxy imino)-4-chloro phenylacetonitrile, α-(benzene sulfonyloxy imino)-2,4-dichloro phenylacetonitrile, α-(benzene sulfonyloxy imino)-2,6-dichloro phenylacetonitrile, α-(benzene sulfonyloxy imino)-4-methoxy phenylacetonitrile, α-(2-chlorobenzene sulfonyloxy imino)-4-methoxy phenylacetonitrile, α-(benzene sulfonyloxy imino)-2-thienyl acetonitrile, α-(4-dodecylbenzene sulfonyloxy imino)-phenylacetonitrile, α-[(4-toluene sulfonyloxy imino)-4-methoxy phenyl]acetonitrile, α-[(dodecylbenzene sulfonyloxy imino)-4-methoxy phenyl] acetonitrile, α-(tosyloxy imino)-3-thienyl acetonitrile, an α-(methyl sulfonyloxy imino)-1-cyclopentenyl acetonitrile, α-(ethyl sulfonyloxy imino)-1-cyclopentenyl acetonitrile, α-(isopropyl sulfonyloxy imino)-1-cyclopentenyl acetonitrile, α-(n-butyl sulfonyloxy imino)-1-cyclopentenyl acetonitrile, α-(ethyl sulfonyloxy imino)-1-cyclohexenyl acetonitrile, α-(isopropyl sulfonyloxy imino)-1-cyclohexenyl acetonitrile, α-(n-butyl sulfonyloxy imino)-1-cyclohexenyl acetonitrile, and the like, which are described in Japanese Patent Application Laid-open (KOKAI) No.9-95479, Japanese Patent Application Laid-open (KOKAI) No.9-230588, or described as prior art therein.

Examples of the bis oxime sulfonate may include compounds described in Japanese Patent Application Laid-open (KOKAI) No.9-208554, especially bis(α-(4-toluenesulfonyloxy)imino)-p-phenylene diacetonitrile, bis(α-(benzenesulfonyloxy)imino)-p-phenylene diacetonitrile, bis(α-(methanesulfonyloxy)imino)-p-phenylene diacetonitrile bis (α-(butanesulfonyloxy)imino)-p-phenylene diacetonitrile, bis(α-(10-camphor sulfonyloxy)imino)-p-phenylene diacetonitrile, bis(α-(4-toluenesulfonyloxy)imino)-p-phenylene diacetonitrile, bis(α-(trifluoromethanesulfonyloxy)imino)-p-phenylene diacetonitrile, bis(α-(4-methoxybenzenesulfonyloxy)imino)-p-phenylene diacetonitrile, bis(α-(4-toluenesulfonyloxy)imino)-m-phenylene diacetonitrile, bis(α-(benzenesulfonyloxy)imino)-m-phenylene diacetonitrile, bis(α-(methanesulfonyloxy)imino)-m-phenylene diacetonitrile bis(α-(butanesulfonyloxy)imino)-m-phenylene diacetonitrile, bis(α-(10-camphor-sulfonyloxy)imino)-m-phenylene diacetonitrile, bis(α-(4-toluenesulfonyloxy)imino)-m-phenylene diacetonitrile, bis(α-(trifluoromethanesulfonyloxy)imino)-m-phenylene diacetonitrile, bis(α-(4-methoxybenzenesulfonyloxy) imino)-m-phenylene diacetonitrile, and the like.

The above-mentioned acid generating agent can be used alone or in combination of two or more of them. The onium salt is excellent in a rectangle shape improving effect, and the diazomethane derivative and the glyoxime derivative are excellent in a stationary wave reduction effect. Accordingly, if they are combined, a profile can be finely controlled.

An amount of the acid generating agent to be added is preferably 0.1 to 50 parts, more preferably 0.5 to 40 parts to 100 parts of a base polymer. If it is fewer than 0.1 parts, an amount of generation of the acid is few at the time of exposure, which may lead to inferior sensitivity and resolution. If it exceeds 50 parts, there may be caused sometimes a lowering of transparency of the resist, which may lead to inferior resolution.

An organic solvent which can be used in the resist composition of the present invention is not limited, as far as a base resin, an acid generating agent and other additives can be dissolved therein. Examples of such an organic solvent may include: ketones such as cyclohexanone, methyl-2-n-amyl ketone and the like; alcohols such as 3-methoxy butanol, 3-methyl-3-methoxy butanol, 1-methoxy-2-propanol, 1-ethoxy-2-propanol and the like; ethers such as propylene glycol monomethyl ether, ethylene glycol monomethyl ether, propylene-glycol monoethyl ether, ethylene glycol monoethyl ether, propylene-glycol dimethyl ether, diethylene-glycol dimethyl ether and the like; esters such as propylene-glycol-monomethyl-ether acetate, propylene-glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene-glycol mono-tert-butyl-ether acetate, lactones such as γ-butyl lactone and the like. They can be used alone or as a mixture of two or more of them. However, they are not limitative. According to the present invention, diethylene-glycol dimethyl ether, 1-ethoxy-2-propanol and propylene glycol monomethyl ether acetate or a mixture thereof which have the most excellent soluvility of the acid generating agent of the resist components can be preferably used among these organic solvents.

An amount of the organic solvent to be added is 200 to 1,000 parts, more preferably 400 to 800 parts to 100 parts of a base resin.

Furthermore, a dissolution controlling agent can be added to the resist composition of the present invention. Preferable examples of the dissolution controlling agent may be a compound having an average molecular weight of 100–1,000, preferably 150–800, wherein there are two or more of phenolic hydroxyl groups in a molecule, and hydrogen atoms of the phenolic hydroxyl groups are substituted with an acid unstable group at a ratio of 0–100-mol % on average, or there are carboxyl groups in a molecule, and hydrogen atoms of the carboxyl group are substituted with an acid unstable group at a ratio of 50–100 mol % on average.

The substitution rate with the acid unstable group of hydrogen atoms of the phenolic hydroxyl group is more than 0 mol % of the whole phenolic hydroxyl group on average, preferably more than 30 mol %, and the upper limit thereof is 100 mol %, preferably 80 mol %. The substitutional rate with the acid unstable group of hydrogen atoms of the carboxyl group is more than 50 mol % of the whole carboxyl groups on average, preferably more than 70 mol %, and the upper limit thereof is 100 mol %.

In this case, the compound which has two or more phenolic hydroxyl groups and the compound which has carboxyl groups are preferably the compounds represented by the following formulae (D1)–(D14).

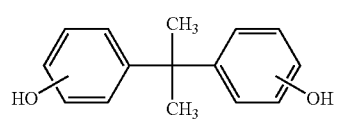

D1

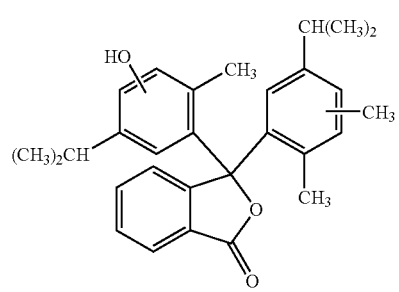

D2

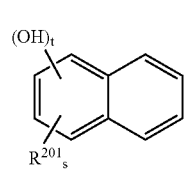

D3

-continued

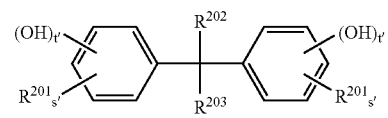

D4

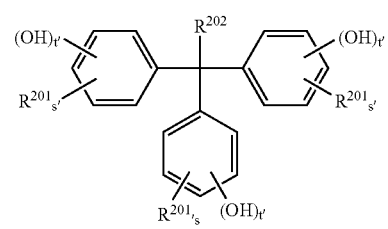

D5

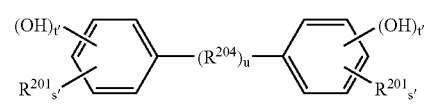

D6

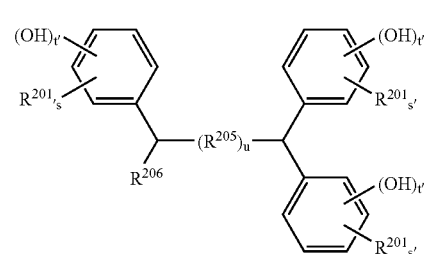

D7

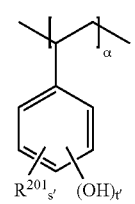

D8

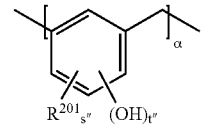

D9

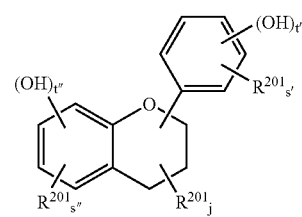

D10

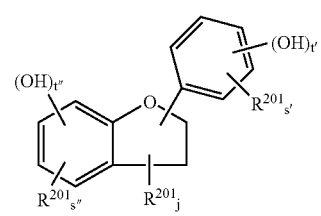

D11

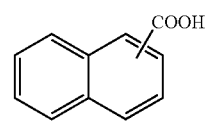

D12

-continued

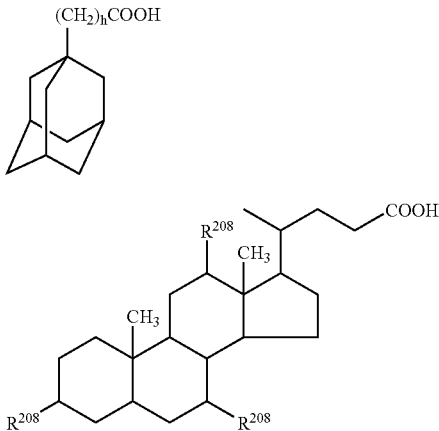

(D13)

(D14)

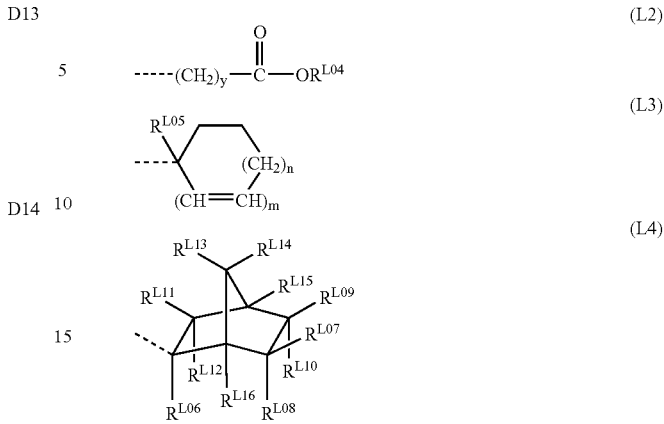

(L2)

(L3)

(L4)

(In the formulae, each of $R^{201}$ and $R^{202}$ represents a hydrogen atom or a linear or branched alkyl group or alkenyl group having 1–8 carbon atoms. $R^{203}$ represents a hydrogen atom or a linear or branched alkyl group or alkenyl group having 1–8 carbon atoms, or —$(R^{207})_h$COOH. $R^{204}$ represents —$(CH_2)_i$— (i=2–10), an arylene group having 6–10 carbon atoms, a carbonyl group, a sulfonyl group, an oxygen atom, or a sulfur atom. $R^{205}$ represents an alkylene group having 1–10 carbon atoms, an arylene group having 6–10 carbon atoms, a carbonyl group, a sulfonyl group, an oxygen atom, or a sulfur atom. $R^{206}$ represents a hydrogen atom, a linear or branched alkyl group or alkenyl group having 1–8 carbon atoms, a phenyl group or a naphthyl group each substituted with a hydroxyl group. $R^{207}$ represents a linear or branched alkylene group having 1–10 carbon atoms. $R^{208}$ represents a hydrogen atom or a hydroxyl group. j is an integer of 0–5. u and h are 0 or 1. s, t, s', t', s", t" satisfy s+t=8, s'+t'=5, s"+t"=4, and are the number so that each of the phenyl skelton may have at least one hydroxyl group. α is the number so that the molecular weight of the compounds of the formulae (D8) and (D9) may be 100 to 1,000.)

The weight average molecular weight of the above-mentioned compound is 100 to 1,000, preferably 150–800, and the blending amount of the resolution power preventing agent is 0–50 parts by weight, preferably 5–50 parts by weight, more preferably 10–30 parts by weight to 100 parts by weight of the base resin. They can be used alone or as a mixture. If the blending amount is few, there may be little improvement in a resolving power. If it is too much, film decrease in a pattern will be caused, and a resolution tends to be lowered.

The acid unstable group of the dissolution controlling agent can be various groups. Specific examples thereof may include: the groups represented by the following general formulae (L1)–(L4), tertiary alkyl group having 4–20 carbon atoms, a trialkylsilyl group wherein the carbon number of each alkyl group is 1–6, and an oxoalkyl group having 4–20 carbon atoms.

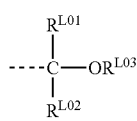

(L1)

(In the formulae, $R^{L01}$ and $R^{L02}$ represent a hydrogen atom or a linear, branched or cyclic alkyl group having 1–18 carbon atoms. $R^{L03}$ represents a monovalent hydrocarbon group having 1–18 carbon atoms which may have hetero atoms such as an oxygen atom. $R^{L01}$ and $R^{L02}$, $R^{L01}$ and $R^{L03}$, $R^{L02}$ and $R^{L03}$ may form a ring. In the case that they form a ring, $R^{L01}$, $R^{L02}$ and $R^{L03}$ independently represent a linear, branched or cyclic alkylene group having 1–18 carbon atoms. $R^{L04}$ represents tertiary alkyl group having 4–20 carbon atoms, a trialkylsilyl group wherein each of the alkyl groups has 1–6 carbon atoms, an oxoalkyl group having 4–20 carbon atoms, or a group represented by the above-mentioned general formula (L1). $R^{L05}$ represents a monovalent hydrocarbon group having 1–8 carbon atoms which may contain a hetero atom, or an aryl group having 6–20 carbon atoms which may be substituted. $R^{L06}$ represents a monovalent hydrocarbon group having 1–8 carbon atoms which may contain a hetero atom, or an aryl group having 6–20 carbon atoms which may be substituted. $R^{L07}$ to $R^{L16}$ independently represent a hydrogen atom or a monovalent hydrocarbon group having 1–15 carbon atoms which may contain a hetero atom. $R^{L07}$ to $R^{L16}$ may form a ring. In that case, they represent a divalent hydrocarbon group having 1–15 carbon atoms which may contain a hetero atom. Moreover, $R^{L07}$–$R^{L16}$ which bond to adjacent carbon atoms may bond to each other without anything between them to form a double bond. y is an integer of 0–6. m is 0 or 1, and n is any one of 0, 1, 2 or 3, and m and n are the number satisfying 2m+n=2 or 3.)

The blending amount of the above-mentioned dissolution controlling agent is 0 to 50 parts, preferably 0 to 40 parts, more preferably 0 to 30 parts to 100 parts of the base resin. They can be used alone or as a mixture of two or more of them. If the blending amount is more than 50 parts, film decrease in a pattern may be caused, and resolution may be lowered.

The above-mentioned dissolution controlling agents can be prepared by introducing an acid unstable group to a compound which has a phenolic hydroxyl group or a carboxyl group using an organic chemical method.

Furthermore, a basic compound can be blended in the resist composition of the present invention.

A basic compound which can suppress a diffusion rate when the acid generated by an acid generating agent in the resist film is preferable. By blending the basic compound, a diffusion rate of the acid in the resist film can be suppressed, and thereby a resolving power is improved, change of sensitivity after exposure is suppressed, dependency on the substrate or atmosphere can be decreased, and exposure margin or pattern profile and the like can be improved.

Examples of such a basic compound may include: a primary, secondary and tertiary aliphatic amines, a mixed amine, an aromatic amine, a heterocyclic amine, a compound containing nitrogen which has a carboxyl group, a compound containing nitrogen which has a sulfonyl group, a compound containing nitrogen which has a hydroxyl group, a compound containing nitrogen which has a hydroxy phenyl group, an alcohol compound containing nitrogen, an amide derivative, an imido derivative and the like.

Specific examples of the primary aliphatic amine may include: ammonia, methylamine, ethylamine, n-propylamine, isopropylamine, n-butylamine, isobutyl amine, sec-butyl-amine, tert-butylamine, pentylamine, tert-amylamine, cyclopentyl amine, hexylamine, cyclohexyl amine, heptylamine, octylamine, nonylamine, decyl amine, dodecylamine, cetylamine, methylene diamine, ethylenediamine, tetraethylene pentamine and the like. Examples of the secondary aliphatic amine may include: dimethylamine, diethylamine, di-n-propylamine, diisopropyl amine, di-n-butylamine, diisobutyl amine, di-sec-butylamine, dipentylamine, dicyclopentyl amine, dihexyl amine, dicyclohexyl amine, diheptylamine, dioctylamine, dinonylamine, didecylamine, didodecylamine, dicetylamine, N,N-dimethyl methylenediamine, N,N-dimethyl ethylenediamine, N,N-dimethyl tetraethylenepentamine and the like. Examples of the tertiary aliphatic amine may include: trimethylamine, triethylamine, tri-n-propylamine, triisopropyl amine, tri-n-butyl amine, tri-isobutyl amine, tri-sec-butyl amine, tripentyl amine, tricyclopentyl amine, trihexyl amine, tricyclohexyl amine, triheptyl amine, trioctyl amine, trinonyl amine, tridecyl amine, tridodecyl amine, tricetyl amine, N,N,N',N'-tetra methyl methylene diamine, N,N,N',N'-tetramethyl ethylenediamine, N,N,N',N'-tetramethyl tetraethylene pentamine and the like.

Moreover, examples of the mixed amines may include: a dimethyl ethylamine, methyl ethyl propyl amine, benzylamine, phenethyl amine, benzyl dimethylamine, and the like.

Examples of the aromatic amines and the heterocyclic amines may include: an aniline derivative (for example, aniline, N-methyl aniline, and N-ethyl aniline, N-propyl aniline, N,N-dimethylaniline, 2-methyl aniline, 3-methyl aniline, 4-methyl aniline, ethyl aniline, propyl aniline, trimethyl aniline, 2-nitroaniline, 3-nitroaniline, 4-nitroaniline, 2,4-dinitro aniline, 2,6-dinitro aniline, 3,5-dinitro aniline, N,N-dimethyl toluidine and the like), diphenyl(p-tolyl) amine, methyl diphenylamine, triphenylamine, phenylenediamine, naphthylamine, diamino naphthalene, a pyrrole derivative (for example, pyrrole, 2H-pyrrole, 1-methyl pyrrole, 2,4-dimethyl pyrrole, 2,5-dimethyl pyrrole, N-methyl pyrrole, and the like), oxazole derivative (for example, oxazole, isoxazole and the like), a thiazole derivative (for example, thiazole, isothiazole, and the like), an imidazole derivative (for example, imidazole, 4-methyl imidazole, 4-methyl-2-phenyl imidazole and the like), a pyrazole derivative, a furazan derivative, a pyrroline derivative (for example, pyrroline, 2-methyl-1-pyrroline and the like), a pyrrolidine derivative (for example, pyrrolidine, N-methyl pyrrolidine, pyrrolidinone, N-methyl pyrolidone and the like), an imidazoline derivative, an imidazolidine derivative, a pyridine derivative (for example, pyridine, methyl pyridine, ethyl pyridine, propyl pyridine, butyl pyridine, 4-(1-butyl pentyl)pyridine, dimethyl pyridine, trimethyl pyridine, triethyl pyridine, phenyl pyridine, 3-methyl-2-phenyl pyridine, 4-tert-butyl pyridine, diphenyl pyridine, benzyl pyridine, methoxy pyridine, butoxy pyridine, dimethoxy pyridine, 1-methyl-2-pyridone, 4-pyrrolidino pyridine, 1-methyl-4-phenyl pyridine, 2-(1-ethylpropyl)pyridine, amino pyridine, dimethyl amino pyridine and the like), a pyridazine derivative, a pyrimidine derivative, a pyrazine derivative, a pyrazoline derivative, a pyrazolidine derivative, a piperidine derivative, a piperazine derivative, a morpholine derivative, an indole derivative, an isoindole derivative, a 1H-indazole derivative, an indoline derivative, a quinoline derivative (for example, quinoline, 3-quinoline carbonitrile, and the like), an isoquinoline derivative, a cinnoline derivative, a quinazoline derivative, a quinoxaline derivative, a phthalazine derivative, a purine derivative, a pteridine derivative, a carbazole derivative, a phenanthridine derivative, an acridine derivative, a phenazine derivative, 1,10-phenanthroline derivative, an adenine derivative, an adenosine derivative, a guanine derivative, a guanosine derivative, an uracil derivative, an uridine derivative and the like.

Furthermore, examples of a compound containing nitrogen which has a carboxyl group may include: aminobenzoic acid, indole carboxylic acid, and an amino acid derivative (for example, nicotinic acid, alanine, arginine, aspartic acid, glutamic acid, glycine, histidine, isoleucine, glycyl leucine, leucine, methionine, phenylalanine, threonine, lysine, 3-aminopyrazine-2-carboxylic acid, methoxy alanine) and the like. Examples of a compound containing nitrogen which has a sulfonyl group may include: 3-pyridine sulfonic acid, p-toluenesulfonic acid pyridinium and the like. Examples of a compound containing nitrogen which has a hydroxyl group, a compound containing nitrogen which has a hydroxy phenyl group, and an alcohol compound containing nitrogen may include: 2-hydroxy pyridine, amino cresol, 2,4-quinoline diol, 3-Indole methanol hydrate, monoethanolamine, diethanolamine, triethanolamine, N-ethyl diethanolamine, N,N-diethyl ethanolamine, triisopropanol amine, 2,2'-iminodiethanol, 2-amino ethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxy ethyl)pyrrolidine, 1-(2-hydroxyethyl)-2-pyrrolidinone, 3-piperidinone-1,2-propanediol, 3-pyrrolidino-1,2-propanediol, 8-hydroxy julolidine, 3-quinuclidinol, 3-tropanol, 1-methyl-2-pyrrolidine ethanol, 1-aziridine ethanol, N-(2-hydroxyethyl)phthalimide, N-(2-hydroxyethyl)isonicotinamide, and the like.

Examples of an amide derivative may include: formamide, N-methyl formamide, N,N-dimethylformamide, acetamide, N-methyl acetamide, N,N-dimethylacetamide, propione amide, benzamide, and the like. Examples of an imido derivative may include: phthalimide, succinimide, maleimide, or the like.

Furthermore, one or more selected from the basic compound represented by following general formula (B)-1 can also be added.

$$N(X)_n(Y)_{3-n} \qquad (B)\text{-}1$$

(In the formula, n is 1, 2, or 3. The side chain X may be the same or different, and represent the following general formulae (X)-1 to (X)-3. The side chain Y may be the same or different, and represent a hydrogen atom or a linear, branched or cyclic alkyl group having 1–20 carbon atoms which may contain an ether group or a hydroxyl group. Moreover, X may bond to each other and form a ring.)

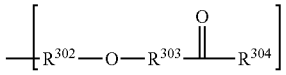

-continued

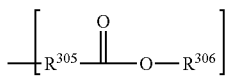
(X)-3

(In the formulae, $R^{300}$, $R^{302}$, and $R^{305}$ represent a linear or branched alkylene group having 1–4 carbon atoms, and $R^{301}$ and $R^{304}$ represent a hydrogen atom or a linear, branched or cyclic alkyl group having 1–20 carbon atoms, which may contain one or more of a hydroxy group, an ether group, an ester group, and a lactone ring. $R^{303}$ represents a single bond, or a linear or branched alkylene group having 1–4 carbon atoms, $R^{306}$ represents a linear, branched or cyclic alkyl group having 1–20 carbon atoms, which may contain one or more of a hydroxy group, an ether group, an ester group, and a lactone ring.)

Examples of the compound represented by the general formula (B)-1 may be as follows:

Tris(2-methoxy methoxy ethyl)amine, tris{2-(2-methoxyethoxy)ethyl}amine, tris{2-(2-methoxy ethoxy methoxy)ethyl}amine, tris{2-(1-methoxyethoxy)ethyl}amine, tris{2-(1-ethoxy ethoxy)ethyl}amine, tris{2-(1-ethoxy propoxy)ethyl}amine, tris[2-{2-(2-hydroxy ethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclo octadecane, 1-aza-12-crown-4,1-aza-15-crown-5,1-aza-18-crown-6, tris (2-formyloxy-ethyl)amine, tris(2-formyloxy-ethyl)amine, tris(2-acetoxy ethyl)amine, tris(2-propionyloxy-ethyl) amine, tris(2-butylyloxy-ethyl)amine, tris(2-isobutyryl oxy-ethyl)amine, tris(2-valeryloxy-ethyl)amine, tris(2-pivaloyloxy-ethyl)amine, N,N-bis(2-acetoxy ethyl)2-(acetoxyacetoxy)ethylamine, tris(2-methoxycarbonyl oxyethyl)amine, tris(2-tert-butoxy carbonyl oxy-ethyl)amine, tris[2-(2-oxo propoxy)ethyl]amine, tris[2-(methoxycarbonylmethyl)oxy-ethyl]amine, tris[2-(tert-butoxycarbonylmethyloxy)ethyl]amine, tris[2-(cyclohexyloxy carbonylmethyloxy)ethyl]amine, tris (2-methoxycarbonyl ethyl)amine, tris (2-ethoxy carbonyl ethyl)amine, N,N-bis(2-hydroxy ethyl) 2-(methoxycarbonyl)ethylamine, N,N-bis(2-acetoxy ethyl) 2-(methoxycarbonyl)ethylamine, N,N-bis(2-hydroxy ethyl) 2-(ethoxy carbonyl)ethylamine, N,N-bis(2-acetoxy ethyl)2-(ethoxy carbonyl)ethylamine, N,N-bis(2-hydroxy ethyl)2-(2-methoxy ethoxy carbonyl)ethylamine, N,N-bis(2-acetoxy ethyl)2-(2-methoxy ethoxy carbonyl)ethylamine, N,N-bis (2-hydroxy ethyl)2-(2-hydroxy ethoxy carbonyl)ethylamine, N,N-bis(2-acetoxy ethyl)2-(2-acetoxy ethoxy carbonyl)ethylamine, N,N-bis(2-hydroxy ethyl)2-[(methoxycarbonyl)methoxycarbonyl]ethylamine, N,N-bis (2-acetoxy ethyl)2-[(methoxycarbonyl)methoxycarbonyl] ethylamine, N,N-bis(2-hydroxy ethyl)-2-(2-oxo propoxy carbonyl)ethylamine, N,N-bis(2-acetoxy ethyl)-2-(2-oxo propoxy carbonyl)ethylamine, N,N-bis(2-hydroxy ethyl)2-(tetrahydro furfuryl oxy-carbonyl)ethylamine, N,N-bis(2-acetoxy ethyl)2-(tetrahydro furfuryl oxy-carbonyl)ethylamine, N,N-bis(2-hydroxy ethyl)2-[(2-oxo tetrahydrofuran-3-yl)oxy-carbonyl]ethylamine, N,N-bis(2-acetoxy ethyl)2-[(2-oxo-tetrahydrofuran-3-yl)oxy-carbonyl]ethylamine, N,N-bis(2-hydroxy ethyl)2-(4-hydroxy butoxy carbonyl)ethylamine, N,N-bis(2-formyl oxy-ethyl)2-(4-formyloxybutoxy carbonyl)ethylamine, N,N-bis(2-formyl oxy-ethyl)2-(2-formyloxy ethoxy carbonyl)ethylamine, N,N-bis(2-methoxy ethyl)2-(methoxycarbonyl)ethylamine, N-(2-hydroxy ethyl)bis[2-(methoxycarbonyl)ethyl]amine, N-(2-acetoxy ethyl)bis[2-(methoxycarbonyl)ethyl]amine, N-(2-hydroxy ethyl)bis[2-(ethoxy carbonyl)ethyl]amine, N-(2-acetoxy ethyl)bis[2-(ethoxycarbonyl)ethyl]amine, N-(3-hydroxy-1-propyl)bis[2-(methoxycarbonyl)ethyl]amine, N-(3-acetoxy-1-propyl)bis[2-(methoxycarbonyl)ethyl]amine, N-(2-methoxy ethyl)bis[2-(methoxycarbonyl)ethyl]amine, N-butylbis[2-(methoxycarbonyl)ethyl]amine, N-butylbis[2-(methoxy ethoxy carbonyl)ethyl]amine, N-methyl bis(2-acetoxy ethyl)amine, N-ethyl bis(2-acetoxy ethyl)amine, N-methyl bis(2-pivaloyloxy-ethyl)amine, N-ethyl bis[2-(methoxy carbonyloxy)ethyl]amine, N-ethyl bis[2-(tert-butoxycarbonyloxy)ethyl]amine, tris(methoxycarbonyl methyl)amine, tris(ethoxy carbonyl methyl)amine, N-butyl bis(methoxycarbonyl methyl)amine, N-hexyl bis (methoxycarbonyl methyl)amine, and β-(diethylamino)-δ-valerolactone. However they are not limited thereto.

Furthermore, one or more kinds of a basic compound with the cyclic structure represented in following general formula (B)-2 can also be added.

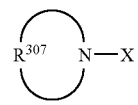
(B)-2

(In the formula, X represents the same as explained above, $R^{307}$ represents a linear or branched alkylene group having 2–20 carbon atoms, which may contain one or more of a carbonyl group, an ether group, an ester group, or a sulfide.)

Specific examples of (B)-2 may include: 1-[2-(methoxy methoxy)ethyl]pyrrolidine, 1-[2-(methoxy methoxy)ethyl]piperidine, 4-[2-(methoxy methoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, acetic acid 2-(1-pyrrolidinyl)ethyl, acetic acid 2-piperidino ethyl, acetic-acid 2-morpholino ethyl, formic acid 2-(1-pyrrolidinyl)ethyl, propionic-acid 2-piperidino ethyl, acetoxy acetic-acid 2-morpholino ethyl, methoxy acetic-acid 2-(1-pyrrolidinyl)ethyl, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, 3-(1-pyrrolidinyl) methyl propionate, 3-piperidino methyl propionate, 3-morpholino methyl propionate, 3-(thiomorpholino)methyl propionate, 2-methyl-3-(1-pyrrolidinyl)methyl propionate, 3-morpholino ethyl propionate, 3-piperidino propionic-acid methoxycarbonyl methyl, 3-(1-pyrrolidinyl)propionic-acid 2-hydroxy ethyl, 3-morpholino propionic-acid 2-acetoxy ethyl, 3-(1-pyrrolidinyl)propionic-acid 2-oxo tetrahydrofuran-3-yl, 3-morpholino propionic-acid tetra hydro furfuryl, 3-piperidino propionic-acid glycidyl, 3-morpholino propionic-acid 2-methoxy ethyl, 3-(1-pyrrolidinyl) propionic-acid 2-(2-methoxyethoxy)ethyl, 3-morpholino butyl propionate, 3-piperidino propionic-acid cyclohexyl, α-(1-pyrrolidinyl)methyl-γ-butyrolactone, β-piperidino-γ-butyrolactone, β-morpholino-δ-valerolactone, 1-pyrrolidinyl methyl acetate, piperidino methyl acetate, morpholino methyl acetate, thio morpholino methyl acetate, 1-pyrrolidinyl ethyl acetate, morpholino acetic-acid 2-methoxy ethyl, and the like.

Furthermore, the basic compound containing a cyano group represented by the general formula (B)-3 to (B)-6 can be added.

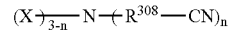
(B)-3

-continued

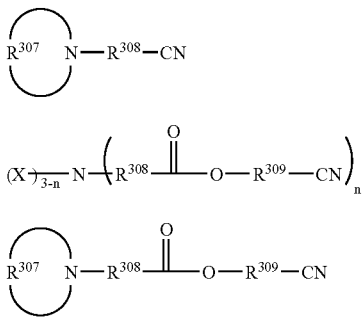

(In the formulae, X, $R^{307}$, and n are the same as explained above, $R^{308}$ and $R^{309}$ are the same or different, represent a linear or branched alkylene group having 1–4 carbon atoms.)

The basic compound containing a cyano group specifically 3-(diethylamino)propiononitrile, N,N-bis(2-hydroxy ethyl)-3-amino propiononitrile, N,N-bis(2-acetoxy ethyl)-3-amino propiononitrile, N,N-bis(2-formyl oxy-ethyl)-3-amino propiononitrile, N,N-bis(2-methoxy ethyl)-3-amino propiononitrile, N,N-bis[2-(methoxy methoxy)ethyl]-3-amino propiononitrile, N-(2-cyanoethyl)-N-(2-methoxy ethyl)-3-amino methyl propionate, N-(2-cyanoethyl)-N-(2-hydroxy ethyl)-3-amino methyl propionate, N-(2-acetoxy ethyl)-N-(2-cyanoethyl)-3-amino methyl propionate, N-(2-cyanoethyl)-N-ethyl-3-amino propiononitrile, N-(2-cyanoethyl)-N-(2-hydroxy ethyl)-3-amino propiononitrile, N-(2-acetoxy ethyl)-N-(2-cyanoethyl)-3-amino propiononitrile, N-(2-cyanoethyl)-N-(2-formyl oxy-ethyl)-3-amino propiononitrile, N-(2-cyanoethyl)-N-(2-methoxy ethyl)-3-amino propiononitrile, N-(2-cyanoethyl)-N-[2-(methoxy methoxy) ethyl]-3-amino propiononitrile, N-(2-cyanoethyl)-N-(3-hydroxy-1-propyl)-3-amino propiononitrile, N-(3-acetoxy-1-propyl)-N-(2-cyanoethyl)-3-amino propiononitrile, N-(2-cyanoethyl)-N-(3-formyloxy-1-propyl)-3-amino propiononitrile, N-(2-cyanoethyl)-N-tetrahydro furfuryl-3-amino propiononitrile, N,N-bis(2-cyanoethyl)-3-amino propiononitrile, diethyl amino acetonitrile, N,N-bis(2-hydroxy ethyl)amino acetonitrile, N,N-bis(2-acetoxy ethyl)amino acetonitrile, N,N-bis(2-formyl oxy-ethyl)amino acetonitrile, N,N-bis(2-methoxy ethyl)amino acetonitrile, N,N-bis[2-(methoxy methoxy)ethyl]amino acetonitrile, N-cyanomethyl-N-(2-methoxy ethyl)-3-amino methyl propionate, N-cyanomethyl-N-(2-hydroxy ethyl)-3-amino methyl propionate, N-(2-acetoxy ethyl)-N-cyanomethyl-3-amino methyl propionate, N-cyanomethyl-N-(2-hydroxy ethyl)amino acetonitrile, N-(2-acetoxy ethyl)-N-(cyanomethyl)amino acetonitrile, N-cyanomethyl-N-(2-formyloxy-ethyl)amino acetonitrile, N-cyanomethyl-N-(2-methoxy ethyl)amino acetonitrile, N-cyanomethyl-N-[2-(methoxymethoxy)ethyl] amino acetonitrile, N-(cyanomethyl)-N-(3-hydroxy-1-propyl)amino acetonitrile, N-(3-acetoxy-1-propyl)-N-(cyanomethyl)amino acetonitrile, N-cyanomethyl-N-(3-formyloxy-1-propyl)amino acetonitrile, N,N-bis(cyanomethyl)amino acetonitrile, 1-pyrrolidine propiononitrile, 1-piperidine propiononitrile, 4-morpholine propiononitrile, 1-pyrrolidine acetonitrile, 1-piperidine acetonitrile, 4-morpholine acetonitrile, 3-diethyl amino propionic acid cyanomethyl, N,N-bis (2-hydroxyethyl)-3-amino propionic-acid cyanomethyl, N,N-bis(2-acetoxy ethyl)-3-amino propionic-acid cyanomethyl, N,N-bis(2-formyloxy-ethyl)-3-amino propionic-acid cyanomethyl, N,N-bis(2-methoxy ethyl)-3-amino propionic-acid cyanomethyl, N,N-bis[2-(methoxy methoxy) ethyl]-3-amino propionic-acid cyanomethyl, 3-diethyl amino propionic-acid(2-cyanoethyl), N,N-bis(2-hydroxy ethyl)-3-amino propionic acid(2-cyanoethyl), N,N-bis(2-acetoxyethyl)-3-amino propionic acid (2-cyanoethyl), N,N-bis (2-formyl oxy-ethyl)-3-amino propionic acid(2-cyanoethyl), N,N-bis(2-methoxy ethyl)-3-amino propionic acid(2-cyanoethyl), N,N-bis[2-(methoxy methoxy)ethyl]-3-amino propionic acid(2-cyanoethyl), 1-pyrrolidine propionic acid cyanomethyl, 1-piperidine propionic-acid cyanomethyl, 4-morpholine propionic acid cyanomethyl, 1-pyrrolidine propionic acid(2-cyanoethyl), 1-piperidine propionic acid(2-cyanoethyl), 4-morpholine propionic acid(2-cyanoethyl), and the like.

The blending amount of the basic compound in the resist composition of the present invention is preferably 0.001 to 2 parts, especially 0.01 to 1 parts to 100 parts of the total base resin. If the amount is fewer than 0.001 parts, the effects achieved by blending is small. If the blending amount is more than 2 parts, sensitivity may be lowered too much.

As a compound which has the group represented by ≡C—COOH in the molecule which can be added into the resist composition of the present invention, one or more kinds of compounds can be selected, for example from the following I group and II group, but it is not limited thereto. The PED (Post Exposure Delay) stability of a resist is improved, and edge roughness on a nitride board is improved by blending the component.

[I Group]

The compound wherein some or all hydrogen atoms of phenolic hydroxyl groups of the compound represented by following general formula (A1)–(A10) are substituted with —$R^{401}$—COOH ($R^{401}$ is a linear or branched alkylene group having 1–10 carbon atoms), and a mole ratio of the phenolic hydroxyl group (C) and the group (D) represented by ≡C—COOH in a molecule is C/(C+D), which satisfies the formula: C/(C+D)=0.1 to 1.0.

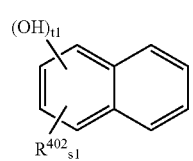

A1

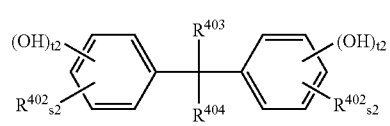

A2

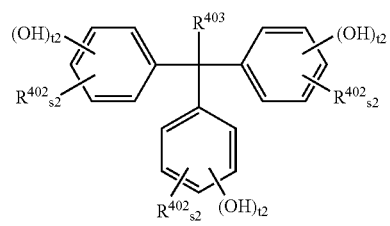

A3

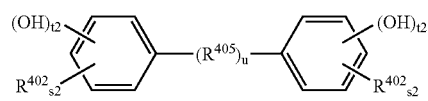

A4

-continued

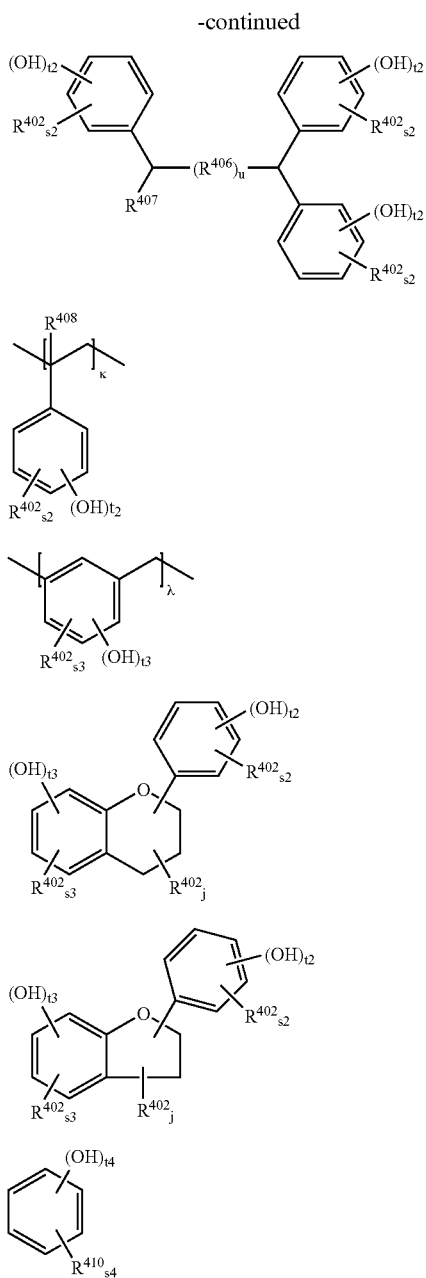

A5

A6

A7

A8

A9

A10

(In the formulae, $R^{408}$ represents a hydrogen atom or a methyl group. $R^{402}$ and $R^{403}$ independently represent a hydrogen atom or a linear or branched alkyl group or alkenyl group having 1–8 carbon atoms. $R^{404}$ represents a hydrogen atom or a linear or branched alkyl group or alkenyl group having 1–8 carbon atoms, or —$(R^{409})_h$—COOR' (R' is a hydrogen atom or —$R^{409}$—COOH). $R^{405}$ represents —$(CH_2)_i$— (i=2–10), an arylene group having 6–10 carbon atoms, a carbonyl group, a sulfonyl group, an oxygen atom, or a sulfur atom. $R^{406}$ represents an alkylene group having 1–10 carbon atoms, an arylene group having 6–10 carbon atoms, a carbonyl group, a sulfonyl group, an oxygen atom, or a sulfur atom. $R^{407}$ represents a hydrogen atom or a linear or branched alkyl group or alkenyl group having 1–8 carbon atoms, a phenyl group or a naphthyl group substituted with a hydroxyl group. $R^{409}$ represents a linear or branched alkyl group or alkenyl group having 1–10 carbon atoms, or a —$R^{411}$—COOH group. $R^{410}$ represents a hydrogen atom or a linear or branched alkyl group or alkenyl group having 1–8 carbon atoms, or a —$R^{411}$—COOH group. $R^{411}$ represents a linear or branched alkylene group having 1–10 carbon atoms. h is an integer of 1–4. j is the number of 0–3. Each of s1–4 and t1–4 satisfy s1+t1=8, s2+t2=5, s3+t3=4, and s4+t4=6, and is the number so that at least one hydroxyl group exists in each phenyl skeleton. u is an integer of 1–4. κ is the number so that the weight average molecular weight of the compound of the formula (A6) may be 1,000–5,000. λ is the number so that the weight average molecular weight of the compound of the formula (A7) may be 1,000–10,000.)

[II Group]

The compound represented by following general formula (A11)–(A15).

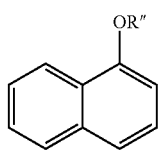

A11

A12

A13

A14

A15

(In the formulae, $R^{402}$, $R^{403}$, and $R^{411}$ represent the same as explained above. $R^{412}$ represents a hydrogen atom or a hydroxyl group. s5 and t5 are the numbers which satisfy: s5≧0, t5≧0, and s5+t5=5. h satisfies: 1≦h≦4.)

Specific examples of the above component may include compounds represented by following general formulae AI-1 to AI-14 and AII-1 to AII-10. However, it is not limited thereto.

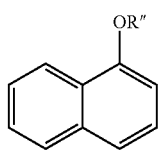

AI-1

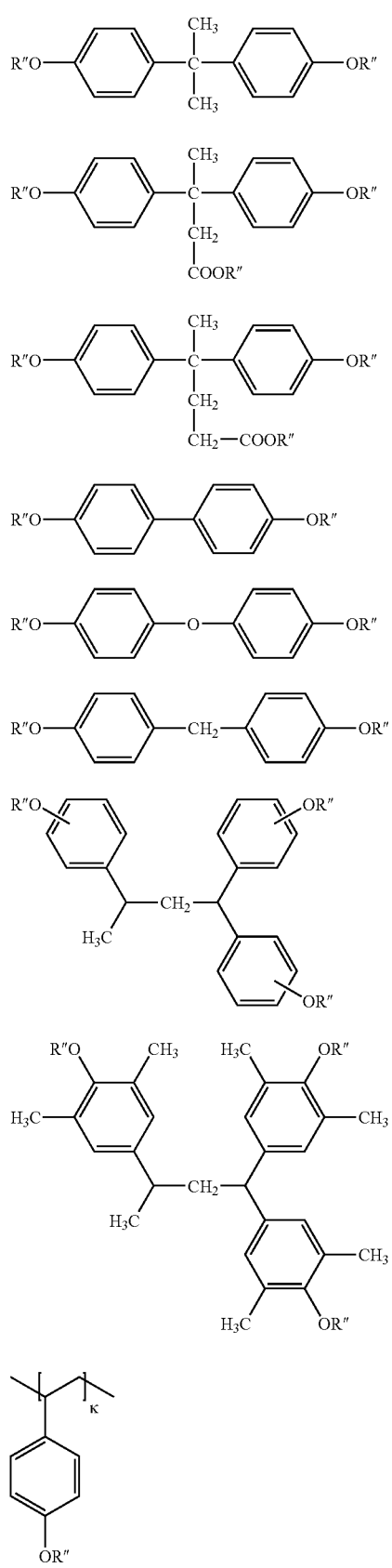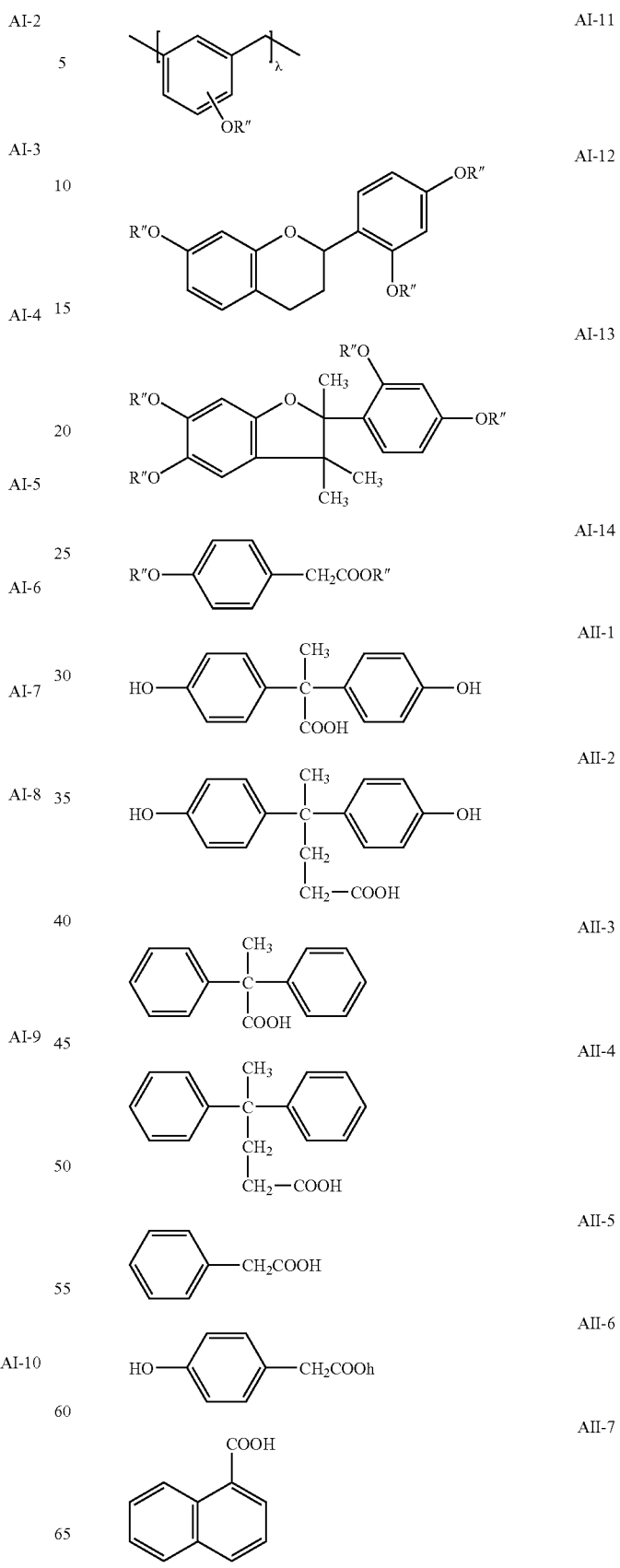

-continued

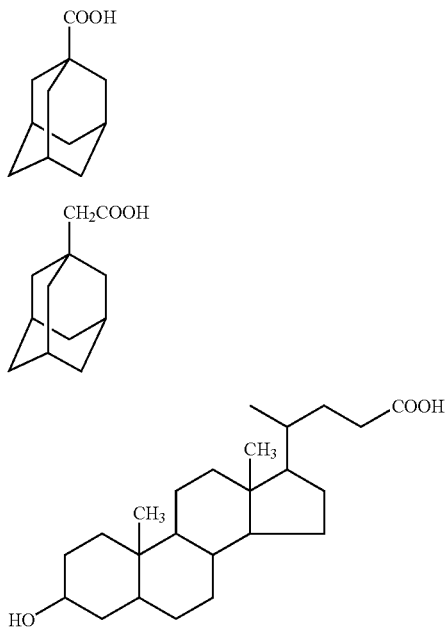

AII-8

AII-9

AII-10

(In the formulae, R" represents a hydrogen atom or a CH$_2$COOH group, and 10–100 mol % of R" is a CH$_2$COOH group in each compound. λ and κ show the same meaning as the above.)

An amount of addition of the compound which has the group represented by ≡C—COOH in the above-mentioned molecule is 0 to 5 parts, preferably 0.1 to 5 parts, more preferably 0.1 to 3 parts, still more preferably 0.1 to 2 parts to 100 parts of the base resin. If it is more than five parts, a resolving power of the resist composition may be lowered.

Furthermore, an acetylene alcohol derivative can be blended in the resist composition of the present invention as an additive, and thereby, preservation stability can be improved.

As the acetylene alcohol derivative, compounds represented by the following general formulae (S1) and (S2) can be used suitably.

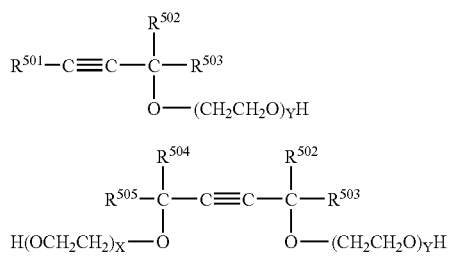

S1

S2

(In the formulae, R$^{501}$, R$^{502}$, R$^{503}$, R$^{504}$, and R$^{505}$ are a hydrogen atom or a linear, branched or cyclic alkyl group having 1–8 carbon atoms, and X and Y represent 0 or positive numbers, which satisfy the following equation: 0≦X≦30, 0≦Y≦30, and 0≦X+Y≦40.)

Examples of acetylene alcohol derivative may include: Surfynol 61, Surfynol 82, Surfynol 104, Surfynol 104E, Surfynol 104H, Surfynol 104A, Surfynol TG, Surfynol PC, Surfynol 440, Surfynol 465, Surfynol 485 (manufactured by Air Products and Chemicals Inc.), Surfynol E1004 (manufactured by Nisshin Kagaku Kogyo corporation) and the like.

The amount of addition of the above-mentioned acetylene alcohol derivative is 0.01 to 2% by weight, more preferably 0.02–1% by weight in 100% by weight of the resist composition.

If it is fewer than 0.01% by weight, the improvement effect of an application property and a preservation stability may not be achieved sufficiently. If it is more than 2% by weight, the resolving power of resist composition may be lowered.

A surfactant commonly used in order to improve application property can be added in the resist composition of the present invention as an arbitrary component in addition to the above-mentioned component. The amount of addition of the arbitrary component is in the range the effect of the present invention is not impeded.

The surfactant is preferably non-ionic one. Examples thereof may include: perfluoro alkyl polyoxyethylene ethanol, fluorinated alkyl ester, perfluoro alkylamine oxide, perfluoro alkyl EO addition product, a fluorine-containing organosiloxane compound, and the like. For example, Fluorad "FC-430", "FC-431" (all are manufactured by Sumitomo 3M), Surflon "S-141", "S-145", "KH-10", "KH-20", "KH-30", "KH-40" (all are manufactured by Asahi Glass Co., Ltd.), Unidyne "DS-401", "DS-403", "DS-451" (all are manufactured by Daikin Industries, LTD.), MEGAFACE "F-8151" (manufactured by Dainippon Ink Industry), "X-70-092", "X-70-093" (all are manufactured by Shin-Etsu Chemical Co., Ltd.), and the like. Preferably, Fluorad "FC-430" (manufactured by Sumitomo 3M), "KH-20", "KH-30" (all are manufactured by Asahi Glass Co., Ltd.), and "X-70-093" (manufactured by Shin-Etsu Chemical Co., Ltd.) are exemplified.

In order to form a pattern using the resist composition of the present invention, a well-known lithography technology can be adopted.

For example, the resist composition is applied on substrates such as a silicon wafer so that a thickness may be 0.2–2.0 μm by technique such as spin coating, it is then pre-baked at 60–150° C. for 1–10 minutes, preferably at 80–130° C. for 1–5 minutes on a hot plate, and thereby a resist film is formed. Subsequently, a mask for forming a target pattern is held above the above-mentioned resist film, irradiated with high-energy beams such as far ultraviolet rays, an excimer laser, an X-ray, and an electron ray, so that a light exposure amount may be about 1–200 mJ/cm$^2$, preferably about 5–100 mJ/cm$^2$, and then is subjected to postexposure bake (PEB) on a hot plate, at 60–150° C. for 1–5 minutes, preferably at 80–130° C. for 1–3 minutes.

The target pattern is formed on a substrate by developing for 0.1–3 minutes, preferably for 0.5–2 minutes using a developer of an alkali solution such as 0.1 to 5%, preferably 2 to 3% tetramethyl ammonium hydroxide (TMAH), according to a conventional method, such as a dip method, a puddle method, and a spray method. The material of the present invention is suitable especially for detailed patterning by far ultraviolet rays or the excimer laser, the X-ray and the electron ray also at 248–193 nm among the high-energy beam.

EXAMPLES

The present invention will be specifically explained below with reffering to Synthetic examples, Comparative synthetic examples, Examples, Comparative examples. However, the present invention is not limited to the following examples and the like.

Synthetic Examples, Comparative Synthetic Examples

Synthetic Example 1

The compounds of the present invention were synthesized according to a method shown below.

Synthetic Example 1-1 (Synthesis of Monomer 1)

12.4 g of 5-hydroxy methyl-2-norbornene and 300 ml of methylene chloride were put in a flask, and 28.7 g (75% content) of m-chloro perbenzoic acid was dropped therein at 30° C. After completion of dropping, it was agitated at the temperature for 1 hour, then it was cooled to 0° C., and the precipitated benzoic acid was removed by filtration. The filtrate was washed with an aqueous solution of sodium sulfite, an aqueous solution of sodium bicarbonate, and then the organic layer was concentrated under a reduced pressure. The resultant crude 2,3-epoxy-5-hydroxy methyl norbornane, 100 ml of toluene and a catalytic amount of a concentrated sulfuric acid were put in a flask, and agitated at 50° C. for 2 hours. Then, usual after-treatment was carried out to yield 10.1 g of 2-hydroxy-4-oxatricyclo[4.2.1.0$^{3,7}$]nonane.

Next, 7.1 g of 2-hydroxy-4-oxatricyclo[4.2.1.0$^{3,7}$]nonane and 7.1 g of triethylamine were dissolved in 80 ml of toluene. 5.4 g of acrylic-acid chloride was added thereto at 10° C., and agitated at the temperature for 1 hour. 50 ml of water was added thereto at 30° C. or lower, and usual after-treatment was performed. Then, it was purified with a silica gel chromatography to yield 7.3 g of Monomer 1 (acrylic-acid 4-oxatricyclo[4.2.1.0$^{3,7}$]nonane-2-yl) was obtained (yield was 54% in two steps).

The obtained product was analyzed by IR (thin film), $^1$H-NMR (300 MHz in CDCl$_3$) and the like to be identified. Analytical data are shown below.

IR (thin film): ν=2969, 2869, 1724, 1635, 1618, 1448, 1405, 1301, 1290, 1267, 1189, 1145, 1074, 1051, 1035, 998, 946, 908, 809cm$^{-1}$ $^1$H-NMR (300MHz in CDCl$_3$): δ=1.12 (1H,ddd), 1.54 (1H,dd), 1.77–1.97 (2H,m), 2.26 (1H,m), 2.30–2.39 (1H,m), 2.62–2.68 (1H,m), 3.70 (1H,d), 3.82 (1H,dd), 4.11 (1H, dd), 4.40 (1H, m), 5.79 (1H,dd), 6.08 (1H,dd) ppm Synthetic Example 1-2 (Synthesis of Monomer 2)

Monomer 2 (methacrylic-acid 4-oxatricyclo[4.2.1.0$^{3,7}$]nonane-2-yl) was obtained by the same method as Synthetic example 1-1 except that methacrylic acid chloride was used instead of acrylic acid chloride (yield was 58% in two steps).

The obtained product was analyzed as described in Synthetic example 1, to be identified. Analytical data are shown below.

IR (thin film): ν=2971, 2869, 1716, 1637, 1448, 1403, 1378, 1363, 1324, 1307, 1288, 1166, 1145, 1072, 1035, 1012, 997, 946, 908, 846, 813 cm$^{-1}$ $^1$H-NMR (300 MHz in CDCl$_3$): δ=1.12 (1H,ddd), 1.55 (1H,dd), 1.80–1.96 (5H,m), 2.25 (1H,m), 2.30–2.38 (1H,m), 2.61–2.67 (1H,m), 3.70 (1H,d), 3.80 (1H,dd), 4.10 (1H, dd), 4.38 (1H,t), 5.51 (1H,m), 6.04 (1H,m) ppm $^{13}$C-NMR (75 MHz in CDCl$_3$): δ=18.2, 33.4, 34.1, 37.3, 38.9, 44.8, 75.2, 83.0, 85.2, 125.2, 136.5, 166.4 ppm Synthetic Example 1-3 (Synthesis of Monomer 3)

Monomer 3 (methacrylic-acid-4-oxatetracyclo[6.3.0.0$^{3,10}$.0$^{5,9}$]undecane-2-yl) was obtained by the same method as Synthetic example 1–1 except that 6-hydroxy tricyclo[5.2.1.0$^{5,9}$]deca-2-en was used instead of 5-hydroxymethyl-2-norbornene, and methacrylic-acid chloride was used instead of acrylic-acid chloride (yield was 51% in two steps).

The obtained product was analyzed as described in Synthetic example 1, to be identified. Analytical data are shown below.

Boiling point: 87–88/27Pa IR (Thin film): ν=2958, 2927, 2885, 1716, 1637, 1463, 1434, 1403, 1380, 1328, 1295, 1164, 1133, 1118, 1103, 1058, 1016, 985, 954, 881, 833, 813cm$^{-1}$ $^1$H-NMR (300 MHz in CDCl$_3$): δ=1.65 (1H,m), 1.69–1.92 (6H,m), 1.96 (1H,dd), 2.02–2.13 (1H,m), 2.19–2.25 (1H,m), 2.51–2.63 (1H,m), 2.66–2.73 (1H,m), 2.74–2.80 (1H,m), 4.11 (1H,dd), 4.42 (1H,t), 4.68 (1H,s) 5.52 (1H,m), 6.05 (1H,m) ppm $^{13}$C-NMR (75 MHz in CDCl$_3$): δ=18.2, 22.5, 36.8, 37.1, 42.9, 44.4, 47.1, 51.5, 76.6, 77.0, 77.4, 80.2, 85.3, 85.4, 125.2, 136.5, 166.4 ppm Synthetic Example 1-4 (Synthesis of Monomer 4)

240 ml of 1 M solution of methyl magnesium chloride in tetrahydrofuran was put in a flask, and 17.0 g of methyl 5,6-epoxy-7-oxa-2-norbornane carboxylate was dropped thereto at 40° C. or lower. After agitating at a room temperature for 1 hour, an aqueous solution of ammonium-chloride was added thereto to hydrolyze it. Then, usual after-treatment was carryied out to yield 11.9 g of 2-hydroxy-4,8-dioxa-5,5-dimethyl tricyclo[4.2.1.0$^{3,7}$]nonane.

Next, 8.5 g of 2-hydroxy-4,8-dioxa-5,5-dimethyl tricyclo[4.2.1.0$^{3,7}$]nonane, 10.8 g of methacrylic acid, 1.9 g of p-toluenesulfonic-acid monohydrates, and 0.05 g of p-methoxy phenol were dissolved in 30 ml of toluene. The temperature was raised to 110° C., and a mixture of water and toluene was evaporated at a rate of 5–10 ml per hour. 10–20 ml of toluene was added to the reaction system every 2 hours. After 8 hours, 20 ml of water was added at 30° C. or lower, and usual after-treatment was performed. Distillation was performed at a reduced pressure, to yield 8.8 g of Monomer 4 (methacrylic-acid 4,8-dioxa-5,5-dimethyl tricyclo[4.2.1.0$^{3,7}$]nonane-2-yl) (yield was 52% in two steps).

The obtained product was analyzed as described in Synthetic example 1, to be identified. Analytical data are shown below.

Boiling point: 98–102/27Pa IR (thin film): ν=2979, 2950, 2929, 2875, 1706, 1633, 1470, 1448, 1382, 1369, 1328, 1307, 1295, 1195, 1170, 1074, 1060, 1037, 1027, 998, 975, 964, 948, 939, 883, 860, 823, 800 cm$^{-1}$ $^1$H-NMR (600 MHz in CDCl$_3$): δ=1.19 (3H,s), 1.28 (3H,s), 1.76 (1H,ddd), 1.79 (1H,ddd), 2.23 (1H,m), 4.16 (1H,dd), 4.46–4.49 (1H,m), 4.50 (1H,s), 5.17 (1H,dd), 5.55 (1H,m), 6.09 (1H,m) ppm $^{13}$C-NMR (150 MHz in CDCl$_3$): δ=18.3, 25.9, 28.3, 30.3, 47.1, 78.9, 82.2, 82.6, 82.8, 82.9, 126.1, 136.0, 166.8 ppm Synthetic Example 1-5 (Synthesis of Monomer 5)

Monomer 5 (acrylic acid 4,8-dioxa-5,5-dimethyl tricyclo[4.2.1.0$^{3,7}$]nonane-2-yl) was obtained by the same method as Synthetic example 1-4 except that acrylic acid was used instead of methacrylic acid (yield was 50% in two steps).

The obtained product was analyzed as described in Synthetic example 1, to be identified. Analytical data are shown below.

Boiling point: 91–93/27Pa IR (thin film): ν=2971, 2871, 1725, 1633, 1619, 1469, 1450, 1407, 1384, 1369, 1303, 1268, 1224, 1193, 1180, 1130, 1066, 1051, 1027, 997, 973, 873, 827, 811cm$^{-1}$ $^1$H-NMR (600 MHz in CDCl$_3$): δ=1.18 (3H, s), 1.28 (3H, s), 1.74–1.82 (2H, m), 2.24 (1H, m), 4.16 (1H, dd), 4.47 (1H, d), 4.54 (1H, s), 5.82 (1H, dd), 6.10 (1H, dd), 6.40 (1H, dd) ppm Synthetic Example 1-6 (Synthesis of Monomer 6)

Monomer 6 (2-(trifluoro methyl) acrylic acid 4,8-dioxa-5,5-dimethyl tricyclo[4.2.1.0$^{3,7}$]nonane-2-yl) was obtained by the same method as Synthetic example 1-4 except that 2-(trifluoro methyl)acrylic acid was used instead of the methacrylic acid (yield was 50% in two steps).

The obtained product was analyzed as described in Synthetic example 1, to be identified. Analytical data are shown below.

IR (Thin film): ν=3018, 3000, 2975, 2931, 1731, 1457, 1405, 1386, 1359, 1301, 1278, 1253, 1166, 1145, 1093, 1074, 1054, 1027, 995, 987, 970, 954, 877, 858, 823, 811, 796 cm$^{-1}$ $^1$H-NMR (600 MHz in CDCl$_3$): δ=1.20 (3H, s), 1.29 (3H, s), 1.76 (1H, dd), 1.81 (1H, ddd), 2.26 (1H, m), 4.19 (1H, dd), 4.51 (1H, d), 4.60 (1H, s), 5.21 (1H, t), 6.44 (1H, m), 6.70(1H, m) ppm $^{13}$C-NMR (150 MHz in CDCl$_3$): δ=25.8, 28.1, 30.1, 46.9, 78.5, 82.4, 82.5, 82.8, 83.5, 120.2, 122.0, 131.1(q), 133.1 ppm $^{19}$F—NMR (565 MHz in CDCl$_3$): δ=−66.6 (CF$_3$CO$_2$H standard)

Synthetic Example 1-7 (Synthesis of Monomer 7)

Monomer 7 (2-(trifluoro methyl)acrylic-acid 4-oxatricyclo[4.2.1.0$^{3,7}$]nonane-2-yl) was obtained by the same method as Synthetic example 1-1 except that 2-(trifluoromethyl)acrylic-acid chloride instead of acrylic-acid chloride (yield was 48% in two steps).

The obtained product was analyzed as described in Synthetic example 1, to be identified.

Synthetic Example 1-8 (Synthesis of Monomer 8)

Monomer 8 (a methacrylic acid 4,8-dioxatricyclo[4.2.1.0$^{3,7}$]nonane-2-yl) was obtained by the same method as Synthetic example 1–1 except that 5-hydroxymethyl-7-oxa-2-norbornene was used instead of 5-hydroxymethyl-2-norbornene, and methacrylic-acid chloride was used instead of acrylic-acid chloride (yield was 53% in two steps).

The obtained product was analyzed as described in Synthetic example 1, to be identified.

Synthetic Example 1-9 (Synthesis of Monomer 9)

Monomer 9 (acrylic acid 4,8-dioxatricyclo[4.2.1.0$^{3,7}$]nonane-2-yl) was obtained by the same method as Synthetic example 1-1 except that 5-hydroxy methyl-7-oxa 2-norbornene was used instead of 5-hydroxy methyl-2-norbornene (yield was 51% in two steps).

The obtained product was analyzed as described in Synthetic example 1, to be identified.

Synthetic Example 1-10 (Synthesis of Monomer 10)

Monomer 10 (methacrylic acid 4-oxa-5,5-dimethyl tricyclo[4.2.1.0$^{3,7}$]nonane-2-yl) was obtained by the same method as Synthetic example 1-4 except that 5,6-epoxy-2-norbornane carboxylic-acid methyl was used instead of 5,6-epoxy-7-oxa-2-norbornane carboxylic-acid methyl (yield was 58% in two steps).

The obtained product was analyzed as described in Synthetic example 1, to be identified.

Synthetic Example 1-11 (Synthesis of Monomer 11)

Monomer 11 (acrylic-acid 4-oxa 5 and 5-dimethyl tricyclo[4.2.1.0$^{3,7}$]nonane-2-yl) was obtained by the same method as Synthetic example 1-4 except that 5,6-epoxy 2-norbornane carboxylic-acid methyl was used instead of 5,6-epoxy-7-oxa 2-norbornane carboxylic-acid methyl, and acrylic acid was used instead of methacrylic acid (yield was 53% in two steps). The obtained product was analyzed as described in Synthetic example 1, to be identified.

Synthetic Example 1-12 (Synthesis of Monomer 12)

27.2 g of Monomer 1 was dissolved in 30 ml of toluene, and 11.6 g of cyclopentadiene was dropped therein at 30° C. or lower. After agitating at 50° C. for 10 hours, 34.6 g of Monomer 12 (5-norbornene-2-carboxylic-acid 4-oxatricyclo[4.2.1.0$^{3,7}$]nonane-2-yl) was obtained by vacuum distillation (yield 95%).

The obtained product was analyzed as described in Synthetic example 1, to be identified.

Synthetic Example 1-13 (Synthesis of Monomer 13)

Monomer 13 (5-norbornene-2-carboxylic acid 4,8-dioxa 5,5-dimethyl tricyclo[4.2.1.0$^{3,7}$]nonane-2-yl) was obtained by the same method as Synthetic example 1-12 except that Monomer 5 was used instead of Monomer 1 (yield 96%).

The obtained product was analyzed as described in Synthetic example 1, to be identified.

Synthetic Example 1-14 (Synthesis of Monomer 14)

Monomer 14 (5-norbornene-2-carboxylic acid-4,8-dioxatricyclo[4.2.1.0$^{3,7}$]nonane-2-yl) was obtained by the same method as Synthetic example 1-12 except that Monomer 9 was used instead of Monomer 1 (yield 94%). The obtained product was analyzed as described in Synthetic example 1, to be identified.

Synthetic Example 1-15 (Synthesis of Monomer 15)

Monomer 15 (5-norbornene-2-carboxylic-acid 4-oxa-5,5-dimethyl tricyclo[4.2.1.0$^{3,7}$]nonane-2-yl) was obtained by the same method as Synthetic example 1–12 except that Monomer 11 was used instead of Monomer 1 (95% of yield).

The obtained product was analyzed as described in Synthetic example 1, to be identified.

monomer 1

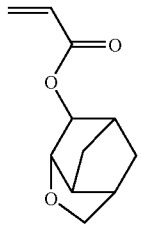

monomer 2

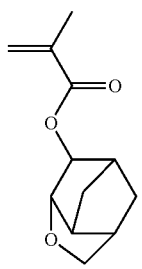

monomer 3
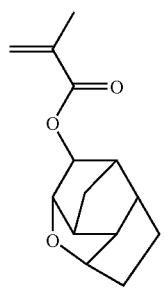
monomer 4
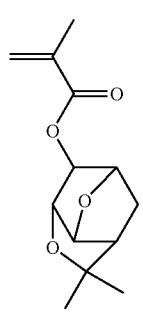
monomer 5
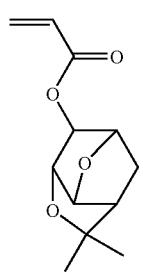
monomer 6
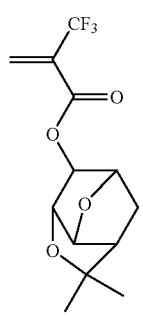
monomer 7
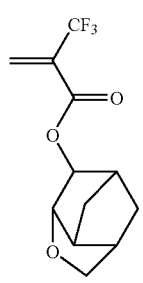
monomer 8
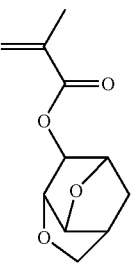
monomer 9
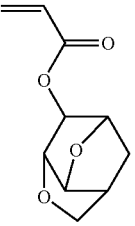
monomer 10
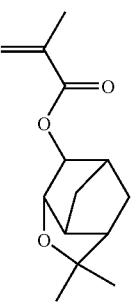
monomer 11
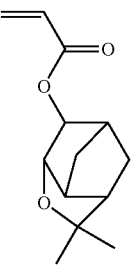
monomer 12
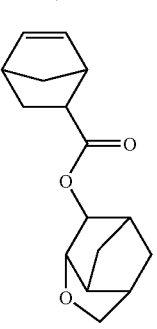

-continued monomer 13

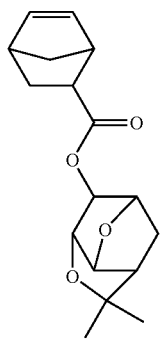

monomer 14

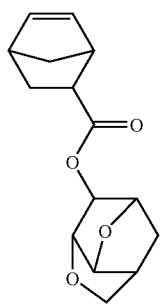

monomer 15

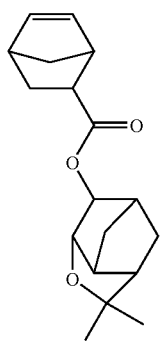

It was shown that the compound of the present invention can be easily obtained at high yield according to the above synthetic methods.

Synthetic Example 2

The polymers (Polymers 1–6) of the present invention and the polymers (Polymers 7 and 8) for comparison were synthesized as described below.

Synthetic Example 2-1 (Synthesis of Polymer 1)

27.9 g of Monomer 2, 22.1 g of methacrylic-acid 2-ethyl-2-adamantyl and 150 g of tetrahydrofuran were mixed. This reaction mixture was heated to 60° C., and 1.7 g of 2,2'-azobis (2,4-dimethyl valeronitril) was added thereto, and stirred for 15 hours with keeping at 60° C. After cooling to a room temperature, the reaction liquid was dropped with stirring vigorously to 1L of methanol. The produced solid was taken by filtration and dried in a reduced pressure at 40° C. for 15 hours, to yield a polymer represented by the following formula polymer 1 as white powdery solid. Yield was 46 g, 92%. Mw expresses a weight average molecular weight measured using GPC in polystyrene conversion.

polymer 1

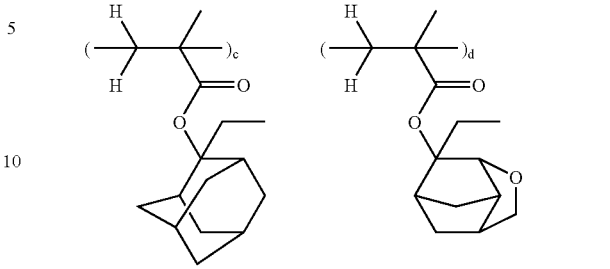

Copolymerization ratio c:d=0.40:0.60

Weight-average-molecular-weight (Mw)=9,000

Synthetic Examples 2-2 to 2-6 (Synthesis of Polymers 2-6)

The following Polymers 2-6 were synthesized by well-known method as described above.

polymer 2

Copolymerization ratio c:d:e=0.30:0.30:0.40

Weight-average-molecular-weight (Mw)=10,200 polymer 3

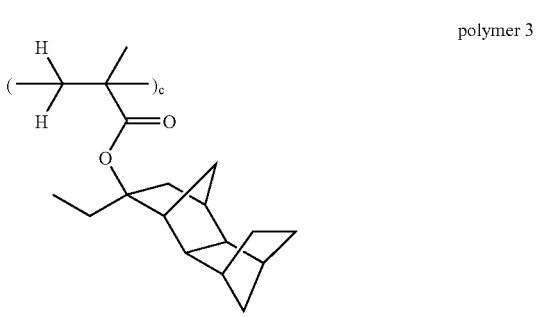

-continued

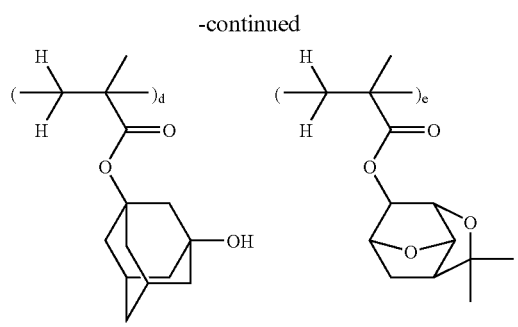

Copolymerization ratio c:d:e=0.30:0.30:0.40
Weight-average-molecular-weight (Mw)=10,000 polymer 4

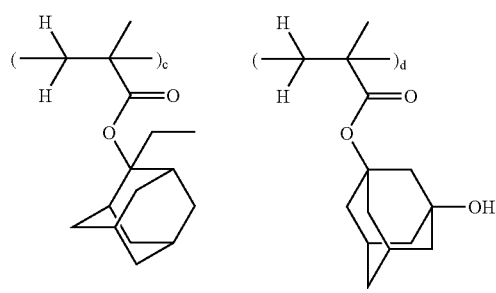

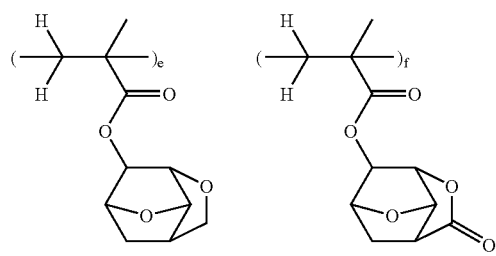

Copolymerization ratio c:d:e:f=0.35:0.25:0.20:0.20
weight-average-molecular-weight (Mw)=9,400 polymer 5

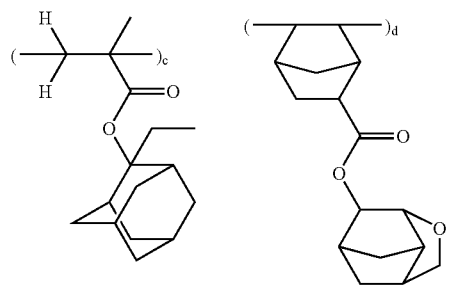

-continued

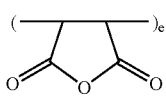

Copolymerization ratio c:d:e=0.30:0.35:0.35
Weight-average-molecular-weight (Mw)=9,200 polymer 6

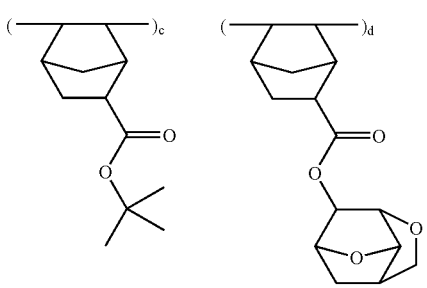

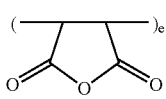

Copolymerization ratio c:d:e=0.25:0.25:0.50
Weight-average-molecular-weight (Mw)=7,100

Comparative Synthetic Example

Comparative Synthetic Examples 1-1 and 1-2
(Synthesis of Polymers 7 and 8)

The following polymers 7 and 8 were synthesized.

polymer 7

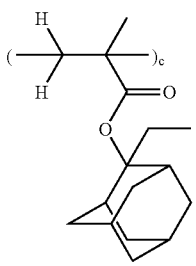 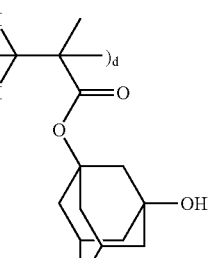

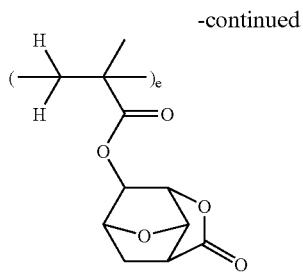

-continued

Copolymerization ratio c:d:e=0.35:0.30:0.35

Weight-average-molecular-weight (Mw)=8,200

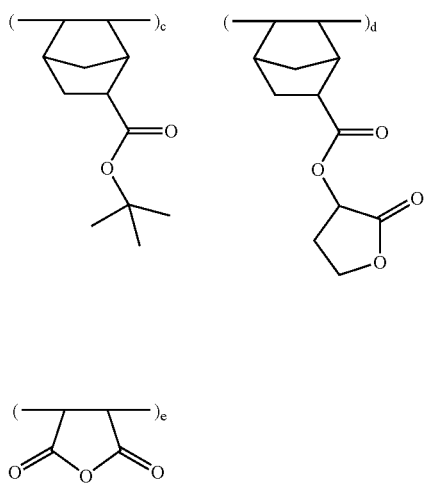

polymer 8

Copolymerization ratio c:d:e=0.25:0.25:0.50

Weight-average-molecular-weight (Mw)=7,700

[Evaluation of Effect of Reducing Swelling]

The effect of reducing swelling in the case that the polymers of the present invention was blended as a base resin in a resist composition was evaluated.

The polymers obtained in the above-mentioned Synthetic examples 2-1 to 2-6, Comparative synthetic examples 1-1 and 1-2 were used as the base resin, and an acid generating agent, an organic solvent containing a basic compound and 0.01% by weight of FC-430 (manufactured by Sumitomo 3M) was mixed therewith in the compositions shown in Table 1. Next, they were filtered with a filter made of Teflon (a registered trademark) (a pore size of 0.2 μm), to yield the resist compositions (Examples 1-1 to 1-6, Comparative Examples 1-1, 1-2).

Each composition in Table 1 is as follows.

Base resin: Polymers 1 to 6 (Synthetic example 2-1 to 2-6), polymers 7 and 8 (Comparative synthetic examples 1-1 and 1-2)

Acid generating agent: TPSNf (nonafluoro butane sulfonic-acid triphenyl sulfonium)

Basic compound: TMMEA (tris methoxy methoxy ethylamine)

Organic-solvent: PGMEA (propylene glycol monomethyl ether acetate)

The solution of the resist composition prepared above was applied by rotation application on a silicon wafer on which hexamethyldisilazane was atomized at 90° C. for 90 seconds, and subjected to a heat treatment at 110° C. for 90 seconds, to form a resist film with a thickness of 0.5 μm. It was exposed using KrF excimer laser stepper (manufactured by NIKON CORP., NA=0.5) at a light exposure amount of 11 points in total which consist of a sensitivity (Eth, mJ/cm$^2$) which measured separately as a central value and every five points upward and downward at a 5% pitch, and then subjected to heat treatment at 110° C. for 90 seconds. The thickness at each exposing point was measured, and defined as a thickness before development (Å). Then, the silicon wafer was immersed in 2.38% solution of tetramethyl ammonium hydroxide for 200 seconds to be developed, and a thickness at each exposing point was measured again, and defined as the thickness after development (Å). The thickness before development and the thickness after development at each exposing point was compared. If the thickness after development was increased, it was considered that swelling was caused, and the maximum increased amount was defined as of the amount of swelling (Å).

Composition and the result of the evaluation of each resist are shown in Table 1.

TABLE 1

|  |  | Base resin (Parts by weight) | Acid generating agent (Parts by weight) | Basic compound (Parts by weight) | Organic Solvent (Parts by weight) | Swelling Amount (Å) |
|---|---|---|---|---|---|---|
| Example | 1-1 | Polymer 1 (80) | TPSNf (1.090) | TMMEA (0.236) | PGMEA (480) | −13 |
|  | 1-2 | Polymer 2 (80) | TPSNf (1.090) | TMMEA (0.236) | PGMEA (480) | −18 |
|  | 1-3 | Polymer 3 (80) | TPSNf (1.090) | TMMEA (0.236) | PGMEA (480) | −16 |
|  | 1-4 | Polymer 4 (80) | TPSNf (1.090) | TMMEA (0.236) | PGMEA (480) | −32 |
|  | 1-5 | Polymer 5 (80) | TPSNf (1.090) | TMMEA (0.236) | PGMEA (480) | −23 |
|  | 1-6 | Polymer 6 (80) | TPSNf (1.090) | TMMEA (0.236) | PGMEA (480) | −16 |

TABLE 1-continued

|  |  | Base resin (Parts by weight) | Acid generating agent (Parts by weight) | Basic compound (Parts by weight) | Organic Solvent (Parts by weight) | Swelling Amount (Å) |
|---|---|---|---|---|---|---|
| Comparative Example | 1-1 | Polymer 7 (80) | TPSNf (1.090) | TMMEA (0.236) | PGMEA (480) | 63 |
|  | 1-2 | Polymer 8 (80) | TPSNf (1.090) | TMMEA (0.236) | PGMEA (480) | 32 |

From the results in Table 1, it was confirmed that the resist compositions (Examples 1-1 to 1-6) using the polymer containing the repeating unit of the compound of the present invention as the base resin has a high effect of reducing swelling.

[Evaluation of a Dependency on Thin or Dense and a Resolving Power]

A dependency on thin or dense and a resolving power were evaluated in the case that the polymer of the present invention was blended as a base resin in the resist composition.

The polymer obtained in the above-mentioned Synthetic examples 2-1 to 2-6 and Comparative synthetic examples 1-1 and 1-2 of comparison composition were used as the base resin, and an acid generating agent, an organic solvent containing a basic compound and 0.01% by weight of FC-430 (manufactured by Sumitomo 3M) was mixed therewith in the compositions shown in Table 2. Next, they were filtered with a filter made of Teflon (a registered trademark) (a pore size of 0.2 μm), to yield the resist compositions (Examples 2-1 to 2-6 and Comparative Examples 2-1, 2-2).

Each composition in Table 2 is as follows.

Base resin: Polymers 1 to 6 (Synthetic example 2-1 to 2-6), polymers 7 and 8 (Comparative synthetic examples 1-1 and 1-2)

Acid generating agent: TPSNf (nonafluoro butane sulfonic-acid triphenyl sulfonium)

Basic compound: TMMEA (tris methoxy methoxy ethylamine)

Organic-solvent: PGMEA (propylene glycol monomethyl ether acetate)

An anti-reflection film (AR-19 manufactured by Shipley) was applied on a silicon wafer, baked at 200° C. for 60 seconds, to produce a wafer (thickness of 82 μm). On the wafer, the solution of the resist composition prepared above was spin-coated, and baked at 130° C. for 60 seconds using a hot plate, to form a resist film with a thickness of 0.3 μm. It was exposed using ArF excimer laser stepper (manufactured by NIKON CORP., NA=0.68, σ0.75), and subjected to heat treatment at 110° C. for 90 seconds, and then a puddle development was performed for 30 seconds using 2.38% solution of tetramethyl ammonium hydroxide. The wafer after development was broken, and observed by a cross sectional SEM (scanning electron microscope). The exposure amount resolving line and space in a group of 0.13 μm at 1:1 was defined as an optimal light exposure amount, and the minimum line width (μm) of line and space separated at this light exposure amount was defined as the resolution of the evaluated resist. Moreover, the configuration of the pattern at that time was classified into rectangle, round head, T-top, taper, and reverse taper.

Composition and the result of evaluation of each resist are shown in Table 2.

TABLE 2

|  |  | Base resin (Parts by weight) | Acid generating agent (Parts by weight) | Basic compound (Parts by weight) | Organic Solvent (Parts by weight) | Optimum Exposure amount (mJ/cm$^2$) | Resolving power (μm) | Shape |
|---|---|---|---|---|---|---|---|---|
| Example | 2-1 | Polymer 1 (80) | TPSNf (1.090) | TMMEA (0.236) | PGMEA (480) | 20 | 0.11 | Rectangle |
|  | 2-2 | Polymer 2 (80) | TPSNf (1.090) | TMMEA (0.236) | PGMEA (480) | 19 | 0.11 | Rectangle |
|  | 2-3 | Polymer 3 (80) | TPSNf (1.090) | TMMEA (0.236) | PGMEA (480) | 19 | 0.11 | Rectangle |
|  | 2-4 | Polymer 4 (80) | TPSNf (1.090) | TMMEA (0.236) | PGMEA (480) | 21 | 0.11 | Rectangle |
|  | 2-5 | Polymer 5 (80) | TPSNf (1.090) | TMMEA (0.236) | PGMEA (480) | 24 | 0.11 | Rectangle |
|  | 2-6 | Polymer 6 (80) | TPSNf (1.090) | TMMEA (0.236) | PGMEA (480) | 21 | 0.11 | Rectangle |
| Comparative Example | 2-1 | Polymer 7 (80) | TPSNf (1.090) | TMMEA (0.236) | PGMEA (480) | 35 | 0.13 | T-top |
|  | 2-2 | Polymer 8 (80) | TPSNf (1.090) | TMMEA (0.236) | PGMEA (480) | 25 | 0.13 | Taper |

From the results in Table 2, it was confirmed that the resist compositions (Examples 2-1 to 2-6) using the polymer containing as a repeating unit the compound of the present invention as the base resin has high sensitivity and high resolving power in ArF excimer laser exposure.

The present invention is not limited to the above-described embodiment. The above-described embodiment is a mere example, and those having the substantially same structure as that described in the appended claims and providing the similar action and effects are included in the scope of the present invention.

What is claimed is:

1. A compound represented by the following general formula (1),

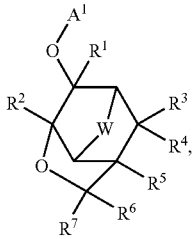

(1)

wherein $A^1$ represents a polymerizable functional group which has a carbon-carbon double bond at least, $R^1$ and $R^2$ independently represent a hydrogen atom, or a linear, branched or cyclic monovalent hydrocarbon group having 1–10 carbon atoms, $R^3$–$R^7$ independently represent a hydrogen atom, or a linear, branched or cyclic monovalent hydrocarbon group having 1–10 carbon atoms which may contain a hetero atom, or two of $R^3$–$R^7$ may bond to each other and form an aliphatic-hydrocarbon ring, and W represents any one of $CH_2$, an oxygen atom and a sulfur atom.

2. The compound according to claim 1 which is a compound represented by the following general formula (2),

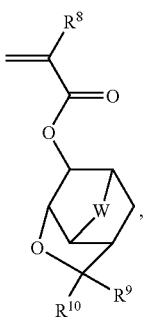

(2)

wherein W is the same as that of the above-mentioned formula, $R^8$ represents a hydrogen atom, a methyl group, or a trifluoro methyl group, and $R^9$ and $R^{10}$ independently represent a hydrogen atom, a linear, branched, or cyclic monovalent hydrocarbon group having 1–10 carbon atoms, or $R^9$ and $R^{10}$ may bond to each other and form an aliphatic-hydrocarbon ring together with carbon atoms to which they bond.

3. The compound according to claim 1 which is a compound represented by the following general formula (3),

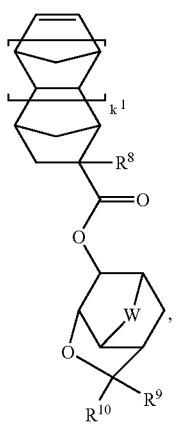

(3)

wherein $R^8$ represents a hydrogen atom, a methyl group, or a trifluoro methyl group, $R^9$ and $R^{10}$ independently represent a hydrogen atom, a linear, branched, or cyclic monovalent hydrocarbon group having 1–10 carbon atoms, or $R^9$ and $R^{10}$ may bond to each other and form an aliphatic-hydrocarbon ring together with carbon atoms to which they bond, W represents any one of $CH_2$, an oxygen atom and a sulfur atom, and $k^1$ is 0 or 1.

4. A polymer comprising at least the compound according to claim 1 as a repeating unit.

5. A polymer comprising at least the compound according to claim 2 as a repeating unit.

6. A polymer comprising at least the compound according to claim 3 as a repeating unit.

7. A resist composition which contains at least the polymer according to claim 4 as a base resin.

8. A resist composition which contains at least the polymer according to claim 5 as a base resin.

9. A resist composition which contains at least the polymer according to claim 6 as a base resin.

10. The resist composition according to claim 7 which is a chemically amplified resist composition, further containing an organic solvent and an acid generating agent.

11. The resist composition according to claim 8 which is a chemically amplified resist composition, further containing an organic solvent and an acid generating agent.

12. The resist composition according to claim 9 which is a chemically amplified resist composition, further containing an organic solvent and an acid generating agent.

13. The resist composition according to claim 7 which further contains a dissolution controlling agent.

14. The resist composition according to claim 8 which further contains a dissolution controlling agent.

15. The resist composition according to claim 9 which further contains a dissolution controlling agent.

16. The resist composition according to claim 10 which further contains a dissolution controlling agent.

17. The resist composition according to claim 11 which further contains a dissolution controlling agent.

18. The resist composition according to claim 12 which further contains a dissolution controlling agent.

19. The resist composition according to claim 7 which further contains one or more of a basic compound, an acetylene alcohol derivative and a surfactant.

20. The resist composition according to claim 8 which further contains one or more of a basic compound, an acetylene alcohol derivative and a surfactant.

21. The resist composition according to claim 9 which further contains one or more of a basic compound, an acetylene alcohol derivative and a surfactant.

22. The resist composition according to claim 10 which further contains one or more of a basic compound, an acetylene alcohol derivative and a surfactant.

23. The resist composition according to claim 11 which further contains one or more of a basic compound, an acetylene alcohol derivative and a surfactant.

24. The resist composition according to claim 12 which further contains one or more of a basic compound, an acetylene alcohol derivative and a surfactant.

25. The resist composition according to claim 13 which further contains one or more of a basic compound, an acetylene alcohol derivative and a surfactant.

26. The resist composition according to claim 14 which further contains one or more of a basic compound, an acetylene alcohol derivative and a surfactant.

27. The resist composition according to claim 15 which further contains one or more of a basic compound, an acetylene alcohol derivative and a surfactant.

28. The resist composition according to claim 16 which further contains one or more of a basic compound, an acetylene alcohol derivative and a surfactant.

29. The resist composition according to claim 17 which further contains one or more of a basic compound, an acetylene alcohol derivative and a surfactant.

30. The resist composition according to claim 18 which further contains one or more of a basic compound, an acetylene alcohol derivative and a surfactant.

31. A patterning process on a substrate, comprising, at least, a step of applying the resist composition according to claim 7 on the substrate, a step of exposing the applied resist composition with a high-energy beam after heat-treatment, and a step of developing the exposed resist composition using a developer.

32. A patterning process on a substrate, comprising, at least, a step of applying the resist composition according to claim 8 on the substrate, a step of exposing the applied resist composition with a high-energy beam after heat-treatment, and a step of developing the exposed resist composition using a developer.

33. A patterning process on a substrate, comprising, at least, a step of applying the resist composition according to claim 9 on the substrate, a step of exposing the applied resist composition with a high-energy beam after heat-treatment, and a step of developing the exposed resist composition using a developer.

* * * * *